US008399739B2

(12) United States Patent
Spangenberg et al.

(10) Patent No.: US 8,399,739 B2
(45) Date of Patent: Mar. 19, 2013

(54) MANIPULATION OF PLANT SENESCENCE USING MODIFIED PROMOTERS

(75) Inventors: German Spangenberg, Bundoora (AU); Carl McDonald Ramage, Craigieburn (AU); Melissa Ann Palviainen, Eden Park (AU); Roger W. Parish, Warrandyte (AU); Joshua Heazlewood, Duncraig (AU)

(73) Assignees: Agriculture Victoria Services Pty, Attwood (AU); La Trobe University, Bundoora (AU)

( * ) Notice: Subject to any disclaimer, the term of this patent is extended or adjusted under 35 U.S.C. 154(b) by 445 days.

(21) Appl. No.: 12/605,214

(22) Filed: Oct. 23, 2009

(65) Prior Publication Data

US 2010/0192259 A1    Jul. 29, 2010

Related U.S. Application Data

(63) Continuation-in-part of application No. 11/789,526, filed on Apr. 24, 2007, now abandoned, which is a continuation-in-part of application No. 10/363,723, filed as application No. PCT/AU01/01092 on Aug. 30, 2001, now Pat. No. 7,227,055, application No. 12/605,214, which is a continuation-in-part of application No. PCT/AU2008/000566, filed on Apr. 21, 2008.

(30) Foreign Application Priority Data

Sep. 6, 2000  (AU) .................................. PQ9946

(51) Int. Cl.
*A01H 1/00* (2006.01)
*A01H 5/00* (2006.01)
*A01H 5/10* (2006.01)
*C12N 15/09* (2006.01)
*C12N 15/82* (2006.01)

(52) U.S. Cl. ........ 800/290; 800/278; 800/298; 800/295; 435/320.1; 435/419; 435/468

(58) Field of Classification Search .................. None
See application file for complete search history.

(56) References Cited

FOREIGN PATENT DOCUMENTS

| WO | WO 96/29858 A1 | 10/1996 |
| WO | WO 00/70061 A2 | 11/2000 |
| WO | WO 02/20772 A1 | 3/2002 |

OTHER PUBLICATIONS

Agriculture Victoria Services Pty Ltd et al., "International Search Report and Written Opinion of the International Searching Authority," issued in related International Patent Application No. PCT/AU2008/000556 by the Australian Patent Office on Jun. 2008, citing the five references disclosed in this Information Disclosure Statement.
Gan S. et al., "Developmental Targeting of Gene Expression by the Use of a Senescence-specific Promoter," Inducible Gene Expression in Plants, Reynolds P.H.S. (ED). 1999, CAB1 Publishing, Wallingford, U.K., pp. 169-186.
Gans S. et al., "Inhibition of Leaf Senescence by Autoregulated Production of Cytokinin," Science, vol. 270, 1995, pp. 1986-1988.
Smart C.M. et al., "Delayed Leaf Senescence in Tobacco Plants Transformed With tmr, a Gene for Cytokinin Production in Agrobacterium," The Plant Cell, vol. 3, No. 7, 1991, pp. 647-656.
Zhang J. et al., "Development of Flooding-tolerant *Arabidopsis thaliana* by Autoregulated Cytokinin Production," Molecular Breeding, vol. 6, No. 2, 2000, pp. 135-144.
Kranz H.D. et al., "Towards functional characterisation of the members of the R2R3-MYB gene family from *Arabidopsis thaliana*," The Plant Journal (1998) vol. 16, No. 2, pp. 236-276, Blackwell Science Ltd., Oxford, GB.
Song Feng Li, et al., "A novel myb-related gene from *Arabidopsis thaliana*," Febs Letters, Elsevier, Amsterdam, NL, vol. 379, Jan. 1, 1996, pp. 117-121.
Yi Han Lin et al., "Organ-specific, developmentally-regulated and abiotic stress-induced activities of four *Arabidopsis thaliana* promoters in transgenic white clover (*Trifolium repens* L.)," Plant Science, Elsevier Ireland Ltd., J. Plant Sci. 2003-08-011, vol. 165, No. 6, Dec. 1, 2003, pp. 1437-1444.
Sidorenko L.V. et al., "Complex structure of a maize Myb gene promoter: functional analysis in transgenic plants," The Plant Journal, vol. 22, No. 6, Jun. 2000, pp. 471-482.
Agriculture Victoria Services Pty Ltd. et al., Supplementary European Search Report issued on corresponding European Patent Application No. 08733383.7 on Jun. 1, 2010, 9 pages.
Extended European Search Report mailed Mar. 29, 2012, issued in corresponding European Patent Application No. 12153159.4, filed Apr. 21, 2008, 8 pages.

*Primary Examiner* — Medina A Ibrahim
(74) *Attorney, Agent, or Firm* — Christensen O'Connor Johnson Kindness PLLC

(57) ABSTRACT

The present invention relates to methods of manipulating senescence in plants. The invention also relates to vectors useful in such methods, transformed plants with modified senescence characteristics and plant cells, seeds and other parts of such plants.

23 Claims, 65 Drawing Sheets

```
  1 gtttgtgtct tctagattaa tcctccaaac ttttgattaa ccaaaaaaat tatcaaacta
 61 acatgttctc cttttttctt tagaaattct aacgaattta tctttatact gatttgaata
                                                    <<<   XcmI   >>>
121 tacttaattt ggtcatttgg atgcccttta caacctcctt accaaactca ctatggcaaa
181 tatatactat tttccattgt aacataaatg tccataattt gaattaaatt cgttgcagta
241 cgaaaccatc caactttgtc caaaaacaaa atccttataa ctatttactt taatgtaaat
301 atatcctcta cttttgtttt tacaaccota gctcaaacaa atttattatt tgcgataaaa
361 aatcatatcg aacaaactcg atgatttttt ttttcttacg ttattaatga aactaaaata
421 tagaaaaaaa caagatgaac caaattttca cctatctaac tacttaaata taatatgatt
                                                   < SspI>
481 aaatttggta agtttgaaa agtttcttta gaaatgtgaa atattgatca cagtttctat
541 tgctaaaatc accaacaaaa cgcatgtcgc cattcataat tatggtttca cacctacaac
601 taggctaata agtaaataag tagacaacta gactcaggtt tgaaaaaacc ataaaagcca
661 tatagcgttt tctcattgaa actgcgaaca cgatcgtgtg aatgttgcag tttctagttt
721 tgatacaaac aaacaaaaac acaatttaat cttagattaa aaagaaaaaa gagaacggag
781 cccactagcc actccttcaa acgtgtctta ccaactctct tctagaaaca aattaggctt
841 caccttcctc ttccaacctc tctctctctc tctctctctt tttctcaaac catctctcca
901 taaagcccta atttcttcat cacaagaatc agaagaagaa a
```

Figure 1.

```
  1  gtttgtgtct tctagattaa tcctccaaac ttttgattaa ccaaaaaaat tatcaaacta
 61  acatgttctc ctttttctt tagaaattct aacgaattta tctttatact gatttgaata
121  tacttaattt ggtcatttgg atgccctta caacctcctt accaaactca ttgatcacag
181  tttctattgc taaaatcacc aacaaaacgc atgtcgccat tcataattat ggtttcacac
241  ctacaactag gctaataagt aaataagtag acaactagac tcaggtttga aaaaaccata
301  aaagccatat agcgttttct cattgaaact gcgaacacga tcgtgtgaat gttgcagttt
361  ctagttttga tacaaacaaa caaaaacaca atttaatctt agattaaaaa gaaaaaagag
421  aacggagccc actagccact ccttcaaacg tgtcttacca actctcttct agaaacaaat
481  taggcttcac cttcctcttc caacctctct ctctctctct ctctttttt ctcaaaccat
541  ctctccataa agccctaatt tcttcatcac aagaatcaga agaagaaa
```

Figure 2.

```
  1 tacttaattt ggtcatttgg atgcccttta caacctcctt accaaactca ttgatcacag
 61 tttctattgc taaaatcacc aacaaaacgc atgtcgccat tcataattat ggtttcacac
121 ctacaactag gctaataagt aaataagtag acaactagac tcaggtttga aaaaaccata
181 aaagccatat agcgttttct cattgaaact gcgaacacga tcgtgtgaat gttgcagttt
241 ctagttttga tacaaacaaa caaaaacaca atttaatctt agattaaaaa gaaaaaagag
301 aacggagccc actagccact ccttcaaacg tgtcttacca actctcttct agaaacaaat
361 taggcttcac cttcctctt c caacc tctct ctctctctct ctctcttttt ctcaaaccat
421 ctctccataa agccctaatt tcttcatcac aagaatcaga agaagaaa
```

Figure 3.

```
  1 attgatcaca gtttctattg ctaaaatcac caacaaaacg catgtcgcca ttcataatta
 61 tggtttcaca cctacaacta ggctaataag taaataagta gacaactaga ctcaggtttg
121 aaaaaaccat aaaagccata tagcgttttc tcattgaaac tgcgaacacg atcgtgtgaa
181 tgttgcagtt tctagttttg atacaaacaa acaaaaacac aatttaatct tagattaaaa
241 agaaaaaaga gaacggagcc cactagccac tccttcaaac gtgtcttacc aactctcttc
301 tagaaacaaa ttaggcttca ccttcctctt ccaacctctc tctctctctc tctctctttt
361 tctcaaacca tctctccata aagccctaat ttcttcatca caagaatcag aagaagaaa
```

Figure 4.

```
  1 atggacctgc atctaatttt cggtccaact tgcacaggaa agacgacgac cgcgatagct
 61 cttgcccagc agacagggct tccagtcctt tcgcttgatc gggtccaatg ctgtcctcaa
121 ctatcaaccg gaagcggacg accaacagtg gaagaactga aggaacgac gcgtctctac
181 cttgatgatc ggcctctggt ggagggtatc atcgcagcca agcaagctca tcataggctg
241 atcgaggagg tgtataatca tgaggccaac ggcgggctta ttcttgaggg aggatccacc
301 tcgttgctca actgcatggc gcgaaacagc tattggagtg cagattttcg ttggcatatt
361 attcgccaca agttacccga ccaagagacc ttcatgaaag cggccaaggc cagagttaag
421 cagatgttgc accccgctgc aggccattct attattcaag agttggttta tctttggaat
481 gaacctcggc tgaggcccat tctgaaagag atcgatggat atcgatatgc catgttgttt
541 gctagccaga accagatcac ggcagatatg ctattgcagc ttgacgcaaa tatggaaggt
601 aagttgatta atgggatcgc tcaggagtat ttcatccatg cgcgccaaca ggaacagaaa
661 ttcccccaag ttaacgcagc cgctttcgac ggattcgaag gtcatccgtt cggaatgtat
721 tag
```

Figure 6.

```
  1 MDLHLIFGPT CTGKTTTAIA LAQQTGLPVL SLDRVQCCPQ LSTGSGRPTV EELKGTTRLY
 61 LDDRPLVEGI IAAKQAHHRL IEEVYNHEAN GGLILEGGST SLLNCMARNS YWSADFRWHI
121 IRHKLPDQET FMKAAKARVK QMLHPAAGHS IIQELVYLWN EPRLRPILKE IDGYRYAMLF
181 ASQNQITADM LLQLDANMEG KLINGIAQEY FIHARQQEQK FPQVNAAAFD GFEGHPFGMY
241 *
```

Figure 7

```
  1 atgtccatct caatgctaat gtgcagacta agacaaccct taataaacgt tccctgcagt
 61 ggcaaaaaac tgagcatgag gcagattcaa aaggagaagg tagtgttggt gatgggagct
121 acagggacag gaaagtcaaa gctctccatt gacctcgcca cctgtttccc ctcagaaatc
181 atcaactccg acaagattca aatctacgac ggcctcgaca tcgtcaccaa caaaatctcc
241 aaggaagaac aacgtggaat cccccaccac ctcctcggaa ctcaaaaccc taacacagac
301 ttcaccgccg gcgatttcag tgactgttcc accgccgcca ttgacgcaat cacaagccgc
361 gaccaccttc cgatcatcgc cggaggttcg aactcctacc tggaggcgtt aatcgacgac
421 gacgactaca aattccgatc gaggtacgac ttctgctgcc tctgggtcga cgtggcaatg
481 ccggtgctgg actcatacgt ggcggcgcgt gtggatcaga tgctccggag cggaatggtg
541 gaggagctga ccgttttt caacgcgaac ggcgactact cgagaggaat cagaagagcg
601 attggggttc ctgaattcga cgagtatttc cggcgggaag ggttcgccga tgaggaaacg
661 aggaaattgt tactggagcg agcggtgagg gagatgaagg tgaacacgtg caagctcgcg
721 aggaggcaat tggggaagat tcagaggctg aggaatgtga agaggtggga gattcaccgt
781 gttgatgcga cgccggtgtt ttggaagcgt ggggaggagg ctgatgaggc gtggcggaag
841 gtggtggcag agcctagtgc tatgatcgta gcgcagtttc tgtataaggc aaagagtgat
901 gtgaatgttg tttctggcgg tttcagagtg ccggcgggtt caacggagag tgttatggcg
961 gcggcgacgt gttag
```

Figure 8.

```
  1 MSISMLMCRL RQPLINVPCS GKKLSMRQIQ KEKVVLVMGA TGTGKSKLSI DLATCFPSEI
 61 INSDKIQIYD GLDIVTNKIS KEEQRGIPHH LLGTQNPNTD FTAGDFSDCS TAAIDAITSR
121 DHLPIIAGGS NSYLEALIDD DDYKFRSRYD FCCLWVDVAM PVLDSYVAAR VDQMLRSGMV
181 EELRPFFNAN GDYSRGIRRA IGVPEFDEYF RREGFADEET RKLLLERAVR EMKVNTCKLA
241 RRQLGKIQRL RNVKRWEIHR VDATPVFWKR GEEADEAWRK VVAEPSAMIV AQFLYKAKSD
301 VNVVSGGFRV PAGSTESVMA AATC*
```

Figure 9.

```
   1 atgttaattg tagtacatat tattagcatc acacgcatca tattcatcac cttacccat
  61 aatcatctcc atttccttat gtttagatca ttatcataca atcacaagca cctcaaattc
 121 cttacaaacc cgaccacacg ggtactccga agaaacatgt cgtcatccac tgtagtaaca
 181 atacccggcc ccacacaaaa aaacaaaaac aaaatcatag taataatggg tgcaacaggt
 241 tcaggaaaat caaaactctc aatagacctc gtcacacgtc actatccttt ttccgaaatc
 301 attaactccg acaaaatcca attaccaaa ggtttaaaca taaccacaaa caaaatcact
 361 gtacccgacc gacgtggcgt agttcatcat ttactcggcg agattgaccc cgactttaac
 421 ttttctcctt ctcatttccg gtcaattgct ggtcaacgca ttaactccat tattaatcgc
 481 cataaactcc cattcctcgt tggtgggtcc aactcatata tctacgcttt attaacaaac
 541 cggttcgacc cggattttaa ccctgattca acccggttc attttatatc caacgagtta
 601 cgctacaact gttgttttat ttgggtcgat gtattaaacc cggttttgaa tgagtatttg
 661 gataaacggg tcgatgagat gatgaactcg ggtatgtatg aagaactgga acagttttt
 721 aaagaaaaca ggttttcgga tccgggtttg gaaccgggtc gggccaccgg gttgaggaaa
 781 gcgataggg  taccggaaat ggagaggtat tttaagaaga gctgtacgta tgaggaagca
 841 gtgagggaaa taaaagaaaa cacgtggcgg ttagcgaaga agcagatgtg aagatccaa
 901 cggttgagag aagcagggtg ggacctacaa agagtagatg ccacggaggc atttgtggag
 961 gcgatgagta ataagaagga aaagggaatt atttgggaaa aacaagtagt ggaaccaagt
1021 gtcaagattg tgaaccgttt tttgttggac tga
```

Figure 10.

```
  1 MLIVVHIISI TRIIFITLTH NHLHFLMFRS LSYNHKHLKF LTNPTTRVLR RNMSSSTVVT
 61 IPGPTQKNKN KIIVIMGATG SGKSKLSIDL VTRHYPFSEI INSDKIQITK GLNITTNKIT
121 VPDRRGVVHH LLGEIDPDFN FSPSHFRSIA GQRINSIINR HKLPFLVGGS NSYIYALLTN
181 RFDPDFNPDS NPVHFISNEL RYNCCFIWVD VLNPVLNEYL DKRVDEMMNS GMYEELEQFF
241 KENRFSDPGL EPGRATGLRK AIGVPEMERY FKKSCTYEEA VREIKENTWR LAKKQMWKIQ
301 RLREAGWDLQ RVDATEAFVE AMSNKKEKGI IWEKQVVEPS VKIVNRFLLD *
```

Figure 11.

```
   1 gtcccgtatc acgcagcgcg tgagctaccc aggcactgcc gccgccggca caaccgttct
  61 tgaatcagaa cccgagggcg acgctgcccg cgaggtccag gcgctggccg ctgaaattaa
 121 atcaaaactc atttgagtta atgaggtaaa gagaaaatga gcaaaagcac aaacacgcta
 181 agtgccggcc gtccgagcgc acgcagcagc aaggctgcaa cgttggccag cctggcagac
 241 acgccagcca tgaagcgggt caactttcag ttgccggcgg aggatcacac caagctgaag
 301 atgtacgcgg tacgccaagg caagaccatt accgagctgc tatctgaata catcgcgcag
 361 ctaccagagt aaatgagcaa atgaataaat gagtagatga attttagcgg ctaaaggagg
 421 cggcatggaa aatcaagaac aaccaggcac cgacgccgtg aatgccca tgtgtggagg
 481 aacgggcggt tggccaggcg taagcggctg ggttgtctgc cggccctgca atggcactgg
 541 aaccccaag cccgaggaat cggcgtgacg gtcgcaaacc atccggcccg gtacaaatcg
 601 gcgcggcgct gggtgatgac ctggtggaga agttgaaggc cgcgcaggcc gccagcggc
 661 aacgcatcga ggcagaagca cgccccggtg aatcgtggca agcggccgct gatcgaatcc
 721 gcaaagaatc ccggcaaccg ccggcagccg gtgcgccgtc gattaggaag ccgcccaagg
 781 gcgacgagca accagatttt ttcgttccga tgctctatga cgtgggcacc cgcgatagtc
 841 gcagcatcat ggacgtggcc gttttccgtc tgtcgaagcg tgaccgacga gctggcgagg
 901 tgatccgcta cgagcttcca gacgggcacg tagaggtttc gcagggccg gccggcatgg
 961 ccagtgtgtg ggattacgac ctggtactga tggcggtttc ccatctaacc gaatccatga
1021 accgataccg ggaagggaag ggagacaagc ccggccgcgt gttccgtcca cacgttgcgg
1081 acgtactcaa gttctgccgg cgagccgatg gcggaaagca gaaagacgac ctggtagaaa
1141 cctgcattcg gttaaacacc acgcacgttg ccatgcagcg tacgaagaag gccaagaacg
1201 gccgcctggt gacggtatcc gagggtgaag ccttgattag ccgctacaag atcgtaaaga
1261 gcgaaaccgg gcggccggag tacatcgaga tcgagctagc tgattggatg taccgcgaga
1321 tcacagaagg caagaacccg gacgtgctga cggttcaccc cgattacttt ttgatcgatc
1381 ccggcatcgg ccgtttctc taccgcctgg cacgccgcgc cgcaggcaag gcagaagcca
1441 gatggttgtt caagacgatc tacgaacgca gtggcagcgc cggagagttc aagaagttct
1501 gtttcaccgt gcgcaagctg atcgggtcaa atgacctgcc ggagtacgat ttgaaggagg
1561 aggcggggca ggctggcccg atcctagtca tgcgctaccg caacctgatc gagggcgaag
1621 catccgccgg ttcctaatgt acggagcaga tgctagggca aattgcccta gcaggggaaa
1681 aaggtcgaaa aggtctcttt cctgtggata gcacgtacat tgggaaccca aagccgtaca
1741 ttgggaaccg gaacccgtac attgggaacc caaagccgta cattgggaac cggtcacaca
1801 tgtaagtgac tgatataaaa gagaaaaaag gcgattttc gcctaaaac tctttaaaac
1861 ttattaaaac tcttaaaacc cgcctggcct gtgcataact gtctgccag cgcacagccg
1921 aagagctgca aaaagcgcct acccttcggt cgctgcgctc cctacgcccc gccgcttcgc
1981 gtcggcctat cgcggccgct ggccgctcaa aaatggctgg cctacggcca ggcaatctac
2041 cagggcgcgg acaagccgcg ccgtcgccac tcgaccgccg gcgcccacat caaggcaccc
2101 tgcctcgcgc gtttcggtga tgacggtgaa aacctctgac acatgcagct cccgagacg
2161 gtcacagctt gtctgtaagc ggatgccggg agcagacaag cccgtcaggg cgcgtcagcg
2221 ggtgttggcg ggtgtcgggg cgcagccatg acccagtcac gtagcgatag cggagtgtat
2281 actggcttaa ctatgcggca tcagagcaga ttgtactgag agtgcaccat atgcggtgtg
2341 aaataccgca cagatgcgta aggagaaaat accgcatcag gcgctcttcc gcttcctcgc
2401 tcactgactc gctgcgctcg gtcgttcggc tgcggcgagc ggtatcagct cactcaaagg
2461 cggtaatacg gttatccaca gaatcagggg ataacgcagg aagaacatg tgagcaaaag
2521 gccagcaaaa ggccaggaac cgtaaaaagg ccgcgttgct ggcgtttttc cataggctcc
2581 gcccccctga cgagcatcac aaaaatcgac gctcaagtca gaggtggcga aacccgacag
2641 gactataaag ataccaggcg tttccccctg gaagctccct cgtgcgctct cctgttccga
2701 ccctgccgct taccggatac ctgtccgcct ttctcccttc gggaagcgtg gcgctttctc
2761 atagctcacg ctgtaggtat ctcagttcgg tgtaggtcgt tcgctccaag ctgggctgtg
2821 tgcacgaacc cccgttcag cccgaccgct gcgccttatc cggtaactat cgtcttgagt
2881 ccaacccggt aagacacgac ttatcgccac tggcagcagc cactggtaac aggattagca 2941 gagcgaggta tgtaggcggt gctacagagt tcttgaagtg gtggcctaac tacggctaca
3001 ctagaaggac agtatttggt atctgcgctc tgctgaagcc agttaccttc ggaaaaagag
```

Figure 17.

```
3061 ttggtagctc ttgatccggc aaacaaacca ccgctggtag cggtggtttt tttgtttgca
3121 agcagcagat tacgcgcaga aaaaaaggat ctcaagaaga tcctttgatc ttttctacgg
3181 ggtctgacgc tcagtggaac gaaaactcac gttaagggat tttggtcatg catgatatat
3241 ctcccaattt gtgtagggct tattatgcac gcttaaaaat aataaaagca gacttgacct
3301 gatagtttgg ctgtgagcaa ttatgtgctt agtgcatcta atcgcttgag ttaacgccgg
3361 cgaagcggcg tcggcttgaa cgaattccta gctagacatt atttgccgac taccttggtg
3421 atctcgcctt tcacgtagtg gacaaattct tccaactgat ctgcgcgcga ggccaagcga
3481 tcttcttctt gtccaagata agcctgtcta gcttcaagta tgacgggctg atactgggcc
3541 ggcaggcgct ccattgccca gtcggcagcg acatccttcg gcgcgatttt gccggttact
3601 gcgctgtacc aaatgcggga caacgtaagc actacatttc gctcatcgcc agcccagtcg
3661 ggcggcgagt tccatagcgt taaggtttca tttagcgcct caaatagatc ctgttcagga
3721 accggatcaa agagttcctc cgccgctgga cctaccaagg caacgctatg ttctcttgct
3781 tttgtcagca agatagccga atcaatgtcg atcgtggctg gctcgaagat acctgcaaga
3841 atgtcattgc gctgccattc tccaaattgc agttcgcgct tagctggata acgcacgga
3901 atgatgtcgt cgtgcacaac aatggtgact tctacagcgc ggagaatctc gctctctcca
3961 ggggaagccg aagtttccaa aaggtcgttg atcaaagctc gccgcgttgt tcatcaagc
4021 cttacgtca ccgtaaccag caaatcaata tcactgtgtg gcttcaggcc gccatccact
4081 gcggagccgt acaaatgtac ggccagcaac gtcggttcga gatggcgctc gatgacgcca
4141 actacctctg atagttgagt cgatacttcg gcgatcaccg cttcccccat gatgtttaac
4201 tttgttttag ggcgactgcc ctgctgcgta acatcgttgc tgctccataa catcaaacat
4261 cgacccacgg cgtaacgcgc ttgctgcttg gatgcccgag gcatagactg taccccaaaa
4321 aaacatgtca taacaagaag ccatgaaaac cgccactgcg ccgttaccac cgctgcgttc
4381 ggtcaaggtt ctggaccagt tgcctgacgg cagttacgct acttgcatta cagcttacga
4441 accgaacgag gcttatgtcc actgggttcg tgcccgaatt gatcacaggc agcaacgctc
4501 tgtcatcgtt acaatcaaca tgctaccctc cgcgagatca tccgtgtttc aaacccggca
4561 gcttagttgc cgttcttccg aatagcatcg gtaacatgag caaagtctgc cgccttacaa
4621 cggctctccc gctgacgccg tcccggactg atgggctgcc tgtatcgagt ggtgattttg
4681 tgccgagctg ccggtcgggg agctgttggc tggctggtgg caggatatat tgtggtgtaa
4741 acaaattgac gcttagacaa cttaataaca cattgcggac gttttaatg tactgaatta
4801 acgccgaatt gaattcctcg agtacgtagg atccatttaa attctagagg cgcgccgata
4861 tcctctctta aggtagcgag ctcttaatta atagggataa cagggtaatg cggccgcaag
4921 ctaaaacgac ggccagtgaa ttatcaactt gtatagaaa agttgctctg ccgacagtgg
4981 tcccaaagat ggaccccac ccacgaggag catcgtggaa aaagaagacg ttccaaccac
5041 gtcttcaaag caagtggatt gatgtgataa catggtggag cacgacactc tcgtctactc
5101 caagaatatc aaagatacag tctcagaaga ccaaagggct attgagactt tcaacaaag
5161 ggtaatatcg ggaaacctcc tcggattcca ttgcccagct atctgtcact tcatcaaaag
5221 gacagtagaa aaggaaggtg gcacctacaa atgccatcat tgcgataaag gaaaggctat
5281 cgttcaagat gcctctgccg acagtggtcc caaagatgga ccccaccca cgaggagcat
5341 cgtggaaaaa gaagacgttc caaccacgtc ttcaaagcaa gtggattgat gtgatatctc
5401 cactgacgta agggatgacg cacaatccca ctatccttcg caagacccct tctctatata
5461 aggaagttca tttcatttgg agaggacacg ctgcaagttt gtacaaaaaa gcaggctatg
5521 gcaattacct tatccgcaac ttcttttacct atttccgccc ggatccgggc aggttctccg
5581 gccgcttggg tggagaggct attcggctat gactgggcac aacagacaat cggctgctct
5641 gatgccgccg tgttccggct gtcagcgcag gggcgcccgg ttcttttgt caagaccgac
5701 ctgtccggtg ccctgaatga actgcaggac gaggcagcgc ggctatcgtg gctggccacg
5761 acgggcgttc cttgcgcagc tgtgctcgac gttgtcactg aagcgggaag ggactggctg
5821 ctattgggcg aagtgccggg gcaggatctc ctgtcatctc accttgctcc tgccgagaaa 5881 gtatccatca tggctgatgc aatgcggcgg ctgcatacgc ttgatccggc tacctgccca
5941 ttcgaccacc aagcgaaaca tcgcatcgag cgagcacgta ctcggatgga gccggtctt
6001 gtcgatcagg atgatctgga cgaagagcat caggggctcg cgccagccga actgttcgcc
6061 aggctcaagg cgcgcatgcc cgacgcgag gatctcgtcg tgacccatgg cgatgcctgc
6121 ttgccgaata tcatggtgga aaatggccgc ttttctggat tcatcgactg tggccggctg
```

Figure 17.
(Cont.)

```
6181 ggtgtggcgg accgctatca ggacatagcg ttggctaccc gtgatattgc tgaagagctt
6241 ggcggcgaat gggctgaccg cttcctcgtg ctttacggta tcgccgctcc cgattcgcag
6301 cgcatcgcct tctatcgcct tcttgacgag ttcttctgaa cccagctttc ttgtacaaag
6361 tggagtccgc aaaaatcacc agtctctctc tacaaatcta tctctctcta tttttctcca
6421 gaataatgtg tgagtagttc ccagataagg gaattagggt tcttataggg tttcgctcat
6481 gtgttgagca tataagaaac ccttagtatg tatttgtatt tgtaaaatac ttctatcaat
6541 aaaatttcta attcctaaaa ccaaaatcca gtgacctcaa ctttattata catagttgat
6601 aattcactgg ccgtgcttat tccatggctg caggtcgacg aattcaccgg ttagggataa
6661 cagggtaatc gctaccttag gaccgttata gttacggcca gtgccattac cctgttatcc
6721 ctaaccggtg acaactttgt atagaaaagt tggtttgtgt cttctagatt aatcctccaa
6781 actttgatt aaccaaaaaa attatcaaac taacatgttc tccttttttc tttagaaatt
6841 ctaacgaatt tatctttata ctgatttgaa tatacttaat ttggtcattt ggatgccctt
6901 tacaacctcc ttaccaaact cactatggca aatatatact attttccatt gtaacataaa
6961 tgtccataat ttgaattaaa ttcgttgcag tacgaaacca tccaactttg tccaaaaaca
7021 aaatccttat aactatttac tttaatgtaa atatatcctc tactttgtt tttacaaccc
7081 tagctcaaac aaatttatta ttgcgataa aaaatcatat cgaacaaact cgatgatttt
7141 ttttttctta cgttattaat gaaactaaaa tatagaaaaa aacaagatga accaaatttt
7201 cacctatcta actacttaaa tataatatga ttaaatttgg taaagtttga aagtttctt
7261 tagaaatgtg aaatattgat cacagtttct attgctaaaa tcaccaacaa aacgcatgtc
7321 gccattcata attatggttt cacacctaca actaggctaa taagtaaata agtagacaac
7381 tagactcagg tttgaaaaaa ccataaaagc catatagcgt tttctcattg aaactgcgaa
7441 cacgatcgtg tgaatgttgc agtttctagt tttgatacaa acaaacaaaa acacaattta
7501 atcttagatt aaaaagaaaa aagagaacgg agcccactag ccactccttc aaacgtgtct
7561 taccaactct cttctagaaa caaattaggc ttcaccttcc tcttccaacc tctctctctc
7621 tctctctctc tttttctcaa accatctctc cataaagccc taatttcttc atcacaagaa
7681 tcagaagaag aaacaagttt gtacaaaaaa gcaggcttac tgcaaaaaac ttatggacct
7741 gcatctaatt ttcggtccaa cttgcacagg aaagacgacg accgcgatag ctcttgccca
7801 gcagacaggg cttccagtcc tttcgcttga tcgggtccaa tgctgtcctc aactatcaac
7861 cggaagcgga cgaccaacag tggaagaact gaaaggaacg acgcgtctct accttgatga
7921 tcggcctctg gtggagggta tcatcgcagc caagcaagct catcataggc tgatcgagga
7981 ggtgtataat catgaggcca acggcgggct tattcttgag ggaggatcca cctcgttgct
8041 caactgcatg gcgcgaaaca gctattggag tgcagatttt cgttggcata ttattcgcca
8101 caagttaccc gaccaagaga ccttcatgaa agcggccaag gccagagtta agcagatgtt
8161 gcaccccgct gcaggccatt ctattattca agagttggtt tatctttgga atgaacctcg
8221 gctgaggccc attctgaaag agatcgatgg atatcgatat gccatgttgt ttgctagcca
8281 gaaccagatc acggcagata tgctattgca gcttgacgca aatatggaag gtaagttgat
8341 taatgggatc gctcaggagt atttcatcca tgcgcgccaa caggaacaga aattcccca
8401 agttaacgca gccgctttcg acggattcga aggtcatccg ttcggaatgt attaggtacc
8461 cagctttctt gtacaaagtg ggatcgttca aacatttggc aataaagttt cttaagattg
8521 aatcctgttg ccggtcttgc gatgattatc atataatttc tgttgaatta cgttaagcat
8581 gtaataatta acatgtaatg catgacgtta tttatgagat gggtttttat gattagagtc
8641 ccgcaattat acatttaata cgcgatagaa aacaaaatat agcgcgcaaa ctaggataaa
8701 ttatcgcgcg cggtgtcatc tatgttacta gatccaactt tattatacat agttgattcg
8761 tcgacctgca gtcgctacct taggaccgtt atagtttatgg caaacagcta ttatgggtat
```

Figure 17.
(Cont.)

```
8821 tatgggtggt tctttatgcg gacactgacg gctttatgcc tgcaggtcgc gagcgatcgc
8881 ggtaccgccc gggcgtcgac aggcctaagc ttagcttgag cttggatcag attgtcgttt
8941 cccgccttca gtttaaacta tcagtgtttg acaggatata ttggcgggta aacctaagag
9001 aaaagagcgt ttattagaat aacggatatt taaaagggcg tgaaaaggtt tatccgttcg
9061 tccatttgta tgtgcatgcc aaccacaggg ttcccctcgg gatcaaagta ctttgatcca
9121 acccctccgc tgctatagtg cagtcggctt ctgacgttca gtgcagccgt cttctgaaaa
9181 cgacatgtcg cacaagtcct aagttacgcg acaggctgcc gccctgccct tttcctggcg
9241 ttttcttgtc gcgtgtttta gtcgcataaa gtagaatact tgcgactaga accggagaca
9301 ttacgccatg aacaagagcg ccgccgctgg cctgctgggc tatgcccgcg tcagcaccga
9361 cgaccaggac ttgaccaacc aacgggccga actgcacgcg gccggctgca ccaagctgtt
9421 ttccgagaag atcaccggca ccaggcgcga ccgccggag ctggccagga tgcttgacca
9481 cctacgccct ggcgacgttg tgacagtgac caggctagac cgcctggccc gcagcacccg
9541 cgacctactg gacattgccg agcgcatcca ggaggccggc gcgggcctgc gtagcctggc
9601 agagccgtgg gccgacacca ccacgccggc cggccgcatg gtgttgaccg tgttcgccgg
9661 cattgccgag ttcgagcgtt ccctaatcat cgaccgcacc cggagcgggc gcgaggccgc
9721 caaggcccga ggcgtgaagt ttggcccccg ccctaccctc acccggcac agatcgcgca
9781 cgcccgcgag ctgatcgacc aggaaggccg caccgtgaaa gaggcggctg cactgcttgg
9841 cgtgcatcgc tcgaccctgt accgcgcact tgagcgcagc gaggaagtga cgcccaccga
9901 ggccaggcgg cgcggtgcct tccgtgagga cgcattgacc gaggccgacg ccctggcggc
9961 cgccgagaat gaacgccaag aggaacaagc atgaaaccgc accaggacgg ccaggacgaa
10021 ccgtttttca ttaccgaaga gatcgaggcg gagatgatcg cggccgggta cgtgttcgag
10081 ccgcccgcgc acgtctcaac cgtgcggctg catgaaatcc tggccggttt gtctgatgcc
10141 aagctggcgg cctggccggc cagcttggcc gctgaagaaa ccgagcgccg ccgtctaaaa
10201 aggtgatgtg tatttgagta aaacagcttg cgtcatgcgg tcgctgcgta tatgatcga
10261 tgagtaaata aacaaatacg caaggggaac gcatgaaggt tatcgctgta cttaaccaga
10321 aaggcgggtc aggcaagacg accatcgcaa cccatctagc ccgcgccctg caactcgccg
10381 gggccgatgt tctgttagtc gattccgatc cccagggcag tgcccgcgat tgggcggccg
10441 tgcgggaaga tcaaccgcta accgttgtcg gcatcgaccg cccgacgatt gaccgcgacg
10501 tgaaggccat cggccggcgc gacttcgtag tgatcgacgg agcgcccag gcggcggact
10561 tggctgtgtc cgcgatcaag gcagccgact tcgtgctgat tccggtgcag ccaagcccttt
10621 acgacatatg gccaccgcc gacctggtgg agctggttaa gcagcgcatt gaggtcacgg
10681 atggaaggct acaagcggcc tttgtcgtgt cgcgggcgat caaaggcacg cgcatcggcg
10741 gtgaggttgc cgaggcgctg gccgggtacg agctgcccat tcttga
```

Figure 17.
(Cont.)

```
   1 gtcccgtatc acgcagcgcg tgagctaccc aggcactgcc gccgccggca caaccgttct
  61 tgaatcagaa cccgagggcg acgctgcccg cgaggtccag gcgctggccg ctgaaattaa
 121 atcaaaactc atttgagtta atgaggtaaa gagaaaatga gcaaaagcac aaacacgcta
 181 agtgccggcc gtccgagcgc acgcagcagc aaggctgcaa cgttggccag cctggcagac
 241 acgccagcca tgaagcgggt caactttcag ttgccggcgg aggatcacac caagctgaag
 301 atgtacgcgg tacgccaagg caagaccatt accgagctgc tatctgaata catcgcgcag
 361 ctaccagagt aaatgagcaa atgaataaat gagtagatga attttagcgg ctaaaggagg
 421 cggcatggaa aatcaagaac aaccaggcac cgacgccgtg aatgccccca tgtgtggagg
 481 aacgggcggt tggccaggcg taagcggctg ggttgtctgc cggccctgca atggcactgg
 541 aaccccaag cccgaggaat cggcgtgacg gtcgcaaacc atccggcccg gtacaaatcg
 601 gcgcggcgct gggtgatgac ctggtggaga agttgaaggc cgcgcaggcc gcccagcggc
 661 aacgcatcga ggcagaagca cgcccggtg aatcgtggca agcggccgct gatcgaatcc
 721 gcaaagaatc ccggcaaccg ccggcagccg gtgcgccgtc gattaggaag ccgcccaagg
 781 gcgacgagca accagatttt ttcgttccga tgctctatga cgtgggcacc cgcgatagtc
 841 gcagcatcat ggacgtggcc gttttccgtc tgtcgaagcg tgaccgacga gctggcgagg
 901 tgatccgcta cgagcttcca gacgggcacg tagaggtttc cgcagggccg gccggcatgg
 961 ccagtgtgtg ggattacgac ctggtactga tggcggtttc ccatctaacc gaatccatga
1021 accgataccg ggaagggaag ggagacaagc ccggccgcgt gttccgtcca cacgttgcgg
1081 acgtactcaa gttctgccgg cgagccgatg gcggaaagca gaaagacgac ctggtagaaa
1141 cctgcattcg gttaaacacc acgcacgttg ccatgcagcg tacgaagaag gccaagaacg
1201 gccgcctggt gacggtatcc gagggtgaag ccttgattag ccgctacaag atcgtaaaga
1261 gcgaaaccgg gcggccggag tacatcgaga tcgagctagc tgattggatg taccgcgaga
1321 tcacagaagg caagaacccg gacgtgctga cggttcaccc cgattacttt ttgatcgatc
1381 ccggcatcgg ccgtttttctc taccgcctgg cacgccgcgc cgcaggcaag gcagaagcca
1441 gatggttgtt caagacgatc tacgaacgca gtggcagcgc cggagagttc aagaagttct
1501 gtttcaccgt gcgcaagctg atcggtcaa atgacctgcc ggagtacgat ttgaaggagg
1561 aggcggggca ggctggcccg atcctagtca tgcgctaccg caacctgatc gagggcgaag
1621 catccgccgg ttcctaatgt acgagcaga tgctaggca aattgcccta gcaggggaaa
1681 aaggtcgaaa aggtctcttt cctgtggata gcacgtacat tgggaaccca aagccgtaca
1741 ttgggaaccg gaacccgtac attgggaacc caaagccgta cattgggaac cggtcacaca
1801 tgtaagtgac tgatatraaa gagaaaaaag gcgattttc cgcctaaaac tctttaaaac
1861 ttattaaaac tcttaaaacc cgcctggcct gtgcataact gtctggccag cgcacagccg
1921 aagagctgca aaaagcgcct accttcggt cgctgcgctc cctacgcccc gccgcttcgc
1981 gtcggcctat cgcggccgct ggccgctcaa aaatggctgg cctacggcca ggcaatctac
2041 cagggcgcg acaagccgcg ccgtcgccac tcgaccgccg gcgcccacat caaggcaccc
2101 tgcctcgcgc gtttcggtga tgacggtgaa aacctctgac acatgcagct cccggagacg
2161 gtcacagctt gtctgtaagc ggatgccggg agcagacaag cccgtcaggg cgcgtcagcg
2221 ggtgttggcg ggtgtcgggg cgcagccatg acccagtcac gtagcgatag cggagtgtat
2281 actggcttaa ctatgcggca tcagagcaga ttgtactgag agtgcaccat atgcggtgtg
2341 aaataccgca cagatgcgta aggagaaaat accgcatcag cgctcttcc gcttcctcgc
2401 tcactgactc gctgcgctcg gtcgttcggc tgcggcgagc ggtatcagct cactcaaagg
2461 cggtaatacg gttatccaca gaatcagggg ataacgcagg aaagaacatg tgagcaaaag
2521 gccagcaaaa ggccaggaac cgtaaaaagg ccgcgttgct ggcgtttttc cataggctcc
2581 gcccccctga cgagcatcac aaaaatcgac gctcaagtca gaggtggcga acccgacag
2641 gactataaag ataccaggcg tttccccctg gaagctccct cgtgcgctct cctgttccga
2701 ccctgccgct taccggatac ctgtccgcct ttctcccttc gggaagcgtg gcgctttctc
2761 atagctcacg ctgtaggtat ctcagttcgg tgtaggtcgt tcgctccaag ctgggctgtg
2821 tgcacgaacc cccgttcag cccgaccgct gcgccttatc cggtaactat cgtcttgagt
2881 ccaacccggt aagacacgac ttatcgccac tggcagcagc cactggtaac aggattagca
2941 gagcgaggta tgtaggcggt gctacagagt tcttgaagtg gtggcctaac tacggctaca
3001 ctagaaggac agtatttggt atctgcgctc tgctgaagcc agttaccttc ggaaaaagag
```

Figure 19.

```
3061 ttggtagctc ttgatccggc aaacaaacca ccgctggtag cggtggtttt tttgtttgca
3121 agcagcagat tacgcgcaga aaaaaaggat ctcaagaaga tcctttgatc ttttctacgg
3181 ggtctgacgc tcagtggaac gaaaactcac gttaagggat tttggtcatg catgatatat
3241 ctcccaattt gtgtagggct tattatgcac gcttaaaaat aataaaagca gacttgacct
3301 gatagtttgg ctgtgagcaa ttatgtgctt agtgcatcta atcgcttgag ttaacgccgg
3361 cgaagcggcg tcggcttgaa cgaatttcta gctagacatt atttgccgac taccttggtg
3421 atctcgcctt tcacgtagtg gacaaattct tccaactgat ctgcgcgcga ggccaagcga
3481 tcttcttctt gtccaagata agcctgtcta gcttcaagta tgacgggctg atactgggcc
3541 ggcaggcgct ccattgccca gtcggcagcg acatccttcg gcgcgatttt gccggttact
3601 gcgctgtacc aaatgcggga caacgtaagc actacatttc gctcatcgcc agcccagtcg
3661 ggcggcgagt tccatagcgt taaggtttca tttagcgcct caaatagatc ctgttcagga
3721 accggatcaa agagttcctc cgccgctgga cctaccaagg caacgctatg ttctcttgct
3781 tttgtcagca agatagccag atcaatgtcg atcgtggctg gctcgaagat acctgcaaga
3841 atgtcattgc gctgccattc tccaaattgc agttcgcgct tagctggata acgccacgga
3901 atgatgtcgt cgtgcacaac aatggtgact tctacagcgc ggagaatctc gctctctcca
3961 ggggaagccg aagtttccaa aaggtcgttg atcaaagctc gccgcgttgt ttcatcaagc
4021 cttacggtca ccgtaaccag caaatcaata tcactgtgtg gcttcaggcc gccatccact
4081 gcggagccgt acaaatgtac ggccagcaac gtcggttcga gatggcgctc gatgacgcca
4141 actacctctg atagttgagt cgatacttcg gcgatcaccg cttcccccat gatgtttaac
4201 tttgttttag ggcgactgcc ctgctgcgta acatcgttgc tgctccataa catcaaacat
4261 cgacccacgg cgtaacgcgc ttgctgcttg gatgcccgag gcatagactg taccccaaaa
4321 aaacatgtca taacaagaag ccatgaaaac cgccactgcg ccgttaccac cgctgcgttc
4381 ggtcaaggtt ctggaccagt tgcgtgacgg cagttacgct acttgcatta cagcttacga
4441 accgaacgag gcttatgtcc actgggttcg tgcccgaatt gatcacagge agcaacgctc
4501 tgtcatcgtt acaatcaaca tgctaccctc cgcgagatca tccgtgtttc aaacccggca
4561 gcttagttgc cgttcttccg aatagcatcg gtaacatgag caaagtctgc cgccttacaa
4621 cggctctccc gctgacgccg tccggactg atgggctgcc tgtatcgagt ggtgattttg
4681 tgccgagctg ccggtcgggg agctgttggc tggctggtgg caggatatat tgtggtgtaa
4741 acaaattgac gcttagacaa cttaataaca cattgcggac gttttaatg tactgaatta
4801 acgccgaatt gaattcctcg agtacgtagg atccatttaa attctagagg cgcgccgata
4861 tcctctctta aggtagcgag ctcttaatta atagggataa cagggtaatg cggccgcaag
4921 ctaaaacgac ggccagtgaa ttatcaactt tgtatagaaa agttgctctg ccgacagtgg
4981 tcccaaagat ggaccccac ccacgaggag catcgtgaa aaagaagacg ttccaaccac
5041 gtcttcaaag caagtggatt gatgtgataa catggtgag cacgacactc tgtctactc
5101 caagaatatc aaagatacag tctcagaaga ccaaagggct attgagactt tcaacaaag
5161 ggtaatatcg ggaaacctcc tcggattcca ttgcccagct atctgtcact tcatcaaaag
5221 gacagtagaa aaggaaggtg gcacctacaa atgccatcat tgcgataaag gaaaggctat
5281 cgttcaagat gcctctgccg acagtggtcc caaagatgga cccccaccca cgaggagcat
5341 cgtgaaaaa gaagacgttc caaccacgtc ttcaaagcaa gtggattgat gtgatatctc
5401 cactgacgta agggatgacg cacaatccca ctatccttcg caagacccett cctctatata
5461 aggaagttca tttcatttgg agaggacacg ctgcaagttt gtacaaaaaa gcaggctatg
5521 gcaattacct tatccgcaac ttctttacct atttccgcc ggatccggga aggttctccg
5581 gccgcttggg tggagaggct attcggctat gactgggcac aacagacaat cggctgctct
5641 gatgccgccg tgttccggct gtcagcgcag gggcgcccgg ttcttttgt caagaccgac
5701 ctgtccggtg ccctgaatga actgcaggac gaggcagcgc ggctatcgtg gctggccacg
5761 acgggcgttc cttgcgcagc tgtgctcgac gttgtcactg aagcgggaag ggactggctg
5821 ctattgggcg aagtgccggg gcaggatctc ctgtcatctc accttgctcc tgccgagaaa
5881 gtatccatca tggctgatgc aatgcggcgg ctgcatacgc ttgatccggc tacctgccca
5941 ttcgaccacc aagcgaaaca tcgcatcgag cgagcacgta ctcggatgga gccggtctt
6001 gtcgatcagg atgatctgga cgaagagcat caggggctcg cgccagccga actgttcgcc
6061 aggctcaagg cgcgcatgcc cgacgcgag gatctcgtcg tgacccatgg cgatgcctgc
6121 ttgccgaata tcatggtgga aaatggccgc ttttctggat tcatcgactg tggccggctg
```

Figure 19.
(Cont.)

```
6181 ggtgtggcgg accgctatca ggacatagcg ttggctaccc gtgatattgc tgaagagctt
6241 ggcggcgaat gggctgaccg cttcctcgtg ctttacggta tcgccgctcc cgattcgcag
6301 cgcatcgcct tctatcgcct tcttgacgag ttcttctgaa ccagctttc ttgtacaaag
6361 tggagtccgc aaaaatcacc agtctctctc tacaaatcta tctctctcta ttttttctcca
6421 gaataatgtg tgagtagttc ccagataagg gaattagggt tcttataggg tttcgctcat
6481 gtgttgagca tataagaaac ccttagtatg tatttgtatt tgtaaaatac ttctatcaat
6541 aaaatttcta attcctaaaa ccaaaatcca gtgacctcaa ctttattata catagttgat
6601 aattcactgg ccgtgcttat tccatggctg caggtcgacg aattcaccgg ttagggataa
6661 cagggtaata actataacgg tcctaaggta gcgagcggcc gcaagctaaa acgacggcca
6721 gtgaattatc aactttgtat agaaaagttg gtttgtgtct tctagattaa tcctccaaac
6781 ttttgattaa ccaaaaaaat tatcaaacta acatgttctc cttttttctt tagaaattct
6841 aacgaattta tctttatact gatttgaata tacttaattt ggtcatttgg atgcccttta
6901 caacctcctt accaaaatat tgatcacagt ttctattgct aaaatcacca acaaaacgca
6961 tgtcgccatt cataattatg gtttcacacc tacaactagg ctaataagta aataagtaga
7021 caactagact caggtttgaa aaaccataa aagccatata gcgttttctc attgaaactg
7081 cgaacacgat cgtgtgaatg ttgcagtttc tagttttgat acaaacaaac aaaaacacaa
7141 tttaatctta gattaaaaag aaaaaagaga acggagccca ctagccactc cttcaaacgt
7201 gtcttaccaa ctctcttcta gaaacaaatt aggcttcacc ttcctcttcc aacctctctc
7261 tctctctctc tctctctttc tcaaaccatc tctccataaa gcctaatttt cttcatcaca
7321 agaatcagaa gaagaaacaa gtttgtacaa aaaagcaggc ttactgcaaa aaacttatgg
7381 acctgcatct aattttcggt ccaacttgca caggaaagac gacgaccgcg atagctcttg
7441 cccagcagac agggcttcca gtcctttcgc ttgatcgggt ccaatgctgt cctcaactat
7501 caaccggaag cggacgacca acagtggaag aactgaaagg aacgacgcgc ctctaccttg
7561 atgatcggcc tctggtggag ggtatcatcg cagccaagca agctcatcat aggctgatcg
7621 aggaggtgta taatcatgag gccaacggcg ggcttattct tgagggagga tccacctcgt
7681 tgctcaactg catggcgcga aacagctatt ggagtgcaga ttttcgttgg catattattc
7741 gccacaagtt acccgaccaa gagaccttca tgaaagcggc caaggccaga gttaagcaga
7801 tgttgcaccc cgctgcaggc cattctatta ttcaagagtt ggtttatctt tggaatgaac
7861 ctcggctgag gcccattctg aaagagatcg atggatatcg atatgccatg ttgtttgcta
7921 gccagaacca gatcacggca gatatgctat tgcagcttga cgcaaatatg gaaggtaagt
7981 tgattaatgg gatcgctcag gagtatttca tccatgcgcg ccaacaggaa cagaaattcc
8041 cccaagttaa cgcagccgct ttcgacggat tcgaaggtca tccgttcgga atgtattagg
8101 tacccagctt tcttgtacaa agtgggatcg ttcaaacatt tggcaataaa gtttcttaag
8161 attgaatcct gttgccggtc ttgcgatgat tatcatataa tttctgttga attacgttaa
8221 gcatgtaata attaacatgt aatgcatgac gttatttatg agatgggttt ttatgattag
8281 agtcccgcaa ttatacattt aatacgcgat agaaacaaa atatagcgcg caaactagga
8341 taaattatcg cgcgcggtgt catctatgtt actagatcca acttattat acatagttga
8401 taattcactg gccgtcgctt attccatggc tgcaggtcga cgaattcacc ggttaactat
8461 aacggtccta aggtagcgat ggcaaacagc tattatgggt attatgggtg gttctttatg
8521 cggacactga cggctttatg cctgcaggtc gcgagcgatc gcggtaccgc ccgggcgtcg
8581 acaggcctaa gctagcttg agcttggatc agattgtcgt ttccgcctt cagtttaaac
8641 tatcagtgtt tgacaggata tattggcggg taaacctaag agaaagagc gttattaga
8701 ataacggata tttaaaaggg cgtgaaagg tttatccgtt cgtccatttg tatgtgcatg
8761 ccaaccacag ggtcccctc gggatcaaag tactttgatc caaccccctcc gctgctatag
8821 tgcagtcggc ttctgacgtt cagtgcagcc gtcttctgaa aacgacatgt cgcacaagtc
8881 ctaagttacg cgacaggctg ccgccctgcc cttttcctgg cgtttttcttt tcgcgtgttt
8941 tagtcgcata agtgaaata cttgcgacta gaaccggaga cattacgcca tgaacaagag
9001 cgccgccgct ggcctgctgg gctatgcccg cgtcagcacc gacgaccagg acttgaccaa
9061 ccaacgggcc gaactgcacg cggccggctg caccaagctg ttttccgaga gatcaccgg
9121 caccaggcgc gaccgccgg agctggcag gatgcttgac cacctacgcc ctggcgacgt
9181 tgtgacagtg accaggctag accgcctggc cgcagcacc cgcgacctac tggacattgc
9241 cgagcgcatc caggaggccg gcgcgggcct gctgtagcctg gcagagccgt gggccgacac
```

Figure 19.
(Cont.)

```
9301 caccacgccg gccggccgca tggtgttgac cgtgttcgcc ggcattgccg agttcgagcg
9361 ttccctaatc atcgaccgca cccggagcgg gcgcgaggcc gccaaggccc gaggcgtgaa
9421 gtttggcccc cgccctaccc tcaccccggc acagatcgcg cacgcccgcg agctgatcga
9481 ccaggaaggc cgcaccgtga agaggcggc tgcactgctt ggcgtgcatc gctcgaccct
9541 gtaccgcgca cttgagcgca gcgaggaagt gacgcccacc gaggccaggc ggcgcggtgc
9601 cttccgtgag gacgcattga ccgaggccga cgccctggcg gccgccgaga atgaacgcca
9661 agaggaacaa gcatgaaacc gcaccaggac ggccaggacg aaccgttttt cattaccgaa
9721 gagatcgagg cggagatgat cgcggccggg tacgtgttcg agccgcccgc gcacgtctca
9781 accgtgcggc tgcatgaaat cctggccggt ttgtctgatg ccaagctggc ggcctggccg
9841 gccagcttgg ccgctgaaga aaccgagcgc cgccgtctaa aaaggtgatg tgtatttgag
9901 taaaacagct tgcgtcatgc ggtcgctgcg tatatgatgc gatgagtaaa taaacaaata
9961 cgcaagggga acgcatgaag gttatcgctg tacttaacca gaaaggcggg tcaggcaaga
10021 cgaccatcgc aacccatcta gcccgcgccc tgcaactcgc cggggccgat gttctgttag
10081 tcgattccga tccccagggc agtgcccgcg attgggcggc cgtgcgggaa gatcaaccgc
10141 taaccgttgt cggcatcgac cgcccgacga ttgaccgcga cgtgaaggcc atcggccggc
10201 gcgacttcgt agtgatcgac ggagcgcccc aggcggcgga cttggctgtg tccgcgatca
10261 aggcagccga cttcgtgctg attccggtgc agccaagccc ttacgacata tgggccaccg
10321 ccgacctggt ggagctggtt aagcagcgca ttgaggtcac ggatggaagg ctacaagcgg
10381 cctttgtcgt gtcgcgggcg atcaaaggca cgcgcatcgg cggtgaggtt gccgaggcgc
10441 tggccgggta cgagctgccc attcttga
```

Figure 19.
(Cont.)

```
   1 gtcccgtatc acgcagcgcg tgagctaccc aggcactgcc gccgccggca caaccgttct
  61 tgaatcagaa cccgagggcg acgctgcccg cgaggtccag gcgctggccg ctgaaattaa
 121 atcaaaactc atttgagtta atgaggtaaa gagaaaatga gcaaaagcac aaacacgcta
 181 agtgccggcc gtccgagcgc acgcagcagc aaggctgcaa cgttggccag cctggcagac
 241 acgccagcca tgaagcgggt caactttcag ttgccggcgg aggatcacac caagctgaag
 301 atgtacgcgg tacgccaagg caagaccatt accgagctgc tatctgaata catcgcgcag
 361 ctaccagagt aaatgagcaa atgaataaat gagtagatga atttagcgg ctaaaggagg
 421 cggcatggaa aatcaagaac aaccaggcac cgacgccgtg aatgccccca tgtgtggagg
 481 aacgggcggt tggccaggcg taagcggctg ggttgtctgc cggccctgca atggcactgg
 541 aaccccaag cccgaggaat cggcgtgacg gtcgcaaacc atcggcccg gtacaaatcg
 601 gcgcggcgct gggtgatgac ctggtggaga agttgaaggc cgcgcaggcc gcccagcggc
 661 aacgcatcga ggcagaagca cgccccggtg aatcgtggca agcggccgct gatcgaatcc
 721 gcaaagaatc ccggcaaccg ccggcagccg gtgcgccgtc gattaggaag ccgcccaagg
 781 gcgacgagca accagatttt ttcgttccga tgctctatga cgtgggcacc cgcgatagtc
 841 gcagcatcat ggacgtggcc gttttccgtc tgtcgaagcg tgaccgacga gctggcgagg
 901 tgatccgcta cgagcttcca gacgggcacg tagaggtttc cgcagggccg gccggcatgg
 961 ccagtgtgtg ggattacgac ctggtactga tggcggtttc ccatctaacc gaatccatga
1021 accgatacccg ggaagggaag ggagacaagc ccggccgcgt gttccgtcca cacgttgcgg
1081 acgtactcaa gttctgccgg cgagccgatg gcggaaagca gaaagacgac ctggtagaaa
1141 cctgcattcg gttaaacacc acgcacgttg ccatgcagcg tacgaagaag gccaagaacg
1201 gccgcctggt gacggtatcc gagggtgaag ccttgattag ccgctacaag atcgtaaaga
1261 gcgaaaccgg gcggccggag tacatcgaga tcgagctagc tgattggatg taccgcgaga
1321 tcacagaagg caagaacccg gacgtgctga cggttcaccc cgattacttt ttgatcgatc
1381 ccggcatcgg ccgttttctc taccgcctgg cacgccgcgc gcaggcaag cagaagcca
1441 gatggttgtt caagacgatc tacgaacgca gtggcagcgc cggagagttc aagaagttct
1501 gtttcaccgt gcgcaagctg atcgggtcaa atgacctgcc ggagtacgat ttgaaggagg
1561 aggcggggca ggctggcccg atcctagtca tgcgctaccg caacctgatc gagggcgaag
1621 catccgccgg ttcctaatgt acggagcaga tgctagggca aattgcccta gcagggggaaa
1681 aaggtcgaaa aggtctcttt cctgtggata gcacgtacat tgggaaccca aagccgtaca
1741 ttgggaaccg gaacccgtac attgggaacc caagccgta cattgggaac cggtcacaca
1801 tgtaagtgac tgatataaaa gagaaaaaag gcgatttttc cgcctaaaac tctttaaaac
1861 ttattaaaac tcttaaaacc cgcctggcct gtgcataact gtctggccag cgcacagccg
1921 aagagctgca aaaagcgcct acccttcggt cgctgcgctc cctacgcccc gccgcttcgc
1981 gtcggcctat cgcggccgct ggccgctcaa aaatggctgg cctacggcca ggcaatctac
2041 cagggcgcgg acaagccgcg ccgtcgccac tcgaccgccg gcgcccacat caaggcaccc
2101 tgcctcgcgc gtttcggtga tgacggtgaa aacctctgac acatgcagct cccggagacg
2161 gtcacagctt gtctgtaagc ggatgccggg agcagacaag cccgtcaggg cgcgtcagcg
2221 ggtgttggcg ggtgtcgggg cgcagccatg acccagtcac gtagcgatag cggagtgtat
2281 actgcttaa ctatgcggca tcagagcaga ttgtactgag agtgcaccat atgcggtgtg
2341 aaataccgca cagatgcgta aggagaaaat accgcatcag gcgctcttcc gcttcctcgc
2401 tcactgactc gctgcgctcg tcgttcggc tgcggcgagc ggtatcagct cactcaaagg
2461 cggtaatacg gttatccaca gaatcagggg ataacgcagg aaagaacatg tgagcaaaag
2521 gccagcaaaa ggccaggaac cgtaaaaagg ccgcgttgct ggcgtttttc cataggctcc
2581 gcccccctga cgagcatcac aaaaatcgac gctcaagtca gaggtggcga acccgacag
2641 gactataaag ataccaggcg tttccccctg gaagctccct cgtgcgctct cctgttccga
2701 ccctgccgct taccggatac ctgtccgcct ttctcccttc gggaagcgtg gcgctttctc
2761 atagctcacg ctgtaggtat ctcagttcgg tgtaggtcgt tcgctccaag ctgggctgtg
2821 tgcacgaacc ccccgttcag cccgaccgct gcgccttatc cggtaactat cgtcttgagt
```

Figure 21.

```
2881  ccaacccggt aagacacgac ttatcgccac tggcagcagc cactggtaac aggattagca
2941  gagcgaggta tgtaggcggt gctacagagt tcttgaagtg gtggcctaac tacggctaca
3001  ctagaaggac agtatttggt atctgcgctc tgctgaagcc agttaccttc ggaaaaagag
3061  ttggtagctc ttgatccggc aaacaaacca ccgctggtag cggtggtttt tttgtttgca
3121  agcagcagat tacgcgcaga aaaaaaggat ctcaagaaga tcctttgatc ttttctacgg
3181  ggtctgacgc tcagtggaac gaaaactcac gttaagggat tttggtcatg catgatatat
3241  ctcccaattt gtgtagggct tattatgcac gcttaaaaat aataaaagca gacttgacct
3301  gatagtttgg ctgtgagcaa ttatgtgctt agtgcatcta atcgcttgag ttaacgccgg
3361  cgaagcggcg tcggcttgaa cgaatttcta gctagacatt atttgccgac taccttggtg
3421  atctcgcctt tcacgtagtg acaaattct ccaactgat ctgcgcgcga ggccaagcga
3481  tcttcttctt gtccaagata agcctgtcta gcttcaagta tgacgggctg atactgggcc
3541  ggcaggcgct ccattgccca gtcggcagcg acatccttcg gcgcgatttt gccggttact
3601  gcgctgtacc aaatgcggga caacgtaagc actacatttc gctcatcgcc agcccagtcg
3661  ggcggcgagt tccatagcgt taaggtttca tttagcgcct caaatagatc ctgttcagga
3721  accggatcaa agagttcctc cgccgctgga cctaccaagg caacgctatg ttctcttgct
3781  tttgtcagca agatagccag atcaatgtcg atcgtggctg gctcgaagat acctgcaaga
3841  atgtcattgc gctgccattc tccaaattgc agttcgcgct tagctggata acgccacgga
3901  atgatgtcgt cgtgcacaac aatggtgact tctacagcgc ggagaatctc gctctctcca
3961  ggggaagccg aagtttccaa aaggtcgttg atcaaagctc gccgcgttgt ttcatcaagc
4021  cttacggtca ccgtaaccag caaatcaata tcactgtgtg gcttcaggcc gccatccact
4081  gcggagccgt acaaatgtac ggccagcaac gtcggttcga gatggcgctc gatgacgcca
4141  actacctctg atagttgagt cgatacttcg gcgatcaccg cttcccccat gatgtttaac
4201  tttgttttag ggcgactgcc ctgctgcgta acatcgttgc tgctccataa catcaaacat
4261  cgacccacgg cgtaacgcgc ttgctgcttg gatgcccgag gcatagactg taccccaaaa
4321  aaacatgtca taacaagaag ccatgaaaac cgccactgcg ccgttaccac cgctgcgttc
4381  ggtcaaggtt ctggaccagt tgcgtgacgg cagttacgct acttgcatta cagcttacga
4441  accgaacgag gcttatgtcc actgggttcg tgcccgaatt gatcacaggc agcaacgctc
4501  tgtcatcgtt acaatcaaca tgctaccctc cgcgagatca tccgtgtttc aaacccggca
4561  gcttagttgc cgttcttccg aatagcatcg gtaacatgag caaagtctgc cgccttacaa
4621  cggctctccc gctgacgccg tccggactg atgggctgcc tgtatcgagt ggtgattttg
4681  tgccgagctg ccggtcgggg agctgttggc tggctggtgg caggatatat tgtggtgtaa
4741  acaaattgac gcttagacaa cttaataaca cattgcggac gttttaatg tactgaatta
4801  acgccgaatt gaattcctcg agtacgtagg atccatttaa attctagagg cgcgccgata
4861  tcctctctta aggtagcgag ctcttaatta atagggataa cagggtaatg cggccgcaag
4921  ctaaaacgac ggccagtgaa ttatcaactt tgtatagaaa agttgctctg ccgacagtgg
4981  tcccaaagat ggacccccac ccacgaggag catcgtggaa aagaagacg ttccaaccac
5041  gtcttcaaag caagtggatt gatgtgataa catggtggag cacgacactc tcgtctactc
5101  caagaatatc aaagatacag tctcagaaga ccaaagggct attgagactt ttcaacaaag
5161  ggtaatatcg ggaaacctcc tcggattcca ttgcccagct atctgtcact tcatcaaaag
5221  gacagtagaa aaggaaggtg gcacctacaa atgccatcat tgcgataaag gaaaggctat
5281  cgttcaagat gcctctgccg acagtggtcc caaagatgga cccccaccca cgaggagcat
5341  cgtggaaaaa gaagacgttc caaccacgtc ttcaaagcaa gtggattgat gtgatatctc
5401  cactgacgta agggatgacg cacaatccca ctatccttcg caagaccctt cctctatata
5461  aggaagttca tttcatttgg agaggacacg ctgcaagttt gtacaaaaaa gcaggctaga
5521  ccggggggca atgagatatg aaaaagcctg aactcaccgc gacgtctgtc gagaagtttc
5581  tgatcgaaaa gttcgacagc gtctccgacc tgatgcagct ctcggagggc gaagaatctc
5641  gtgctttcag cttcgatgta ggagggcgtg gatatgtcct gcgggtaaat agctgcgccg
5701  atggtttcta caaagatcgt tatgtttatc ggcactttgc atcggccgcg ctcccgattc
5761  cggaagtgct tgacattggg gaattcagcg agagcctgac ctattgcatc tcccgccgtg
```

Figure 21.
(Cont.)

```
5821 cacagggtgt cacgttgcaa gacctgcctg aaaccgaact gcccgctgtt ctgcagccgg
5881 tcgcggaggc catggatgcg atcgctgcgg ccgatcttag ccagacgagc gggttcggcc
5941 cattcggacc gcaaggaatc ggtcaataca ctacatggcg tgatttcata tgcgcgattg
6001 ctgatcccca tgtgtatcac tggcaaactg tgatggacga caccgtcagt gcgtccgtcg
6061 cgcaggctct cgatgagctg atgctttggg ccgaggactg ccccgaagtc cggcacctcg
6121 tgcacgcgga tttcggctcc aacaatgtcc tgacggacaa tggccgcata acagcggtca
6181 ttgactggag cgaggcgatg ttcggggatt cccaatacga ggtcgccaac atcttcttct
6241 ggaggccgtg gttggcttgt atggagcagc agacgcgcta cttcgagcgg aggcatccgg
6301 agcttgcagg atcgccgcgc ctccgggcgt atatgctccg cattggtctt gaccaactct
6361 atcagagctt ggttgacggc aatttcgatg atgcagcttg ggcgcagggt cgatgcgacg
6421 caatcgtccg atccggagcc gggactgtcg ggcgtacaca aatcgcccgc agaagcgcgg
6481 ccggccgtct ggaccgatgg ctgtgtagaa gtactcgccg atagtggaaa ccgacgcccc
6541 agcactcgtc cggacccagc tttcttgtac aaagtggagt ccgcaaaaat caccagtctc
6601 tctctacaaa tctatctctc tctattttc tccagaataa tgtgtgagta gttcccagat
6661 aagggaatta gggttcttat agggtttcgc tcatgtgttg agcatataag aaacccttag
6721 tatgtatttg tatttgtaaa atacttctat caataaaatt tctaattcct aaaaccaaaa
6781 tccagtgacc tcaactttat tatacatagt tgataattca ctggccgtgc ttattccatg
6841 gctgcaggtc gacgaattca ccggtaggg ataacagggt aatcgctacc ttaggaccgt
6901 tatagttacg gccagtgcca ttaccctgtt atccctaacc ggtgacaact ttgtatagaa
6961 aagttggttt gtgtcttcta gattaatcct ccaaactttt gattaaccaa aaaaattatc
7021 aaactaacat gttctccttt tttctttaga aattctaacg aatttatctt tatactgatt
7081 tgaatatact taatttggtc atttggatgc cctttacaac ctccttacca aactcactat
7141 ggcaaatata tactattttc cattgtaaca taaatgtcca taatttgaat taaattcgtt
7201 gcagtacgaa accatccaac tttgtccaaa aacaaaatcc ttataactat ttactttaat
7261 gtaaatatat cctctacttt tgttttaca acccctagctc aaacaaattt attatttgcg
7321 ataaaaaatc atatcgaaca aactcgatga ttttttttt cttacgttat taatgaaact
7381 aaaatataga aaaaaacaag atgaaccaaa ttttcaccta tctaactact taaatataat
7441 atgattaaat ttggtaaagt ttgaaaagtt tctttagaaa tgtgaaatat tgatcacagt
7501 ttctattgct aaaatcacca acaaaacgca tgtcgccatt cataattatg gtttcacacc
7561 tacaactagg ctaataagta aataagtaga caactagact caggtttgaa aaaaccataa
7621 aagccatata gcgtttttctc attgaaactg cgaacacgat cgtgtgaatg ttgcagtttc
7681 tagttttgat acaaacaaac aaaaacacaa tttaatctta gattaaaaag aaaaaagaga
7741 acggagccca ctagccactc cttcaaacgt gtcttaccaa ctctcttcta gaaacaaatt
7801 aggcttcacc ttcctcttcc aacctctctc tctctctctc tctcttttc tcaaaccatc
7861 tctccataaa gcctaatt cttcatcaca agaatcagaa gaagaaacaa gtttgtacaa
7921 aaaagcaggc ttactgcaaa aaacttatgg acctgcatct aattttcggt ccaacttgca
7981 caggaaagac gacgaccgcg atagctcttg cccagcagac agggcttcca gtcctttcgc
8041 ttgatcgggt ccaatgctgt cctcaactat caaccggaag cggacgacca acagtggaag
8101 aactgaaagg aacgacgcgt ctctaccttg atgatcggcc tctggtggag ggtatcatcg
8161 cagccaagca agctcatcat aggctgatcg aggaggtgta taatcatgag gccaacggcg
8221 ggcttattct tgagggagga tccacctcgt tgctcaactg catggcgcga acagctatt
8281 ggagtgcaga ttttcgttgg catattattc gccacaagtt acccgaccaa gagaccttca
8341 tgaaagcggc caaggccaga gttaagcaga tgttgcaccc cgctgcaggc cattctatta
8401 ttcaagagtt ggtttatctt tggaatgaac ctcggctgag gcccattctg aaagagatcg
8461 atggatatcg atatgccatg ttgtttgcta gccagaacca gatcacggca gatatgctat
8521 tgcagcttga cgcaaatatg gaaggtaagt tgattaatgg gatcgctcag gagtatttca
8581 tccatgcgcg ccaacaggaa cagaaattcc cccaagttaa cgcagccgct ttcgacggat
8641 tcgaaggtca tccgttcgga atgtattagg tacccagctt tcttgtacaa agtgggatcg
8701 ttcaaacatt tggcaataaa gtttcttaag attgaatcct gttgccggtc ttgcgatgat
```

Figure 21.
(Cont.)

```
8761 tatcatataa tttctgttga attacgttaa gcatgtaata attaacatgt aatgcatgac
8821 gttatttatg agatgggttt ttatgattag agtcccgcaa ttatacattt aatacgcgat
8881 agaaaacaaa atatagcgcg caaactagga taaattatcg cgcgcggtgt catctatgtt
8941 actagatcca actttattat acatagttga ttcgtcgacc tgcagtcgct accttaggac
9001 cgttatagtt atggcaaaca gctattatgg gtattatggg tggttcttta tgcggacact
9061 gacggcttta tgcctgcagg tcgcgagcga tcgcggtacc gcccgggcgt cgacaggcct
9121 aagcttagct tgagcttgga tcagattgtc gtttcccgcc ttcagtttaa actatcagtg
9181 tttgacagga tatattggcg ggtaaaccta agagaaaaga gcgtttatta gaataacgga
9241 tatttaaaag ggcgtgaaaa ggtttatccg ttcgtccatt tgtatgtgca tgccaaccac
9301 agggttcccc tcgggatcaa agtactttga tccaacccct ccgctgctat agtgcagtcg
9361 gcttctgacg ttcagtgcag ccgtcttctg aaaacgacat gtcgcacaag tcctaagtta
9421 cgcgacaggc tgccgccctg ccctttttcct ggcgttttct tgtcgcgtgt tttagtcgca
9481 taaagtagaa tacttgcgac tagaaccgga gacattacgc catgaacaag agcgccgccg
9541 ctggcctgct gggctatgcc cgcgtcagca ccgacgacca ggacttgacc aaccaacggg
9601 ccgaactgca cgcggccggc tgcaccaagc tgttttccga gaagatcacc ggcaccaggc
9661 gcgaccgccc ggagctggcc aggatgcttg accacctacg ccctggcgac gttgtgacag
9721 tgaccaggct agaccgcctg gcccgcagca cccgcgacct actggacatt gccgagcgca
9781 tccaggaggc cggcgcgggc ctgcgtagcc tggcagagcc gtgggccgac accaccacgc
9841 cggccggccg catggtgttg accgtgttcg ccggcattgc cgagttcgag cgttccctaa
9901 tcatcgaccg cacccggagc gggcgcgagg ccgccaaggc ccgaggcgtg aagtttggcc
9961 cccgccctac cctcacccg gcacagatcg cgcacgcccg cgagctgatc gaccaggaag
10021 gccgcaccgt gaaagaggcg gctgcactgc ttggcgtgca tcgctcgacc ctgtaccgcg
10081 cacttgagcg cagcgaggaa gtgacgccca ccgaggccag gcggcgcggt gccttccgtg
10141 aggacgcatt gaccgaggcc gacgccctgg cggccgccga gaatgaacgc caagaggaac
10201 aagcatgaaa ccgcaccagg acggccagga cgaaccgttt ttcattaccg aagagatcga
10261 ggcggagatg atcgcggccg ggtacgtgtt cgagccgccc gcgcacgtct caaccgtgcg
10321 gctgcatgaa atcctggccg gtttgtctga tgccaagctg gcggcctggc cggccagctt
10381 ggccgctgaa gaaaccgagc gccgccgtct aaaaaggtga tgtgtatttg agtaaaacag
10441 cttgcgtcat gcggtcgctg cgtatatgat gcgatgagta aataaacaaa tacgcaaggg
10501 gaacgcatga aggttatcgc tgtacttaac cagaaaggcg ggtcaggcaa gacgaccatc
10561 gcaacccatc tagcccgcgc cctgcaactc gccggggccg atgttctgtt agtcgattcc
10621 gatccccagg gcagtgcccg cgattgggcg gccgtgcggg aagatcaacc gctaaccgtt
10681 gtcggcatcg accgcccgac gattgaccgc gacgtgaagg ccatcggccg gcgcgacttc
10741 gtagtgatcg acggagcgcc ccaggcggcg gacttggctg tgtccgcgat caaggcagcc
10801 gacttcgtgc tgattccggt gcagccaagc ccttacgaca tatgggccac cgccgacctg
10861 gtggagctgg ttaagcagcg cattgaggtc acggatggaa ggctacaagc ggcctttgtc
10921 gtgtcgcggg cgatcaaagg cacgcgcatc ggcggtgagg ttgccgaggc gctggccggg
10981 tacgagctgc ccattcttga
```

Figure 21.
(Cont.)

```
   1 gtcccgtatc acgcagcgcg tgagctaccc aggcactgcc gccgccggca caaccgttct
  61 tgaatcagaa cccgagggcg acgctgcccg cgaggtccag gcgctggccg ctgaaattaa
 121 atcaaaactc atttgagtta atgaggtaaa gagaaaatga gcaaaagcac aaacacgcta
 181 agtgccggcc gtccgagcgc acgcagcagc aaggctgcaa cgttggccag cctggcagac
 241 acgccagcca tgaagcgggt caactttcag ttgccggcgg aggatcacac caagctgaag
 301 atgtacgcgg tacgccaagg caagaccatt accgagctgc tatctgaata catcgcgcag
 361 ctaccagagt aaatgagcaa atgaataaat gagtagatga attttagcgg ctaaaggagg
 421 cggcatggaa aatcaagaac aaccaggcac cgacgccgtg gaatgcccca tgtgtggagg
 481 aacgggcggt tggccaggcg taagcggctg ggttgtctgc cggccctgca atggcactgg
 541 aacccccaag cccgaggaat cggcgtgacg gtcgcaaacc atccggcccg gtacaaatcg
 601 gcgcggcgct gggtgatgac ctggtggaga agttgaaggc cgcgcaggcc gcccagcggc
 661 aacgcatcga ggcagaagca cgccccggtg aatcgtggca agcggccgct gatcgaatcc
 721 gcaaagaatc ccggcaaccg ccggcagccg gtgcgccgtc gattaggaag ccgcccaagg
 781 gcgacgagca accagatttt ttcgttccga tgctctatga cgtgggcacc cgcgatagtc
 841 gcagcatcat ggacgtggcc gttttccgtc tgtcgaagcg tgaccgacga gctggcgagg
 901 tgatccgcta cgagcttcca gacgggcacg tagaggtttc gcagggccg gccggcatgg
 961 ccagtgtgtg ggattacgac ctggtactga tggcggtttc ccatctaacc gaatccatga
1021 accgataccg ggaagggaag ggagacaagc ccggccgcgt gttccgtcca cacgttgcgg
1081 acgtactcaa gttctgccgg cgagccgatg gcggaaagca gaaagacgac ctggtagaaa
1141 cctgcattcg gttaaacacc acgcacgttg ccatgcagcg tacgaagaag gccaagaacg
1201 gccgcctggt gacggtatcc gagggtgaag ccttgattag ccgctacaag atcgtaaaga
1261 gcgaaaccgg gcggccggag tacatcgaga tcgagctagc tgattggatg taccgcgaga
1321 tcacagaagg caagaacccg gacgtgctga cggttcaccc cgattacttt ttgatcgatc
1381 ccggcatcgg ccgtttctc taccgcctgg cacgccgcgc gcaggcaag gcagaagcca
1441 gatggttgtt caagacgatc tacgaacgca gtggcagcgc cggagagttc aagaagttct
1501 gtttcaccgt gcgcaagctg atcgggtcaa atgacctgcc ggagtacgat ttgaaggagg
1561 aggcggggca ggctggcccg atcctagtca tgcgctaccg caacctgatc gagggcgaag
1621 catccgccgg ttcctaatgt acgagcaga tgctagggca aattgcccta gcaggggaaa
1681 aaggtcgaaa aggtctcttt cctgtggata gcacgtacat tgggaaccca aagccgtaca
1741 ttgggaaccg gaacccgtac attgggaacc caaagccgta cattgggaac cggtcacaca
1801 tgtaagtgac tgatatatat gagaaaaaag gcgattttc cgcctaaaac tctttaaaac
1861 ttattaaaac tcttaaaacc cgcctggcct gtgcataact gtctggccag cgcacagccg
1921 aagagctgca aaaagcgcct acccttcggt cgctgcgctc cctacgcccc gccgcttcgc
1981 gtcggcctat cgcggccgct ggccgctcaa aaatggctgg cctacggcca ggcaatctac
2041 cagggcgcgg acaagccgcg ccgtcgccac tgaccgcccg gcgcccacat caaggcaccc
2101 tgcctcgcgc gtttcggtga tgacggtgaa acctctgac acatgcagct cccggagacg
2161 gtcacagctt gtctgtaagc ggatgccggg agcagacaag cccgtcaggg cgcgtcagcg
2221 ggtgttggcg ggtgtcgggg cgcagccatg acccagtcac gtagcgatag cggagtgtat
2281 actggcttaa ctatgcggca tcagagcaga ttgtactgag agtgcaccat atgcggtgtg
2341 aaataccgca cagatgcgta aggagaaaat accgcatcag gcgctcttcc gcttcctcgc
2401 tcactgactc gctgcgctcg gtcgttcggc tgcggcgagc ggtatcagct cactcaaagg
2461 cggtaatacg gttatccaca gaatcagggg ataacgcagg aaagaacatg tgagcaaaag
2521 gccagcaaaa ggccaggaac cgtaaaaagg ccgcgttgct ggcgtttttc cataggctcc
2581 gcccccctga cgagcatcac aaaaatcgac gctcaagtca gaggtggcga aacccgacag
2641 gactataaag ataccaggcg tttccccctg gaagctccct cgtgcgctct cctgttccga
```

Figure 23.

```
2701 ccctgccgct taccggatac ctgtccgcct ttctcccttc gggaagcgtg gcgctttctc
2761 atagctcacg ctgtaggtat ctcagttcgg tgtaggtcgt tcgctccaag ctgggctgtg
2821 tgcacgaacc ccccgttcag cccgaccgct gcgccttatc cggtaactat cgtcttgagt
2881 ccaacccggt aagacacgac ttatcgccac tggcagcagc cactggtaac aggattagca
2941 gagcgaggta tgtaggcggt gctacagagt tcttgaagtg gtggcctaac tacggctaca
3001 ctagaaggac agtatttggt atctgcgctc tgctgaagcc agttaccttc ggaaaaagag
3061 ttggtagctc ttgatccggc aaacaaacca ccgctggtag cggtggtttt tttgtttgca
3121 agcagcagat tacgcgcaga aaaaaggat ctcaagaaga tcctttgatc ttttctacgg
3181 ggtctgacgc tcagtggaac gaaaactcac gttaagggat tttggtcatg catgatatat
3241 ctcccaattt gtgtagggct tattatgcac gcttaaaaat aataaaagca gacttgacct
3301 gatagtttgg ctgtgagcaa ttatgtgctt agtgcatcta atcgcttgag ttaacgccgg
3361 cgaagcggcg tcggcttgaa cgaatttcta gctagacatt atttgccgac taccttggtg
3421 atctcgcctt tcacgtagtg gacaaattct tccaactgat ctgcgcgcga ggccaagcga
3481 tcttcttctt gtccaagata agcctgtcta gcttcaagta tgacgggctg atactgggcc
3541 ggcaggcgct ccattgccca gtcggcagcg acatccttcg gcgcgatttt gccggttact
3601 gcgctgtacc aaatgcggga caacgtaagc actacatttc gctcatcgcc agcccagtcg
3661 ggcggcgagt tccatagcgt taaggtttca tttagcgcct caaatagatc ctgttcagga
3721 accggatcaa agagttcctc cgccgctgga cctaccaagg caacgctatg ttctcttgct
3781 tttgtcagca agatagccag atcaatgtcg atcgtggctg gctcgaagat acctgcaaga
3841 atgtcattgc gctgccattc tccaaattgc agttcgcgct tagctggata acgccacgga
3901 atgatgtcgt cgtgcacaac aatggtgact tctacagcgc ggagaatctc gctctctcca
3961 ggggaagccg aagtttccaa aaggtcgttg atcaaagctc gccgcgttgt ttcatcaagc
4021 cttacggtca ccgtaaccag caaatcaata tcactgtgtg gcttcaggcc gccatccact
4081 gcggagccgt acaaatgtac ggccagcaac gtcggttcga gatggcgctc gatgacgcca
4141 actacctctg atagttgagt cgatacttcg gcgatcaccg cttccccat gatgtttaac
4201 tttgttttag ggcgactgcc ctgctgcgta acatcgttgc tgctccataa catcaaacat
4261 cgacccacgg cgtaacgcgc ttgctgcttg gatgcccgag gcatagactg tacccccaaaa
4321 aaacatgtca taacaagaag ccatgaaaac cgccactgcg ccgttaccac cgctgcgttc
4381 ggtcaaggtt ctggaccagt tgcgtgacgg cagttacgct acttgcatta cagcttacga
4441 accgaacgag gcttatgtcc actgggttcg tgccgaatt gatcacaggc agcaacgctc
4501 tgtcatcgtt acaatcaaca tgctaccctc cgcgagatca tccgtgtttc aaacccggca
4561 gcttagttgc cgttcttccg aatagcatcg gtaacatgag caaagtctgc cgccttacaa
4621 cggctctccc gctgacgccg tcccggactg atgggctgcc tgtatcgagt ggtgattttg
4681 tgccgagctg ccggtcgggg agctgttggc tggctggtgg caggatatat tgtggtgtaa
4741 acaaattgac gcttagacaa cttaataaca cattgcggac gtttttaatg tactgaatta
4801 acgccgaatt gaattcctcg agtacgtagg atccatttaa attctagagg cgcgccgata
4861 tcctctctta aggtagcgag ctcttaatta atagggataa cagggtaatg cggccgcaag
4921 ctaaaacgac ggccagtgaa ttatcaactt tgtatagaaa agttgctctg ccgacagtgg
4981 tcccaaagat ggacccccac ccacgaggag catcgtggaa aaagaagacg ttccaaccac
5041 gtcttcaaag caagtggatt gatgtgataa catggtggag cacgacactc tgtctactc
5101 caagaatatc aaagatacag tctcagaaga ccaagggct attgagactt ttcaacaaag
5161 ggtaatatcg ggaaacctcc tcggattcca ttgcccagct atctgtcact tcatcaaaag
5221 gacagtagaa aaggaaggtg gcacctacaa atgccatcat tgcgataaag gaaaggctat
5281 cgttcaagat gcctctgccg acagtggtcc caaagatgga ccccacccca cgaggagcat
5341 cgtggaaaaa gaagacgttc caaccacgtc ttcaaagcaa gtggattgat gtgatatctc
```

Figure 23.
(Cont.)

```
5401 cactgacgta agggatgacg cacaatccca ctatccttcg caagacccct cctctatata
5461 aggaagttca tttcatttgg agaggacacg ctgcaagttt gtacaaaaaa gcaggctaga
5521 ccgggggca atgagatatg aaaaagcctg aactcaccgc gacgtctgtc gagaagtttc
5581 tgatcgaaaa gttcgacagc gtctccgacc tgatgcagct ctggagggc gaagaatctc
5641 gtgctttcag cttcgatgta ggagggcgtg gatatgtcct gcgggtaaat agctgcgccg
5701 atggtttcta caaagatcgt tatgtttatc ggcactttgc atcggccgcg ctcccgattc
5761 cggaagtgct tgacattggg gaattcagcg agagcctgac ctattgcatc tcccgccgtg
5821 cacagggtgt cacgttgcaa gacctgcctg aaaccgaact gcccgctgtt ctgcagccgg
5881 tcgcggaggc catggatgcg atcgctgcgg ccgatcttag ccagacgagc gggttcggcc
5941 cattcggacc gcaaggaatc ggtcaataca ctacatggcg tgatttcata tgcgcgattg
6001 ctgatcccca tgtgtatcac tggcaaactg tgatggacga caccgtcagt gcgtccgtcg
6061 cgcaggctct cgatgagctg atgctttggg ccgaggactg ccccgaagtc cggcacctcg
6121 tgcacgcgga tttccgctcc aacaatgtcc tgacgacaa tggccgcata acagcggtca
6181 ttgactggag cgaggcgatg ttcggggatt cccaatacga ggtcgccaac atcttcttct
6241 ggaggccgtg gttggcttgt atggagcagc agacgcgcta cttcgagcgg aggcatccgg
6301 agcttgcagg atcgccgcg ctccgggcgt atatgctccg cattggtctt gaccaactct
6361 atcagagctt ggttgacgga aatttcgatg atgcagcttg ggcgcagggt cgatgcgacg
6421 caatcgtccg atccggagcc gggactgtcg ggcgtacaca aatcgcccgc agaagcgcgg
6481 ccggccgtct ggaccgatgg ctgtgtagaa gtactcgccg atagtggaaa ccgacgcccc
6541 agcactcgtc cggacccagc tttcttgtac aaagtggagt ccgcaaaaat caccagtctc
6601 tctctacaaa tctatctctc tctattttt ccagaataa tgtgtgagta gttcccagat
6661 aagggaatta gggttcttat agggtttcgc tcatgtgttg agcatataag aaacccttag
6721 tatgtatttg tatttgtaaa atacttctat caataaaatt tctaattcct aaaaccaaaa
6781 tccagtgacc tcaactttat tatacatagt tgataattca ctggccgtgc ttattccatg
6841 gctgcaggtc gacgaattca ccggttaggg ataacagggt aataactata acggtcctaa
6901 ggtagcgagc ggccgcaagc taaaacgacg gccagtgaat tatcaacttt gtatagaaaa
6961 gttggtttgt gtcttctaga ttaatcctcc aaacttttga ttaaccaaaa aaattatcaa
7021 actaacatgt tctccttttt tctttagaaa ttctaacgaa tttatcttta tactgatttg
7081 aatatactta atttggtcat ttggatgccc tttacaacct ccttaccaaa atattgatca
7141 cagtttctat tgctaaaatc accaacaaaa cgcatgtcgc cattcataat tatggtttca
7201 cacctacaac taggctaata agtaaataag tagacaacta gactcaggtt tgaaaaaacc
7261 ataaagcca tatagcgttt tctcattgaa actgcgaaca cgatcgtgtg aatgttgcag
7321 tttctagttt tgatacaaac aaacaaaaac acaatttaat cttagattaa aaagaaaaaa
7381 gagaacggag cccactagcc actccttcaa acgtgtctta ccaactctct tctagaaaca
7441 aattaggctt caccttcctc ttccaacctc tctctctctc tctctctctt tttctcaaac
7501 catctctcca taaagcccta atttcttcat cacaagaatc agaagaagaa acaagtttgt
7561 acaaaaaagc aggcttactg caaaaaactt atggacctgc atctaatttt cggtccaact
7621 tgcacaggaa agacgacgac gcgatagct cttgcccagc agacagggct tccagtcctt
7681 tgcttgatc gggtccaatg ctgtcctcaa ctatcaaccg gaagcggacg accaacagtg
7741 gaagaactga aggaacgac gcgtctctac cttgatgatc ggcctctggt ggagggtatc
7801 atcgcagcca agcaagctca tcataggctg atcgaggagg tgtataatca tgaggccaac
7861 ggcgggctta ttcttgaggg aggatccacc tcgttgctca actgcatggc gcgaaacagc
7921 tattggagtg cagatttttcg ttggcatatt attcgccaca agttaccga ccaagagacc
7981 ttcatgaaag cggccaaggc cagagttaag cagatgttgc acccgctgc aggccattct
8041 attattcaag agttggttta tctttggaat gaacctcggc tgaggcccat tctgaaagag
```

Figure 23.
(Cont.)

```
8101 atcgatggat atcgatatgc catgttgttt gctagccaga accagatcac ggcagatatg
8161 ctattgcagc ttgacgcaaa tatggaaggt aagttgatta atgggatcgc tcaggagtat
8221 ttcatccatg cgcgccaaca ggaacagaaa ttcccccaag ttaacgcagc cgctttcgac
8281 ggattcgaag gtcatccgtt cggaatgtat taggtaccca gctttcttgt acaaagtggg
8341 atcgttcaaa catttggcaa taaagtttct taagattgaa tcctgttgcc ggtcttgcga
8401 tgattatcat ataatttctg ttgaattacg ttaagcatgt aataattaac atgtaatgca
8461 tgacgttatt tatgagatgg gtttttatga ttagagtccc gcaattatac atttaatacg
8521 cgatagaaaa caaaatatag cgcgcaaact aggataaatt atcgcgcgcg gtgtcatcta
8581 tgttactaga tccaactttta ttatacatag ttgataattc actggccgtc gcttattcca
8641 tggctgcagg tcgacgaatt caccggttaa ctataacggt cctaaggtag cgatggcaaa
8701 cagctattat gggtattatg ggtggttctt tatgcggaca ctgacggctt tatgcctgca
8761 ggtcgcgagc gatcgcggta ccgcccgggc gtcgacaggc ctaagcttag cttgagcttg
8821 gatcagattg tcgtttcccg ccttcagttt aaactatcag tgtttgacag gatatattgg
8881 cgggtaaacc taagagaaaa gagcgtttat tagaataacg gatatttaaa agggcgtgaa
8941 aaggtttatc cgttcgtcca tttgtatgtg catgccaacc acagggttcc cctcgggatc
9001 aaagtacttt gatccaaccc ctccgctgct atagtgcagt cggcttctga cgttcagtgc
9061 agccgtcttc tgaaaacgac atgtcgcaca agtcctaagt tacgcgacag gctgccgccc
9121 tgcccttttc ctggcgtttt cttgtcgcgt gttttagtcg cataaagtag aatacttgcg
9181 actagaaccg gagacattac gccatgaaca agagcgccgc cgctggcctg ctgggctatg
9241 cccgcgtcag caccgacgac caggacttga ccaaccaacg ggccgaactg cacgcggccg
9301 gctgcaccaa gctgttttcc gagaagatca ccggcaccag gcgcgaccgc ccggagctgg
9361 ccaggatgct tgaccaccta cgccctggcg acgttgtgac agtgaccagg ctagaccgcc
9421 tggcccgcag cacccgcgac ctactggaca ttgccgagcg catccaggag gccggcgcgg
9481 gcctgcgtag cctggcagag ccgtgggccg acaccaccac gccggccggc cgcatggtgt
9541 tgaccgtgtt cgccggcatt gccgagttcg agcgttccct aatcatcgac cgcacccgga
9601 gcgggcgcga ggccgccaag gcccgaggcg tgaagtttgg cccccgccct acccteaccc
9661 cggcacagat cgcgcacgcc cgcgagctga tcgaccagga aggccgcacc gtgaaagagg
9721 cggctgcact gcttggcgtg catcgctcga ccctgtaccg cgcacttgag cgcagcgagg
9781 aagtgacgcc caccgaggcc aggcggcgcg gtgccttccg tgaggacgca ttgaccgagg
9841 ccgacgccct ggcggccgcc gagaatgaac gccaagagga acaagcatga aaccgcacca
9901 ggacggccag gacgaaccgt ttttcattac cgaagagatc gaggcggaga tgatcgcggc
9961 cgggtacgtg ttcgagccgc ccgcgcacgt ctcaaccgtg cggctgcatg aaatcctggc
10021 cggtttgtct gatgccaagc tggcggcctg gccggccagc ttggccgctg aagaaaccga
10081 gcgccgccgt ctaaaaaggt gatgtgtatt tgagtaaaac agcttgcgtc atgcggtcgc
10141 tgcgtatatg atgcgatgag taaataaaca aatacgcaag gggaacgcat gaaggttatc
10201 gctgtactta accagaaagg cgggtcaggc aagacgacca tcgcaaccca tctagcccgc
10261 gccctgcaac tcgccggggc cgatgttctg ttagtcgatt ccgatcccca gggcagtgcc
10321 cgcgattggg cggccgtgcg ggaagatcaa ccgctaaccg ttgtcggcat cgaccgcccg
10381 acgattgacc gcgacgtgaa ggccatcggc cggcgcgact tcgtagtgat cgacggagcg
10441 ccccaggcgg cggacttggc tgtgtccgcg atcaaggcag ccgacttcgt gctgattccg
10501 gtgcagccaa gcccttacga catatgggcc accgccgacc tggtggagct ggttaagcag
10561 cgcattgagg tcacggatgg aaggctacaa gcggcctttg tcgtgtcgcg ggcgatcaaa
10621 ggcacgcgca tcggcggtga ggttgccgag gcgctggccg ggtacgagct gcccattctt
10681 ga
```

Figure 23.
(Cont.)

```
   1 ttatacatag ttgataattc actggccgtc gtgggggatc cactagttct agagcggccg
  61 ccaccgcggt ggagctccag cttttgttcc ctttagtgag ggttaatttc gagcttggcg
 121 taatcatggt catagctgtt tcctgtgtga aattgttatc cgctcacaat tccacacaac
 181 atacgagccg gaagcataaa gtgtaaagcc tggggtgcct aatgagtgag ctaactcaca
 241 ttaattgcgt tgcgctcact gcccgctttc cagtcgggaa acctgtcgtg ccagctgcat
 301 taatgaatcg gccaacgcgc ggggagaggc ggtttgcgta ttgggcgctc ttccgcttcc
 361 tcgctcactg actcgctgcg ctcggtcgtt cggctgcggc gagcggtatc agctcactca
 421 aaggcggtaa tacgttatc cacagaatca ggggataacg caggaaagaa catgtgagca
 481 aaaggccagc aaaaggccag gaaccgtaaa aaggccgcgt tgctggcgtt tttccatagg
 541 ctccgccccc ctgacgagca tcacaaaaat cgacgctcaa gtcagaggtg gcgaaacccg
 601 acaggactat aaagatacca ggcgtttccc cctggaagct ccctcgtgcg ctctcctgtt
 661 ccgaccctgc cgcttaccgg atacctgtcc gcctttctcc cttcgggaag cgtggcgctt
 721 tctcatagct cacgctgtag gtatctcagt tcggtgtagg tcgttcgctc caagctgggc
 781 tgtgtgcacg aaccccccgt tcagcccgac cgctgcgcct tatccggtaa ctatcgtctt
 841 gagtccaacc cggtaagaca cgacttatcg ccactggcag cagccactgg taacaggatt
 901 agcagagcga ggtatgtagg cggtgctaca gagttcttga agtggtggc taactacggc
 961 tacactagaa ggacagtatt tggtatctgc gctctgctga agccagttac cttcggaaaa
1021 agagttggta gctcttgatc cggcaaacaa accaccgctg gtagcggtgg tttttttgtt
1081 tgcaagcagc agattacgcg cagaaaaaaa ggatctcaag aagatccttt gatcttttct
1141 acggggtctg acgctcagtg gaacgaaaac tcacgttaag ggattttggt catgagatta
1201 tcaaaaagga tcttcaccta gatccttta aattaaaaat gaagttttaa atcaatctaa
1261 agtatatatg agtaaacttg gtctgacagt taccaatgct taatcagtga ggcacctatc
1321 tcagcgatct gtctatttcg ttcatccata gttgcctgac tccccgtcgt gtagataact
1381 acgatacggg agggcttacc atctggcccc agtgctgcaa tgataccgcg agacccacgc
1441 tcaccggctc cagatttatc agcaataaac cagccagccg gaagggccga gcgcagaagt
1501 ggtcctgcaa ctttatccgc ctccatccag tctattaatt gttgccggga agctagagta
1561 agtagttcgc cagttaatag tttgcgcaac gttgttgcca ttgctacagg catcgtggtg
1621 tcacgctcgt cgtttggtat ggcttcattc agctccggtt cccaacgatc aaggcgagtt
1681 acatgatccc ccatgttgtg caaaaaagcg gttagctcct tcggtcctcc gatcgttgtc
1741 agaagtaagt tggccgcagt gttatcactc atggttatgg cagcactgca taattctctt
1801 actgtcatgc catccgtaag atgcttttct gtgactggtg agtactcaac caagtcattc
1861 tgagaatagt gtatgcggcg accgagttgc tcttgcccgg cgtcaatacg ggataatacc
1921 gcgccacata gcagaacttt aaaagtgctc atcattggaa aacgttcttc ggggcgaaaa
1981 ctctcaagga tcttaccgct gttgagatcc agttcgatgt aacccactcg tgcacccaac
2041 tgatcttcag catcttttac tttcaccagc gtttctgggt gagcaaaaac aggaaggcaa
2101 aatgccgcaa aaaagggaat aagggcgaca cggaaatgtt gaatactcat actcttcctt
2161 tttcaatatt attgaagcat ttatcagggt tattgtctca tgagcggata catatttgaa
2221 tgtatttaga aaaataaaca ataggggtt ccgcgcacat ttccccgaaa agtgccacct
2281 gacgcgcccc gtagcggcgc attaagcgcg gcgggtgtgg tggttacgcg cagcgtgacc
2341 gctacacttg ccagcgccct agcgcccgct cctttcgctt tcttcccttc ctttctcgcc
2401 acgttcgccg gctttccccg tcaagctcta aatcggggc tccctttagg gttccgattt
2461 agtgctttac ggcacctcga ccccaaaaaa cttgattagg gtgatggttc acgtagtggg
2521 ccatcgccct gatagacggt ttttcgccct ttgacgttgg agtccacgtt ctttaatagt
2581 ggactcttgt tccaaactgg aacaacactc aaccctatct cggtctattc ttttgattta
2641 taagggattt tgccgatttc ggcctattgg ttaaaaaatg agctgattta acaaaaattt
```

Figure 25.

```
2701 aacgcgaatt ttaacaaaat attaacgctt acaatttcca ttcgccattc aggctgcgca
2761 actgttggga agggcgatcg gtgcgggcct cttcgctatt acgccagctg gcgaaagggg
2821 gatgtgctgc aaggcgatta agttgggtaa cgccagggtt ttcccagtca cgacgttgta
2881 aaacgacggc cagtgaattg taatacgact cactataggg cgaattgggt accggccccc
2941 ccctcgaggt cgacggtatc gataagcttg atatcgaatt ctcatgtttg acagcttatc
3001 atcggatcta gtaacataga tgacaccgcg cgcgataatt tatcctagtt tgcgcgctat
3061 attttgtttt ctatcgcgta ttaaatgtat aattgcggga ctctaatcat aaaaacccat
3121 ctcataaata acgtcatgca ttacatgtta attattacat gcttaacgta attcaacaga
3181 aattatatga taatcatcgc aagaccggca acaggattca atcttaagaa actttattgc
3241 caaatgtttg aacgatctgc aggtcgacgg atcagatctc ggtgacgggc aggaccggac
3301 ggggcggtac cggcaggctg aagtccagct gccagaaacc cacgtcatgc cagttccgt
3361 gcttgaagcc ggccgccgc agcatgccgc gggggcata tccgagcgcc tcgtgcatgc
3421 gcacgctcgg gtcgttgggc agcccgatga cagcgaccac gctcttgaag ccctgtgcct
3481 ccagggactt cagcaggtgg gtgtagagcg tggagcccag tcccgtccgc tggtggcggg
3541 gggagacgta cacggtcgac tcggccgtcc agtcgtaggc gttgcgtgcc ttccaggggc
3601 ccgcgtaggc gatgccggcg acctcgccgt ccacctcggc gacgagccag ggatagcgct
3661 cccgcagacg gacgaggtcg tccgtccact cctgcggttc ctgcggctcg gtacggaagt
3721 tgaccgtgct tgtctcgatg tagtggttga cgatggtgca gaccgccggc atgtccgcct
3781 cggtggcacg gcggatgtcg gccgggcgtc gttctgggct catggttact tcctaatcga
3841 tggatcctct agagtcgacc tgcagaagta acaccaaaca acagggtgag catcgacaaa
3901 agaaacagta ccaagcaaat aaatagcgta tgaaggcagg gctaaaaaaa tccacatata
3961 gctgctgcat atgccatcat ccaagtatat caagatcaaa ataattataa aacatacttg
4021 tttattataa tagataggta ctcaaggtta gagcatatga atagatgctg catatgccat
4081 catgtatatg catcagtaaa acccacatca acatgtatac ctatcctaga tcgatatttc
4141 catccatctt aaactcgtaa ctatgaagat gtatgacaca cacatacagt tccaaaatta
4201 ataaatacac caggtagttt gaaacagtat tctactccga tctagaacga atgaacgacc
4261 gcccaaccac accacatcat cacaaccaag cgaacaaaaa gcatctctgt atatgcatca
4321 gtaaaacccg catcaacatg tatacctatc ctagatcgat atttccatcc atcattttca
4381 attcgtaact atgaatatgt atggcacaca catacagatc caaaattaat aaatccacca
4441 ggtagtttga aacagaattc tactccgatc tagaacgacc gcccaaccag accacatcat
4501 cacaaccaag acaaaaaaaa gcatgaaaag atgacccgac aaacaagtgc acggcatata
4561 ttgaaataaa ggaaagggc aaaccaaacc ctatgcaacg aaacaaaaaa aatcatgaaa
4621 tcgatcccgt ctgcggaacg gctagagcca tccaggatt ccccaaagag aaacactggc
4681 aagttagcaa tcagaacgtg tctgacgtac aggtcgcatc cgtgtacgaa cgctagcagc
4741 acggatctaa cacaaacacg gatctaacac aaacatgaac agaagtagaa ctaccgggcc
4801 ctaaccatgg accggaacgc cgatctagag aaggtagaga ggggggggg gggaggacga
4861 gcggcgtacc ttgaagcgga ggtgccgacg ggtggatttg ggggagatct ggttgtgtgt
4921 gtgtgcgctc cgaacaacac gaggttgggg aaagagggtg tggaggggt gtctatttat
4981 tacgcgggc gaggaaggga aagcgaagga gcggtgggaa aggaatcccc cgtagctgcc
5041 ggtgccgtga gaggaggagg aggccgcctg ccgtgccggc tcacgtctgc cgctccgcca
5101 cgcaatttct ggatgccgac agcggagcaa gtccaacggt ggagcggaac tctcgagagg
5161 ggtccagagg cagcgacaga gatgccgtgc cgtctgcttc gcttggcccg acgcgacgct
5221 gctggttcgc tggttggtgt ccgttagact cgtcgacggc gtttaacagg ctggcattat
5281 ctactcgaaa caagaaaaat gtttccttag tttttttaat ttcttaaagg gtatttgttt
5341 aatttttagt cactttattt tattctattt tatatctaaa ttattaaata aaaaaactaa
```

Figure 25.
(Cont.)

```
5401 aatagagttt tagttttctt aatttagagg ctaaaataga ataaaataga tgtactaaaa
5461 aaattagtct ataaaaacca ttaaccctaa accctaaatg gatgtactaa taaaatggat
5521 gaagtattat ataggtgaag ctatttgcaa aaaaaaagga gaacacatgc acactaaaaa
5581 gataaaactg tagagtcctg ttgtcaaaat actcaattgt cctttagacc atgtctaact
5641 gttcatttat atgattctct aaaacactga tattattgta gtactataga ttatattatt
5701 cgtagagtaa agtttaaata tatgtataaa gatagataaa ctgcacttca aacaagtgtg
5761 acaaaaaaaa tatgtggtaa ttttttataa cttagacatg caatgctcat tatctctaga
5821 gaggggcacg accgggtcac gctgcactgc aggcatgcaa gcttgaattc ctgcagcccc
5881 gccaagctat caactttgta tagaaaagtt ggtttgtgtc ttctagatta atcctccaaa
5941 cttttgatta accaaaaaaa ttatcaaact aacatgttct ccttttttct ttagaaattc
6001 taacgaattt atctttatac tgatttgaat atacttaatt tggtcatttg gatgcccttt
6061 acaacctcct taccaaactc actatggcaa atatatacta ttttccattg taacataaat
6121 gtccataatt tgaattaaat tcgttgcagt acgaaaccat ccaactttgt ccaaaaacaa
6181 aatccttata actatttact ttaatgtaaa tatatcctct acttttgttt ttacaaccct
6241 agctcaaaca aatttattat ttgcgataaa aaatcatatc gaacaaactc gatgattttt
6301 ttttttcttac gttattaatg aaactaaaat atagaaaaaa acaagatgaa ccaaattttc
6361 acctatctaa ctacttaaat ataatatgat taaatttggt aaagtttgaa aagtttcttt
6421 agaaatgtga aatattgatc acagtttcta ttgctaaaat caccaacaaa acgcatgtcg
6481 ccattcataa ttatggtttc acacctacaa ctaggctaat aagtaaataa gtagacaact
6541 agactcaggt ttgaaaaaac cataaaagcc atatagcgtt ttctcattga aactgcgaac
6601 acgatcgtgt gaatgttgca gtttctagtt ttgatacaaa caaacaaaaa cacaatttaa
6661 tcttagatta aaaagaaaaa agagaacgga gcccactagc cactccttca aacgtgtctt
6721 accaactctc ttctagaaac aaattaggct tcaccttcct cttccaacct ctctctctct
6781 ctctctctct ttttctcaaa ccatctctcc ataaagccct aatttcttca tcacaagaat
6841 cagaagaaga aacaagtttg tacaaaaaag caggcttact gcaaaaaact tatggacctg
6901 catctaattt tcggtccaac ttgcacagga aagacgacga ccgcgatagc tcttgcccag
6961 cagacagggc ttccagtcct ttcgcttgat cgggtccaat gctgtcctca actatcaacc
7021 ggaagcggac gaccaacagt ggaagaactg aaaggaacga cgcgtctcta ccttgatgat
7081 cggcctctgg tggagggtat catcgcagcc aagcaagctc atcataggct gatcgaggag
7141 gtgtataatc atgaggccaa cggcgggctt attcttgagg gaggatccac ctcgttgctc
7201 aactgcatgg cgcgaaacag ctattggagt gcagattttc gttggcatat tattcgccac
7261 aagttacccg accaagagac cttcatgaaa gcggccaagg ccagagttaa gcagatgttg
7321 caccccgctg caggccattc tattattcaa gagttggttt atctttggaa tgaacctcgg
7381 ctgaggccca ttctgaaaga gatcgatgga tatcgatatg ccatgttgtt tgctagccag
7441 aaccagatca cggcagatat gctattgcag cttgacgcaa atatggaagg taagttgatt
7501 aatgggatcg ctcaggagta tttcatccat gcgcgccaac aggaacagaa attcccccaa
7561 gttaacgcag ccgctttcga cggattcgaa ggtcatccgt tcggaatgta ttaggtaccc
7621 agctttcttg tacaaagtgg agtccgcaaa aatcaccagt ctctctctac aaatctatct
7681 ctctctattt ttctccagaa taatgtgtga gtagttccca gataagggaa ttagggttct
7741 tatagggttt cgctcatgtg ttgagcatat aagaaaccct tagtatgtat ttgtatttgt
7801 aaaatacttc tatcaataaa atttctaatt cctaaaacca aaatccagtg acctcaactt
7861 ta
```

Figure 25.
(Cont.)

MANIPULATION OF PLANT SENESCENCE USING MODIFIED PROMOTERS

CROSS-REFERENCE TO RELATED APPLICATIONS

This application is a continuation-in-part of U.S. patent application Ser. No. 11/789,526 entitled "Manipulation of plant senescence using modified promoters" filed Apr. 24, 2007, now abandoned, which is a continuation-in-part of U.S. patent application Ser. No. 10/363,723 entitled "Manipulation of plant senescence using an MYB gene promoter and cytokinin biosynthesis gene" filed Jun. 6, 2003, issued as U.S. Pat. No. 7,227,055 on Jun. 5, 2007, which claims priority from International Patent Application No. PCT/AU0I/01092, entitled "Manipulation of Plant Senescence Using An MYB Gene Promoter and Cytokinin Biosynthesis Genes," filed Aug. 30, 2001, which claims priority from Australian Patent Application No. PQ 9946, entitled "Manipulation of Plant Senescence Using An MYB Gene Promoter and Cytokinin Biosynthesis Genes," filed Sep. 6, 2000; and this application is also a continuation-in-part of International Patent Application No. PCT/AU2008/000566 entitled "Manipulation of plant senescence using modified promoters" filed Apr. 21, 2008, which claims priority from U.S. patent application Ser. No. 11/789,526 filed Apr. 24, 2007, now abandoned; the contents of which are incorporated by reference herein in their entirety.

The present invention relates to methods of manipulating senescence in plants. The invention also relates to vectors useful in such methods, transformed plants with modified senescence characteristics and plant cells, seeds and other parts of such plants.

Leaf senescence involves metabolic and structural changes in cells prior to cell death. It also involves the recycling of nutrients to actively growing regions.

The regulation of plant and plant organ senescence by cytokinins has important agricultural consequences. Elevated cytokinin levels in leaves tend to retard senescence. A number of promoters have been used to regulate the expression of the ipt gene, whose product (isopentenyltransferase) catalyses a key step in cytokinin synthesis. However, in general, transgenic plants over-expressing the ipt gene have been reported to have retarded root and shoot growth, no root formation, reduced apical dominance, and reduced leaf area.

It is an object of the present invention to overcome, or at least alleviate, one or more of the difficulties or deficiencies associated with the prior art.

In one aspect, the present invention provides a method of manipulating senescence in a plant, said method including introducing into said plant a genetic construct including a modified myb gene promoter, or a functionally active fragment or variant thereof, operatively linked to a gene encoding an enzyme involved in biosynthesis of a cytokinin, or a functionally active fragment or variant thereof.

The manipulation of senescence relates to the plant and/or specific plant organs. Senescence of different plant organs, such as leaves, roots, shoots, stems, tubers, flowers, stolons, and fruits may be manipulated. The manipulation of plant and plant organ senescence may have important agricultural consequences, such as increased shelf life of e.g. fruits, flowers, leaves and tubers in horticultural produce and cut flowers, reduced perishability of horticultural crops, increased carbon fixation in senescence-retarded leaves leading to enhanced yields, enhanced biomass production in forage plants, enhanced seed production, etc.

"Manipulating senescence" generally relates to delaying senescence in the transformed plant relative to an untransformed control plant. However, for some applications it may be desirable to promote or otherwise modify senescence in the plant. Senescence may be promoted or otherwise modified for example, by utilizing an antisense gene.

An effective amount of said genetic construct may be introduced into said plant, by any suitable technique, for example by transduction, transfection or transformation. By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

By a "modified myb gene promoter" is meant a promoter normally associated with a myb gene, which promoter is modified to delete or inactivate one or more root specific motifs and/or pollen specific motifs in said promoter.

While applicant does not wish to be restricted by theory, it is postulated that deletion or inactivation of one or more root specific motifs in said myb gene promoter may alleviate or overcome the problem of leaky expression of the gene encoding a cytokinin biosynthetic enzyme in plant meristems, which may affect root development in some species of plants. It is also postulated that deletion or inactivation of one or more pollen specific motifs in said myb gene promoter may alleviate or overcome the problem of leaky expression of the gene encoding a cytokinin biosynthetic enzyme in pollen, which may affect pollen development in some species of plants.

Preferably the modified myb gene promoter is a modified myb32 gene promoter. Preferably the modified myb gene promoter is from *Arabidopsis*, more preferably *Arabidopsis thaliana*.

A suitable promoter which may be modified according to the present invention is described in Li et al., Cloning of three MYB-like genes from *Arabidopsis* (PGR 99-138) Plant Physiology 121:313 (1999), the entire disclosure of which is incorporated herein by reference.

By a "root specific motif" is meant a sequence of 3-7 nucleotides, preferably 4-6 nucleotides, more preferably 5 nucleotides, which directs expression of an associated gene in the roots of a plant.

Preferably the root specific motif includes a consensus sequence ATATT or AATAT.

Preferably, between one and ten, more preferably between three and eight, even more preferably between five and seven root specific motifs are deleted or inactivated, preferably deleted, in said myb gene promoter.

The root specific motifs may be deleted by removing individual motifs or by removing a fragment of the promoter containing one or more motifs. For example, all or part of the region between nucleotides 1 and 530, preferably between nucleotides 110 and 530 of the *Arabidopsis thaliana* myb gene promoter may be deleted.

The deletion may be effected by cutting the nucleic acid, for example with restriction endonucleases, and ligating the cut ends to generate a promoter with a fragment removed.

For example, a modified *Arabidopsis thaliana* myb gene promoter may be prepared by removing a fragment between the XcmI site at positions 162-176 and the SspI site at positions 520-525. This generates a modified myb gene promoter with 6 of the 7 root specific motifs deleted. Alternatively, all 7 of the root specific motifs may be deleted, for example by deleting the region upstream of the SspI site at positions 520-525, or by deleting the region between nucleotides 1 and 120 together with the region between the XcmI site at positions 162-176 and the SspI site at positions 520-525.

A root specific motif may be inactivated by adding, deleting, substituting or derivatizing one or more nucleotides within the motif, so that it no longer has the preferred consensus sequence.

Preferably the modified myb gene promoter includes a nucleotide sequence selected from the group consisting of the sequences shown in FIGS. 2, 3 and 4 hereto (Sequence ID Nos: 2, 3 and 4, respectively) and functionally active fragments and variants thereof.

By a "pollen specific motif" is meant a sequence of 3-7 nucleotides, preferably 4-6 nucleotides, more preferably 4 or 5 nucleotides, which directs expression of an associated gene in the pollen of a plant.

Preferably the pollen specific motif includes a consensus sequence selected from the group consisting of TTCT and AGAA.

Preferably, between one and thirty, more preferably between three and fifteen, even more preferably between four and ten pollen specific motifs are deleted or inactivated, preferably deleted, in said myb gene promoter.

The pollen specific motifs may be deleted by removing individual motifs or by removing a fragment of the promoter containing one or more motifs. For example, all or part of the region between nucleotides 1 and 540, preferably between nucleotides 390 and 540 of the *Arabidopsis thaliana* myb gene promoter may be deleted.

The deletion may be effected by cutting the nucleic acid, for example with restriction endonucleases, and ligating the cut ends to generate a promoter with a fragment removed.

For example, a modified *Arabidopsis thaliana* myb gene promoter may be prepared by removing a fragment between the XcmI site at positions 162-176 and the SspI site at positions 520-525. This generates a modified myb gene promoter with 4 of the 23 pollen specific motifs deleted. Alternatively, 10 of the pollen specific motifs may be deleted, for example by deleting the region upstream of the SspI site at positions 520-525.

A pollen specific motif may be inactivated by adding, deleting, substituting or derivatizing one or more nucleotides within the motif, so that it no longer has the preferred consensus sequence.

Preferably the modified myb gene promoter includes a nucleotide sequence selected from the group consisting of the sequences shown in FIGS. 2, 3 and 4 hereto (Sequence ID Nos: 2, 3 and 4, respectively) and functionally active fragments and variants thereof.

In a further aspect of the present invention there is provided a method of enhancing biomass in a plant, said method include introducing into said plant a genetic construct including a myb gene promoter, or a functionally active fragment or variant thereof, operatively linked to a gene encoding an enzyme involved in biosynthesis of a cytokinin, or a functionally active fragment or variant thereof.

The myb gene promoter or a functionally active fragment or variant thereof may be a full length myb gene promoter or a modified myb gene promoter.

The full length myb gene promoter may be a myb32 gene promoter. Preferably the myb gene promoter is from *Arabidopsis,* more preferably *Arabidopsis thaliana.* Most preferably the myb gene promoter includes a nucleotide sequence selected from the group consisting of the sequence shown in FIG. 1 hereto (Sequence ID No: 1) and functionally active fragments and variants thereof.

A suitable promoter is described in Li et al., Cloning of three MYB-like genes from *Arabidopsis* (PGR 99-138) Plant Physiology 121:313 (1999).

The modified myb gene promoter may be a modified myb gene promoter as hereinbefore described.

By "enhancing biomass" is meant enhancing or increasing in a transformed plant relative to an untransformed control plant a growth characteristic selected from the group consisting of total leaf area, cumulative leaf area, leaf growth dynamics (i.e. number of leaves over time), stolon length, percentage of flowering plants and seed yield per flower or per area sown. "Enhancing biomass" also includes reducing or decreasing percentage stolon death in a transformed plant relative to an untransformed control plant.

In particular, applicants have found that while the seed weight (i.e. weight of thousand seeds) of transgenic plants according to the present invention was indistinguishable from non-transgenic control plants, the total seed yield expressed on the basis of per flower or per area sown was significantly higher in the transgenic plants when compared with non-transgenic control plants of equivalent flowering intensity.

By "functionally active" in relation to a myb gene promoter or modified myb gene promoter is meant that the fragment or variant (such as an analogue, derivative or mutant) is capable of manipulating senescence in a plant by the method of the present invention. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, most preferably at least approximately 95% identity. Preferably the fragment has a size of at least 20 nucleotides, more preferably at least 50 nucleotides, more preferably at least 100 nucleotides, more preferably at least 200 nucleotides, most preferably at least 300 nucleotides.

By a "gene encoding an enzyme involved in biosynthesis of a cytokinin" is meant a gene encoding an enzyme involved in the synthesis of cytokines such as kinetin, zeatin and benzyl adenine, for example a gene encoding isopentyl transferase (ipt), or an ipt-like gene such as the sho gene (eg. from petunia). Preferably the gene is an isopentenyl transferase (ipt) gene or sho gene. In a preferred embodiment, the gene is from a species selected from the group consisting of *Agrobacterium,* more preferably *Agrobacterium tumefaciens; Lotus,* more preferably *Lotus japonicus;* and *Petunia,* more preferably *Petunia hybrida.*

Most preferably the gene includes a nucleotide sequence selected from the group consisting of the sequences shown in FIGS. 6, 8 and 10 hereto (Sequence ID Nos: 5, 7 and 9) sequences encoding the polypeptides shown in FIGS. 7, 9 and 11 hereto (Sequence ID Nos: 6, 8 and 10), and functionally active fragments and variants thereof.

By "functionally active" in relation to a gene encoding a cytokinin biosynthetic enzyme is meant that the fragment or variant (such as an analogue, derivative or mutant) is capable of manipulating senescence in a plant by the method of the present invention. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, to which the fragment or variant corresponds more preferably at least approximately 90% identity, most preferably at least approximately 95% identity. Such functionally active variants and fragments include, for example, those having conservative nucleic acid changes or nucleic acid changes which result in conservative amino acid substitutions of one or more residues in the corresponding amino acid sequence. For example, the functionally active variant may include one or more conservative nucleic acid substitutions of a sequence shown in FIG. 6, 8 or 10, the resulting functionally active variant encoding an amino acid sequence shown in FIG. 7, 9 or 11, respectively. Preferably the fragment has a size of at least 20 nucleotides, more preferably at least 50 nucleotides, more preferably at least 100 nucleotides, more preferably at least 500 nucleotides.

The genetic construct may be introduced into the plant by any suitable technique. Techniques for incorporating the genetic constructs of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos, biolistic transformation and combinations thereof. The choice of technique will depend largely on the type of plant to be transformed, and may be readily determined by an appropriately skilled person.

Cells incorporating the genetic construct of the present invention may be selected, as described below, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

The methods of the present invention may be applied to a variety of plants, including monocotyledons [such as grasses (e.g. forage, turf and bioenergy grasses including perennial ryegrass, tall fescue, Italian ryegrass, red fescue, reed canary grass, big bluestem, cordgrass, napiergrass, wildrye, wild sugarcane, Miscanthus), corn, oat, wheat and barley)], dicotyledons [such as *Arabidopsis*, tobacco, soybean, clovers (e.g. white clover, red clover, subterranean clover), alfalfa, canola, vegetable brassicas, lettuce, spinach] and gymnosperms.

In a further aspect of the present invention there is provided a vector capable of manipulating senescence in a plant, said vector including a modified myb gene promoter, or a functionally active fragment or variant thereof, operatively linked to a gene encoding an enzyme involved in the biosynthesis of a cytokinin, or a functionally active fragment or variant thereof.

In a still further aspect of the present invention there is provided a vector capable of enhancing biomass in a plant, said vector including a myb gene promoter, or a functionally active fragment or variant thereof, operatively linked to a gene encoding an enzyme involved in the biosynthesis of a cytokinin, or a functionally active fragment or variant thereof.

The myb gene promoter or a functionally active fragment or variant thereof may be a full length myb gene promoter or a modified myb gene promoter, as described herein.

In a preferred embodiment of this aspect of the invention, the vector may further include a terminator; said promoter, gene and terminator being operably linked.

By "operably linked" is meant that said promoter is capable of causing expression of said gene in a plant cell and said terminator is capable of terminating expression of said gene in a plant cell. Preferably, said promoter is upstream of said gene and said terminator is downstream of said gene.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens;* derivatives of the Ri plasmid from *Agrobacterium rhizogenes;* phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the plant cell.

The promoter, gene and terminator may be of any suitable type and may be endogenous to the target plant cell or may be exogenous, provided that they are functional in the target plant cell.

A variety of terminators which may be employed in the vectors of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the promoter, the gene and the terminator, may include further elements necessary for expression of the gene, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptII) gene, the hygromycin phosphotransferase (hph) gene, the phosphinothricin acetyltransferase (bar or pat) gene], and reporter genes [such as beta-glucuronidase (GUS) gene (gusA)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

Those skilled in the art will appreciate that the various components of the vector are operably linked, so as to result in expression of said gene. Techniques for operably linking the components of the vector of the present invention are well known to those skilled in the art. Such techniques include the use of linkers, such as synthetic linkers, for example including one or more restriction enzyme sites.

In a further aspect of the present invention there is provided a transgenic plant cell, plant, plant seed or other plant part, with modified senescence characteristics or enhanced biomass. Preferably said plant cell, plant, plant seed or other plant part includes a vector according to the present invention. Preferably the transgenic plant cell, plant, plant seed or other plant part is produced by a method according to the present invention.

The present invention also provides a transgenic plant, plant seed or other plant part derived from a plant cell of the present invention.

The present invention also provides a transgenic plant, plant seed or other plant part derived from a plant of the present invention.

The present invention will now be more fully described with reference to the accompanying examples and drawings. It should be understood, however, that the description following is illustrative only and should not be taken in any way as a restriction on the generality of the invention described above.

FIGURES

FIG. 1 shows the nucleotide sequence of the promoter from myb32 gene (atmyb32) from *Arabidopsis thaliana* (Sequence ID No: 1), Atmyb32 promoter sequence with MYB type, pollen specific and Root specific motifs highlighted. WAACCA (underline/italics) MYB1 AT; GTTAGTT ((bold/box)) MYB1LEPR; CCWACC ((box)) MYBPZM; GGATA (italics) MYBST1; AGAAA (underline) POLLEN1LELAT52; ATATT (bold) ROOTMOTIFTAPOX1.

FIG. 2 shows an Atmyb32 promoter sequence variant (Atmyb32xs) with the XcmI-SspI plant sequence deleted. MYB type, pollen specific and Root specific motifs are highlighted. WAACCA (underline/italics) MYB1AT; GTTAGTT ((bold/box)) MYB1LEPR; CCWACC ((box)) MYBPZM; AGAAA (underline) POLLEN1LELAT52; ATATT (bold) ROOTMOTIFTAPOX1 (Sequence ID No: 2).

FIG. 3 shows an Atmyb32 promoter variant sequence with all root motifs deleted. MYB type, pollen specific and Root specific motifs are highlighted. WAACCA (underline/italics) MYB1AT; CCWACC ((box)) MYBPZM; AGAAA (underline) POLLEN1LELAT52 (Sequence ID No: 3).

FIG. 4 shows an Atmyb32 promoter variant sequence with the Sspl site upstream sequence deleted. MYB type, pollen specific and Root specific motifs are highlighted. WAACCA (underline/italics) MYB1AT; CCWACC ((box)) MYBPZM; AGAAA (underline) POLLEN1LELAT52 (Sequence ID No: 4).

FIG. 6 shows the nucleotide sequence of the isopentenyl transferase (ipt) gene from *Agrobacterium tumefaciens* (Sequence ID No: 5).

FIG. 7 shows the deduced amino acid sequence of the isopentyl transferase gene from *Agrobacterium tumefaciens* (Sequence ID No. 6).

FIG. 8 shows the nucleotide sequence of the isopentyl transferase gene from *Lotus japonicus* (Sequence ID No. 7).

FIG. 9 shows the deduced amino acid sequence of the isopentyl transferase gene from *Lotus japonicus* (Sequence ID No. 8).

FIG. 10 shows the Nucleotide sequence of the cytokinin biosynthesis Sho gene from *Petunia hybrida* (Sequence ID No. 9).

FIG. 11 shows the Deduced amino acid sequence of the cytokinin biosynthesis Sho gene from *Petunia hybrida* (Sequence ID No. 10).

Figure 5:
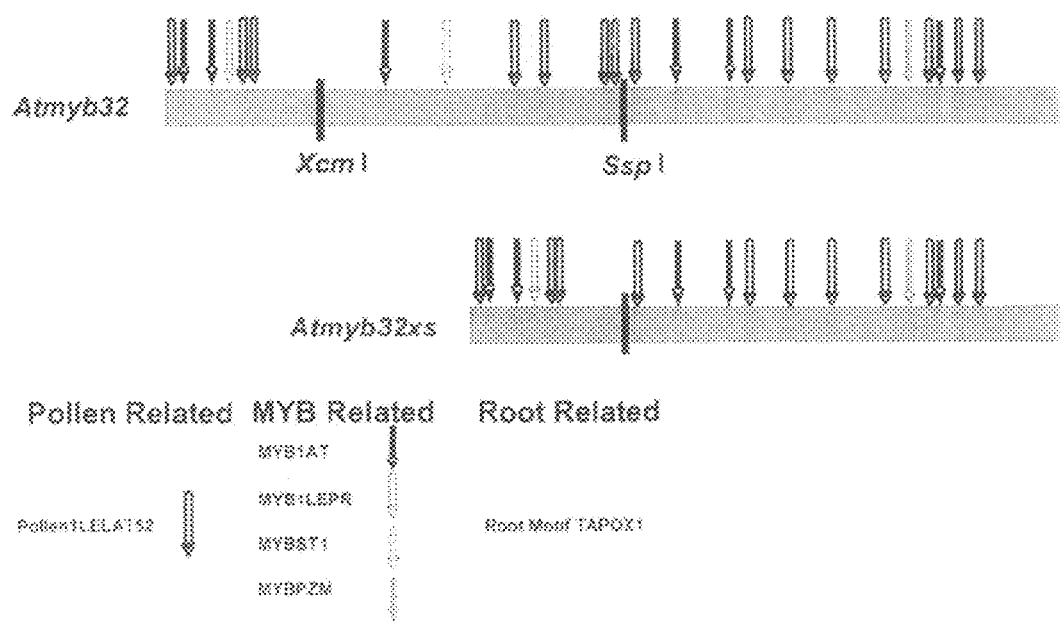
FIG. 5 shows Motifs in Atmyb32 and Atmyb32xs promoter sequences.
Figure 12:
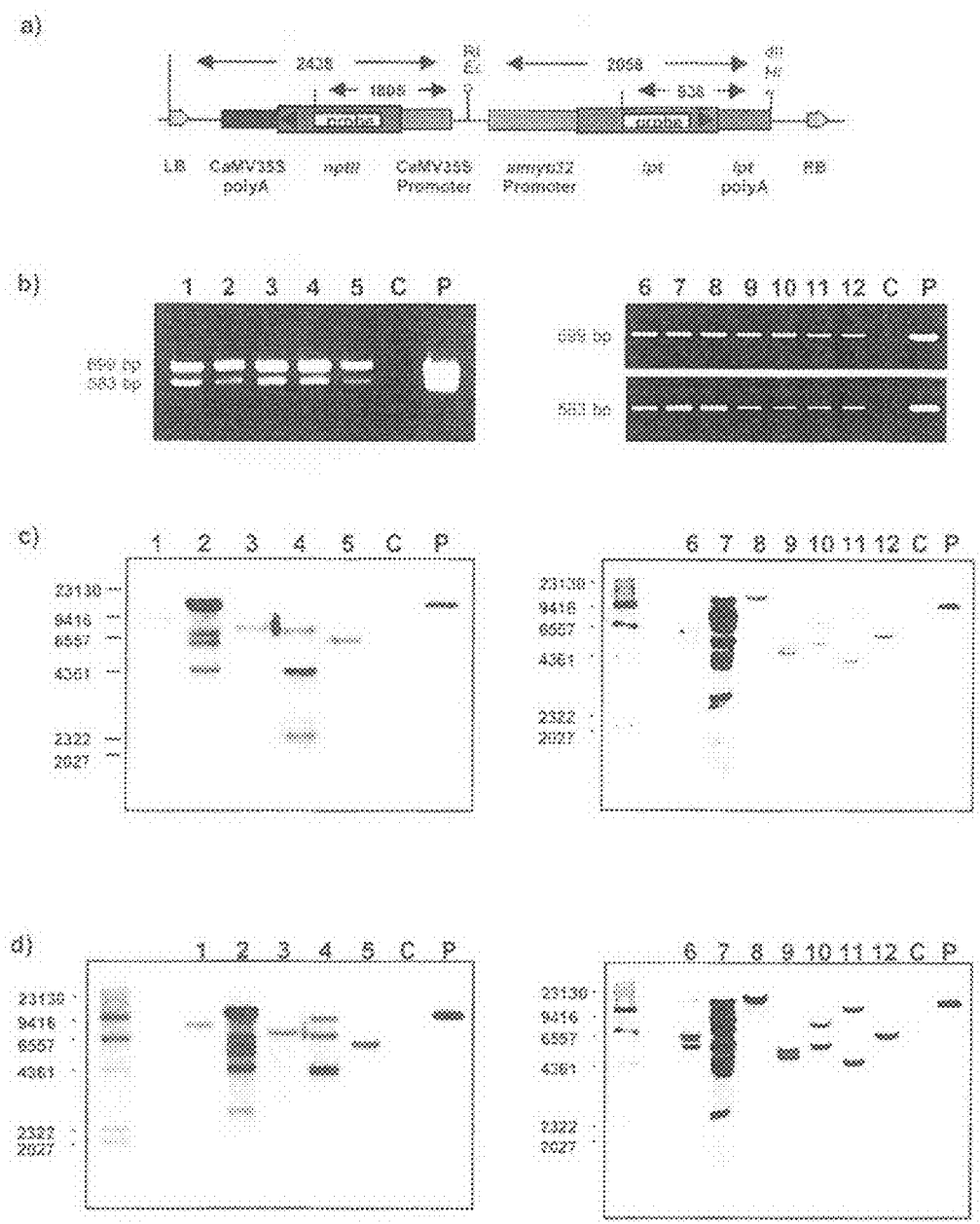

FIG. 12 shows PCR and Southern DNA analysis of atmyb32::ipt transgenic white clover (*Trifolium repens*) plants. a) The T-DNA region of patmyb32:ipt showing restriction enzyme sites and location of the probes used for Southern hybridization analysis. b) Ethidium bromide stained 1% agarose gel of the PCR amplified 599 by nptII and 583 by ipt products. c) Southern blot hybridization with HindIII digested total genomic DNA isolated from PCR positive white clover plants hybridized with the ipt probe. d) Southern blot hybridization with HindIII digested total genomic DNA isolated from PCR positive white clover plants hybridized with the nptll probe. Lanes 1-2: two independent kanamycin resistant cv. Haifa regenerants, code: Hmi01, Hmi08 respectively; Lanes 3-12: twelve independent kanamycin resistant cv. Irrigation regenerants, codes: Imi06, Imi07, Imi08, Imi09, Imi10, Imi11, Imi12, Imi14, Imi16, Imi18 respectively; Lane C: non-transformed white clover; Lane P: positive control plasmid patmyb32ipt.

Figure 13:
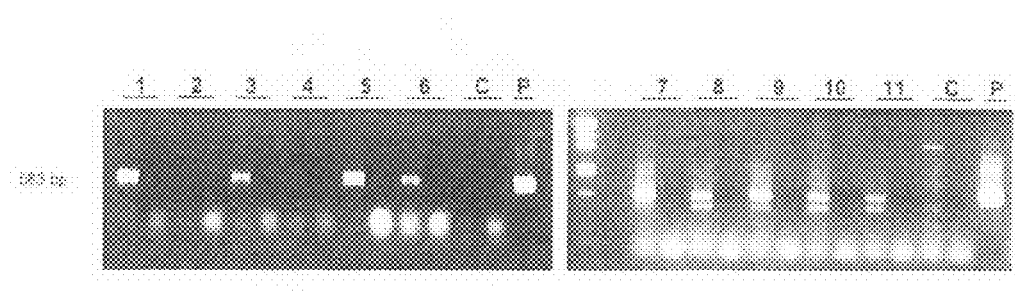

FIG. 13 shows RT-PCR analysis of ipt mRNA expression in atmyb32::ipt transgenic white clover (*T. repens*) plants. Lane 1-11 are samples from 11 independent transgenic lines with corresponding plant codes as in FIG. 4.8; Lane C, Control non-transformed plant; Lane P, plasmid as positive control. Total RNA was isolated from leaf tissues. Total RNA (13 μg) was used for each reverse transcription reaction and ⅕ of RT product was amplified by PCR. DNA products on the gel on the right were amplified by 2×30 cycles intensive PCR. No reverse transcriptase was added to the corresponding RT-PCR reaction loaded into alternate lanes.

Figure 14:
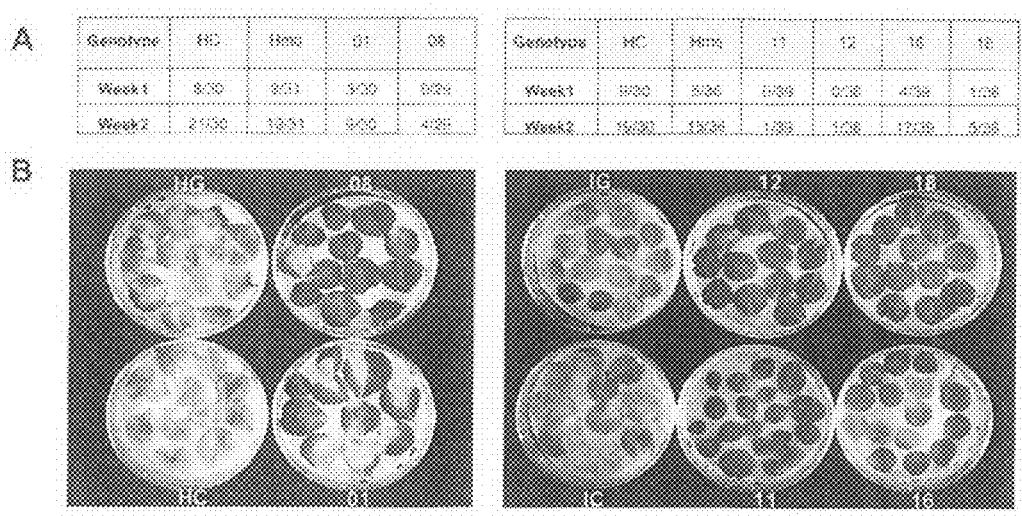

FIG. 14 shows a senescence bioassay of excised leaves from atmyb32::ipt transgenic white clover (*T. repens*) plants. At least 30 leaves were collected from each line from similar positions on stolons of plant lines. A. The number of yellowing leaves as a fraction of the total number of excised leaves. B. Typical appearance of leaves kept on water under light for two weeks. Key to plant lines: HC, IC and Hmg, Img, non-transformed and atmyb32::gusA transgenic plants (cv. Haifa and Irrigation) respectively; 01 and 08, atmyb32::ipt transgenic Haifa lines Hmi01 and Hmi08 respectively; 11, 12, 16 and 18 atmyb32::ipt transgenic Irrigation lines Imi11, Imi12, Imi16 and Imi18 respectively.

Figure 15:
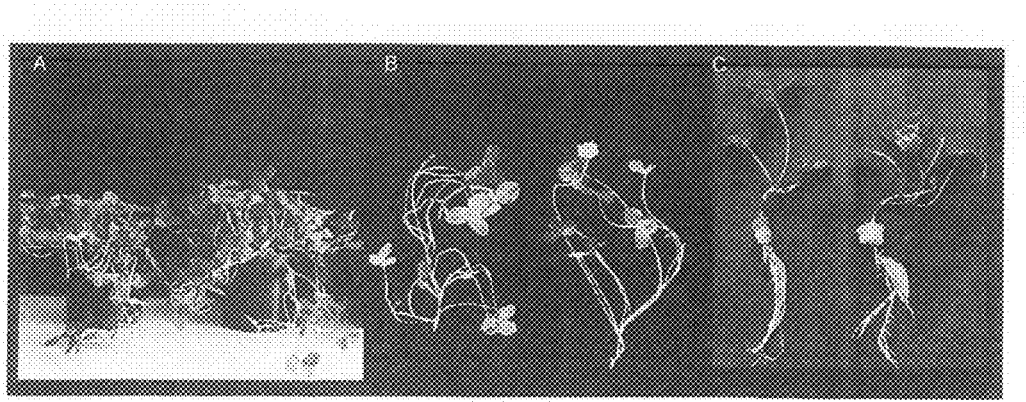

FIG. 15 shows A) General plant morphology, B) Normal shoot development, and C) Normal root development in atmyb32::ipt transgenic white clover (*T. repens*) (right) plants compared to control plants (left).

Figure 16:
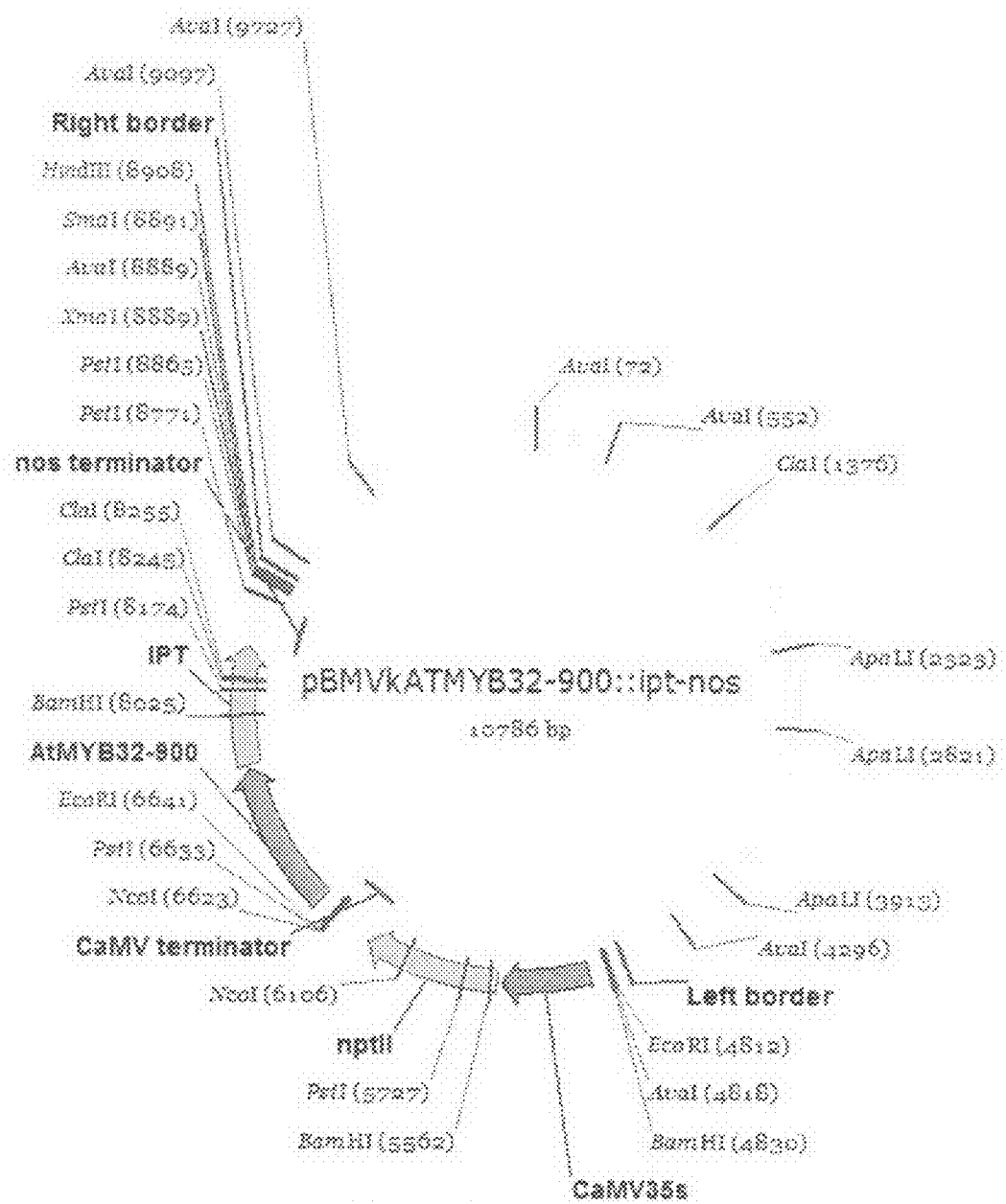

FIG. 16 shows vector details for pBMVkAtMYB32-900::ipt [Gene: Isopentyl transferase (IPT); Vector: pBMVkAtMYB32-900::ipt-nos (backbone pPZPRCS2); Selectable marker: spec; Plant selectable marker cassette: 35S::kan::35ST; Gene promoter: AtMYB32-900; Gene terminator: nos.].

FIG. 17 shows nucleotide sequence of vector pBMVkAtMYB32-900::ipt-nos (Sequence ID No. 11).

Figure 18:
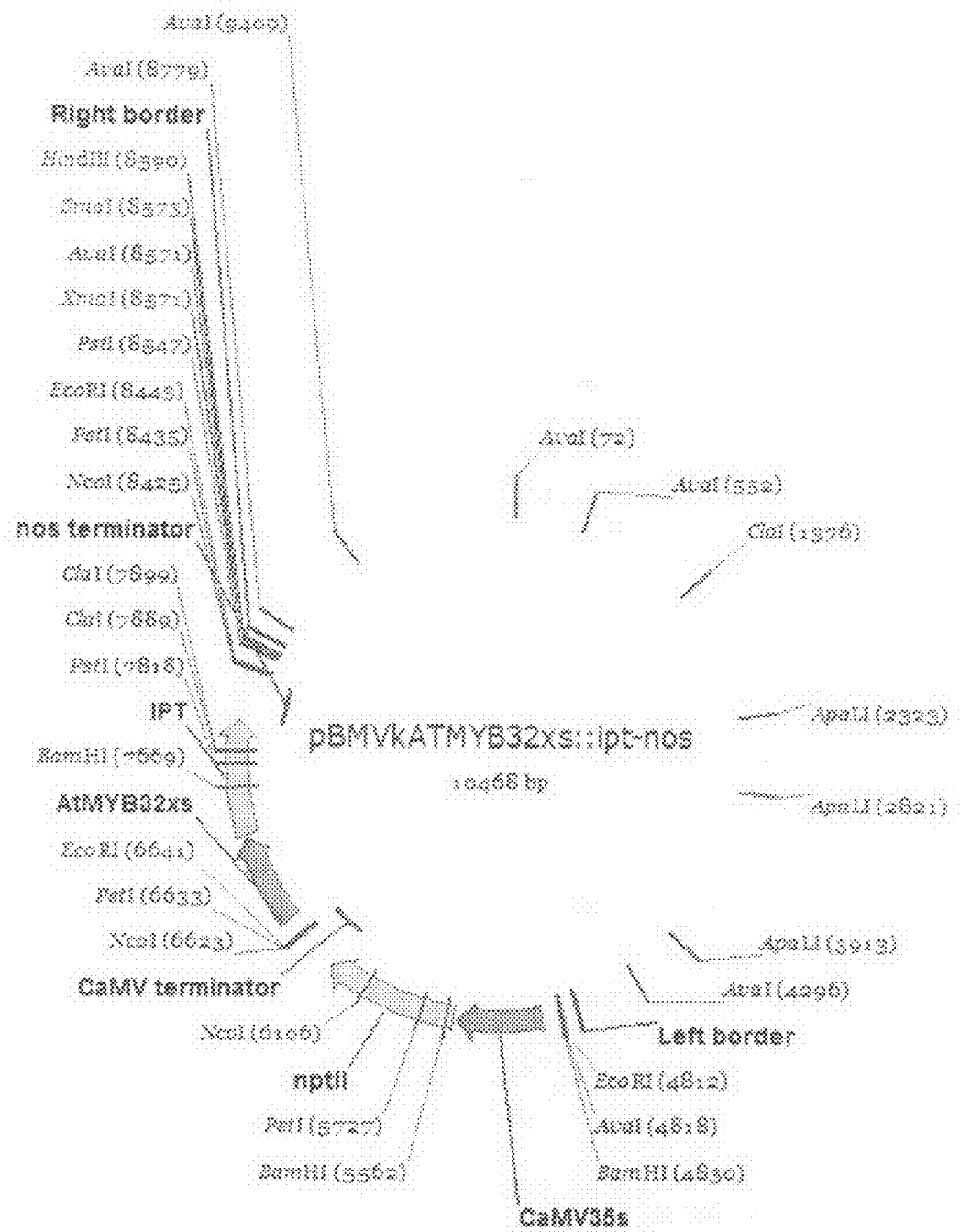

FIG. 18 shows vector details for pBMVkAtMYB32xs::ipt-nos [Gene: Isopentyl transferase (IPT); Vector: pBMVkAtMYB32XS::ipt-nos (backbone pPZPRCS2); Selectable marker: spec; Plant selectable marker cassette: 35S::kan::35ST; Gene promoter: AtMYB32-xs; Gene terminator: nos.].

FIG. 19 shows nucleotide sequence of vector pBMVkAtMYB32xs::ipt-nos (Sequence ID No. 12).

Figure 20:
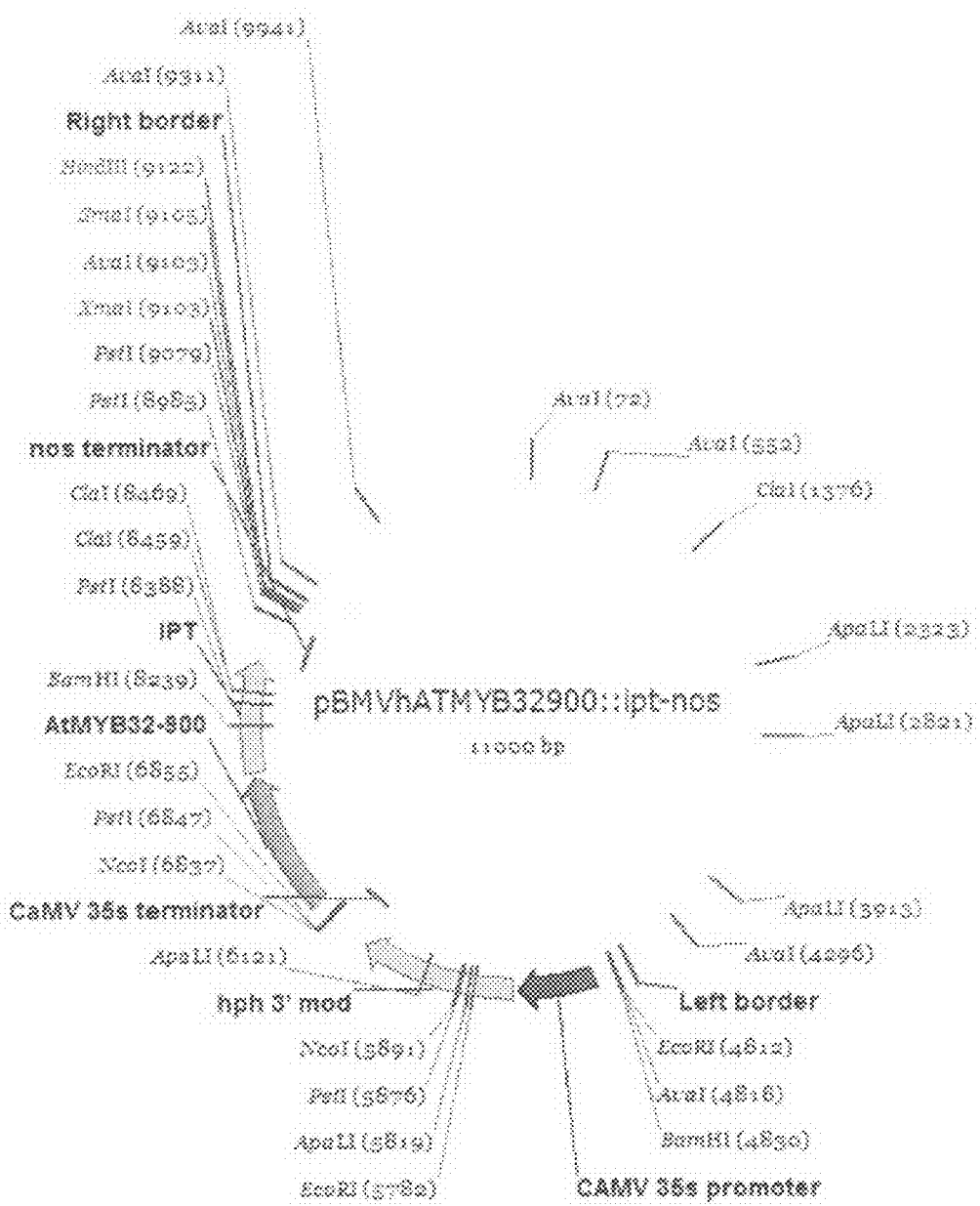

FIG. 20 shows vector details for pBMVhAtMYB32-900::ipt-nos [Gene: Isopentyl transferase (IPT); Vector: pBMVhAtMYB32-900::ipt-nos (backbone pPZPRCS2); Selectable marker: spec; Plant selectable marker cassette: 35S::hph::35ST; Gene promoter: AtMYB32-900; Gene terminator: nos.].

FIG. 21 shows nucleotide sequence of vector pBMVhAtMYB32-900::ipt-nos (Sequence ID No. 13).

Figure 22:
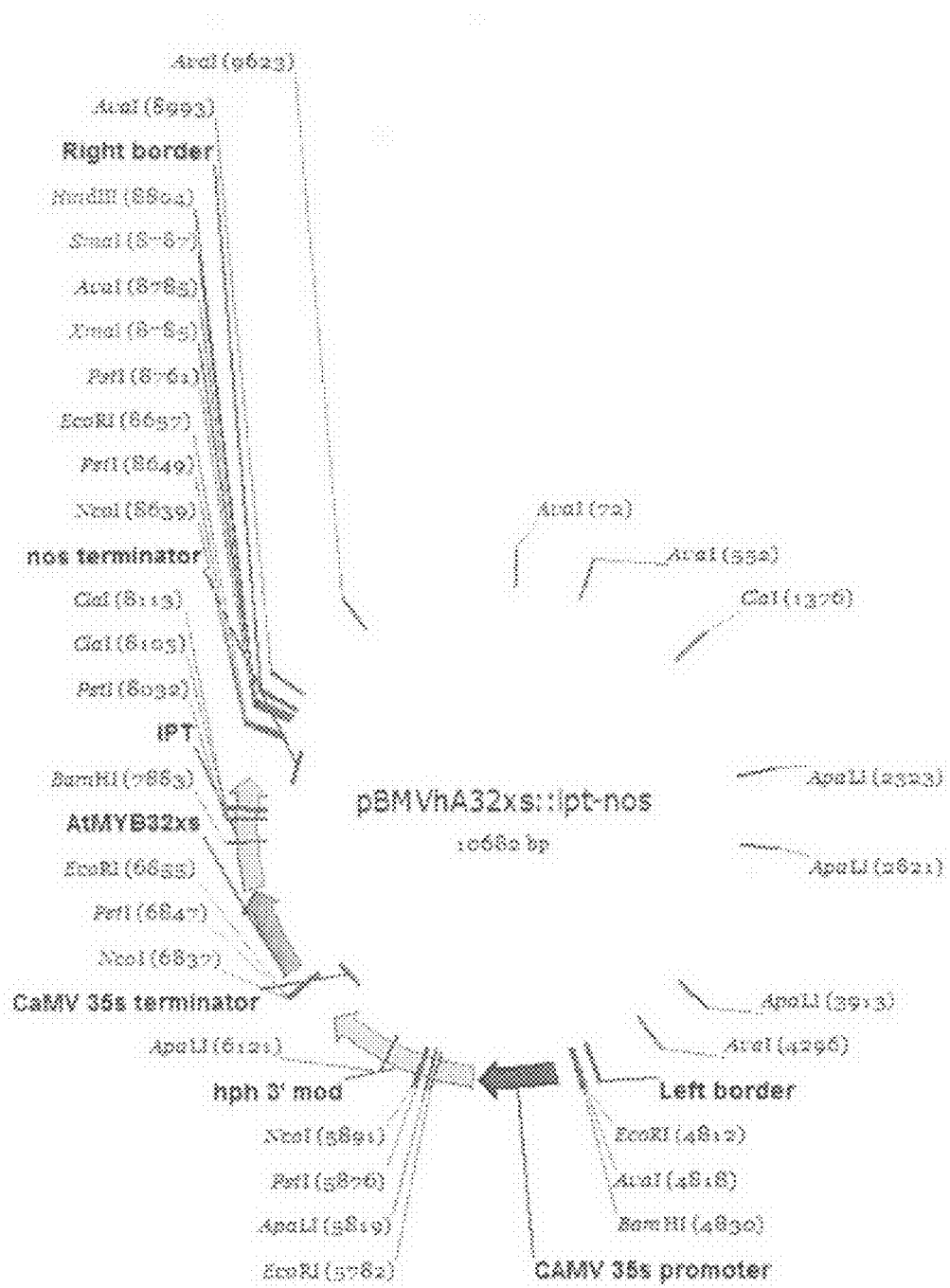

FIG. 22 shows vector details for pBMVhAtMYB32xs::ipt-nos [Gene: Isopentyl transferase (IPT); Vector: pBMVhAtMYB32XS::ipt-nos (backbone pPZPRCS2); Selectable marker: spec; Plant selectable marker cassette: 35S::hph::35ST; Gene promoter: AtMYB32-xs; Gene terminator: nos.].

FIG. 23 shows nucleotide sequence of vector pBMVhAtMYB32xs::ipt-nos (Sequence ID No. 14).

Figure 24:
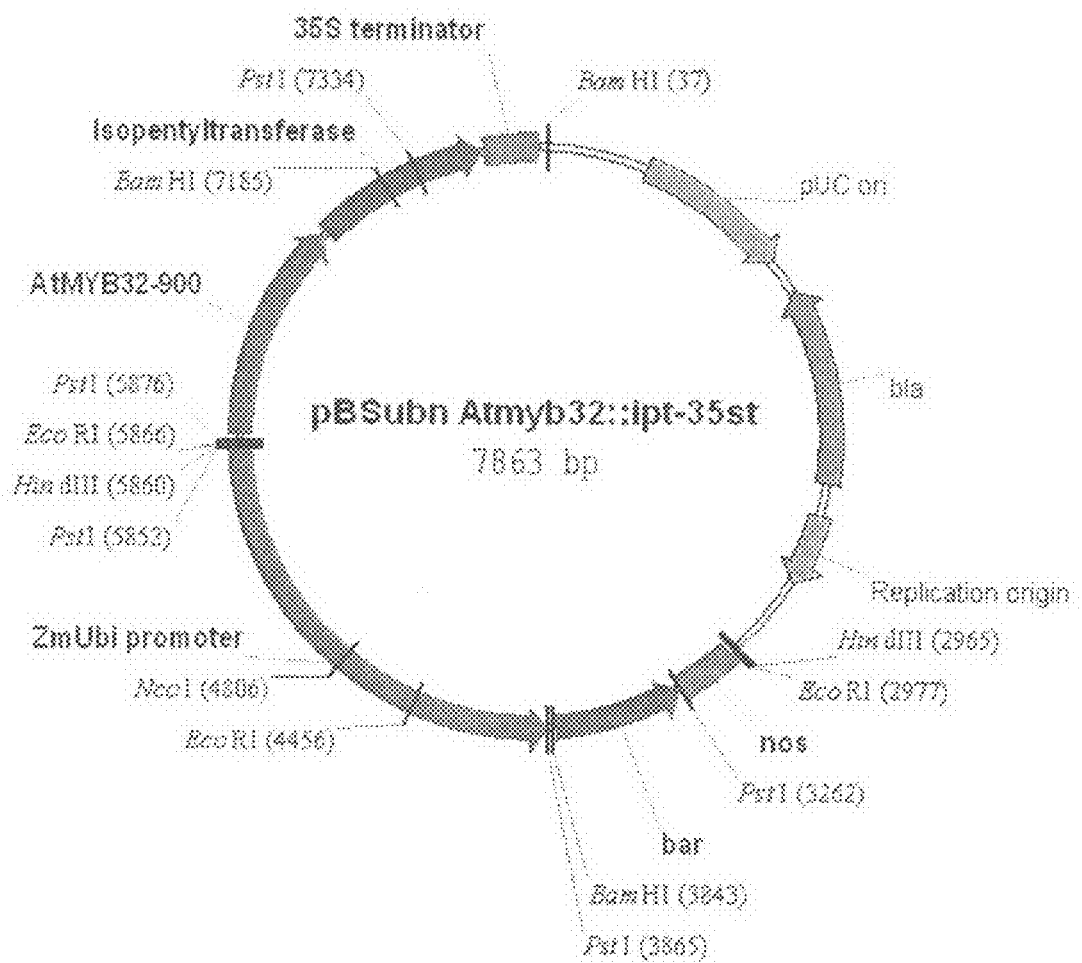
Figure 26A:
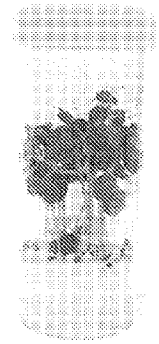
Figure 26B:
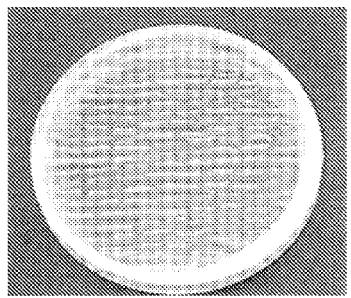
Figure 26C:
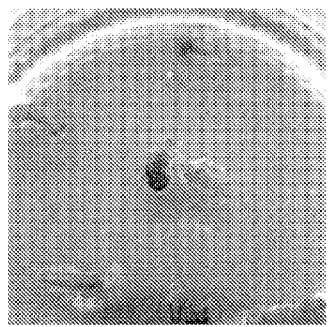
Figure 26D:
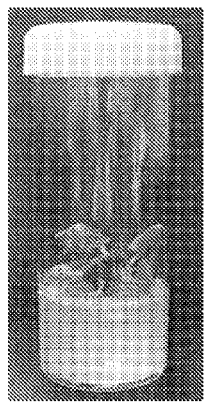
Figure 26E:
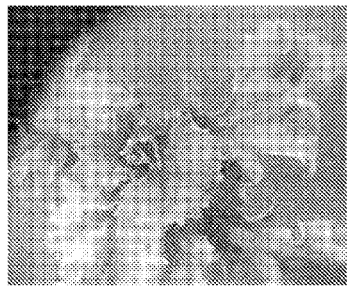
Figure 26F:
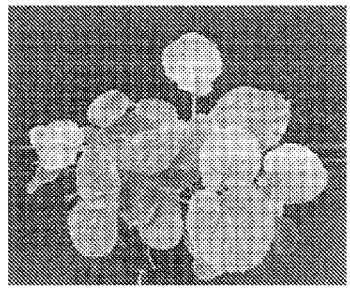
Figure 26G:
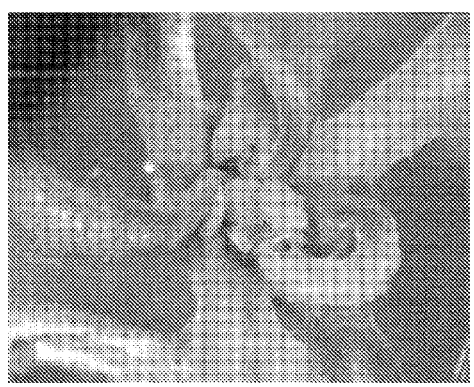
Figure 26H:
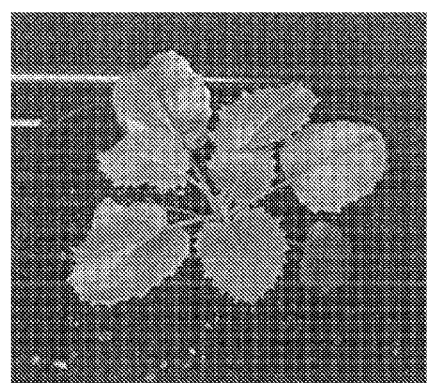
Figure 26I:
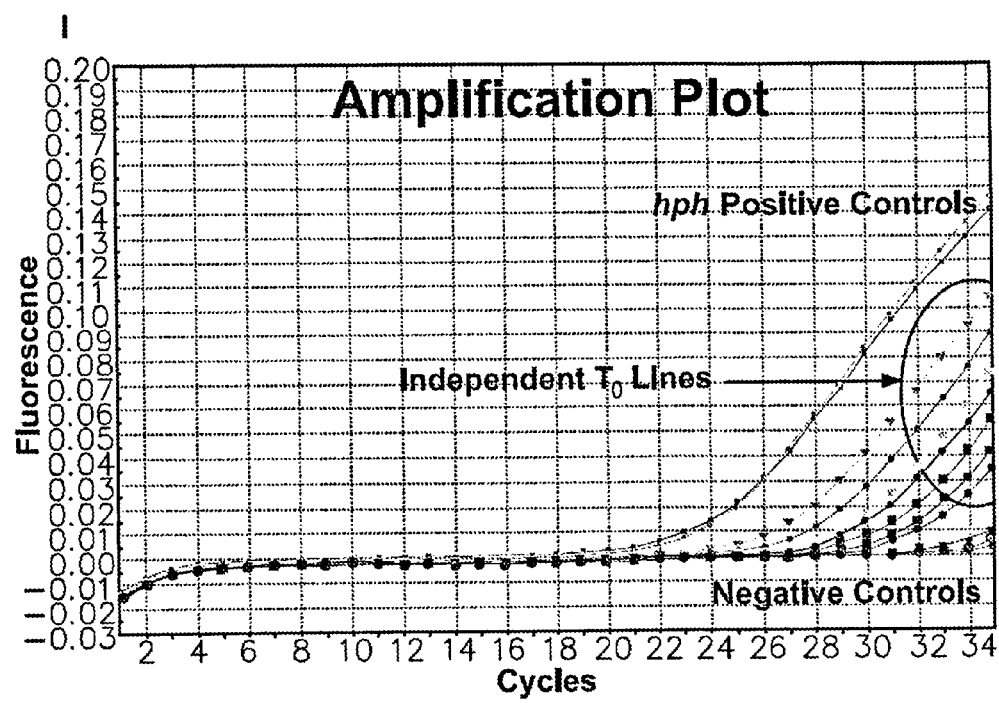
Figure 26J:

FIG. 24 shows vector details for pBSubn-AtMYB32-900::ipt-nos [Gene: Isopentyl transferase (IPT); Vector: pBSubn-AtMYB32-900::ipt-nos (backbone pPZPRCS2); Selectable marker: spec; Plant selectable marker cassette: Ubi::bar::nos; Gene promoter: AtMYB32-900; Gene terminator: nos.].

FIG. 25 shows nucleotide sequence of vector pBSAt-MYB32900::ipt-nos (Sequence ID No. 15).

FIG. 26 shows generation of transgenic canola containing the pBMVhATMYB3-900::ipt-nos and pBMVhATMYB32xs::ipt-nos. A. Canola seeds are germinated in vitro; B. Hypocotyl sections are excised from 7-day-old seedlings and inoculated with an *Agrobacterium* suspension; C & D. Regeneration from inoculated hypocotyl sections under hygromycin selection; E-J. Transgenic $T_0$ canola plants carrying the pBMVhATMYB3-900::ipt-nos and pBMVhATMYB32xs::ipt-nos vectors.

Figure 27:
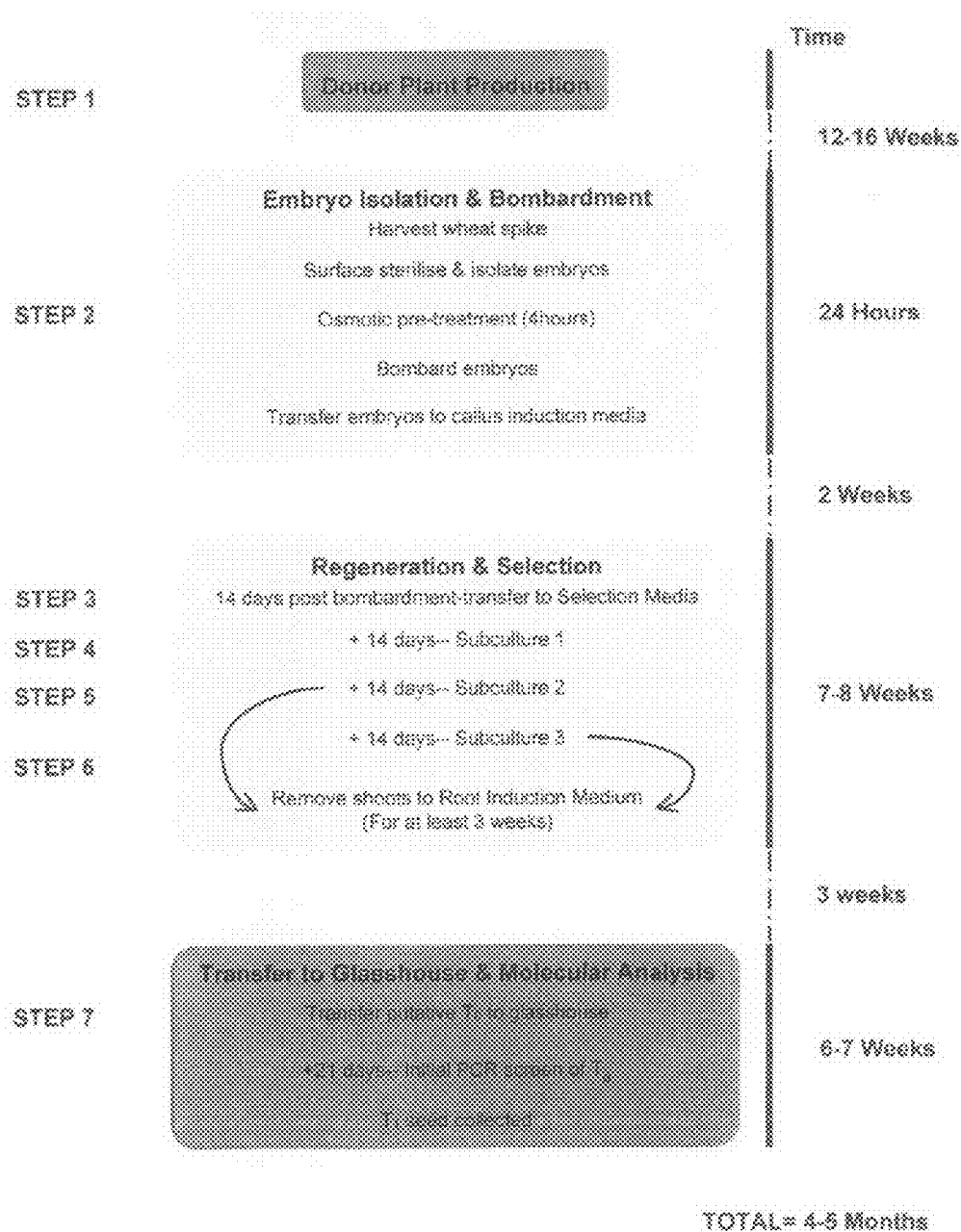

FIG. 27 shows a process for biolistic transformation of wheat.

Figure 28:
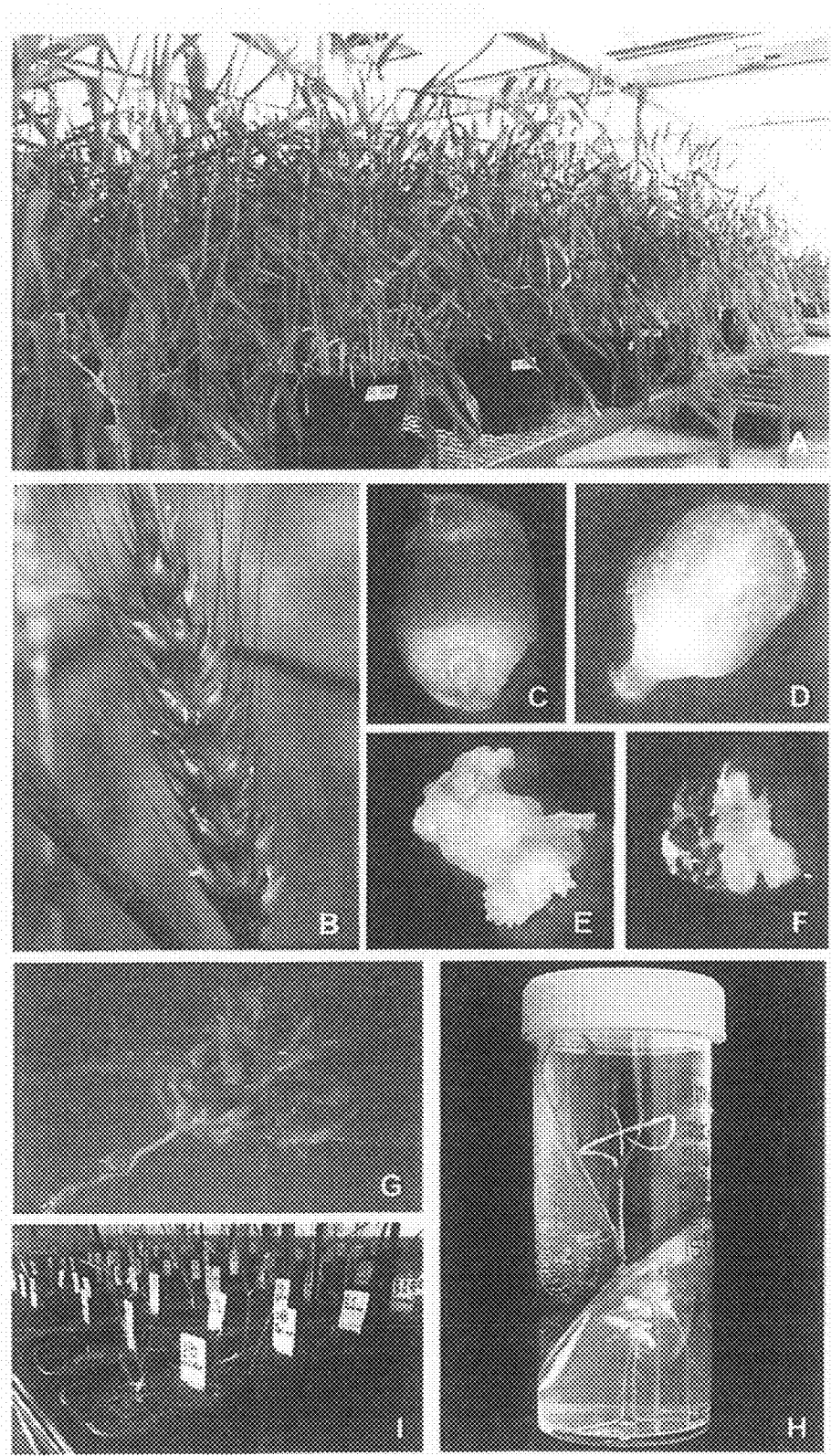

FIG. 28 shows biolistic transformation of wheat (*Triticum aestivum* L. MPB Bobwhite 26). Donor plant production (A & B); zygotic embryo isolation (C & D); Regeneration under glufosinate selection (E-G); Root formation under selection (H); $T_0$ plants growing under containment glasshouse conditions for recovery of transgenic offspring (I).

Figure 29:

FIG. 29 shows contained field trial of transgenic white clover plants expressing chimeric Atmyb32::ipt genes.

Figure 30:
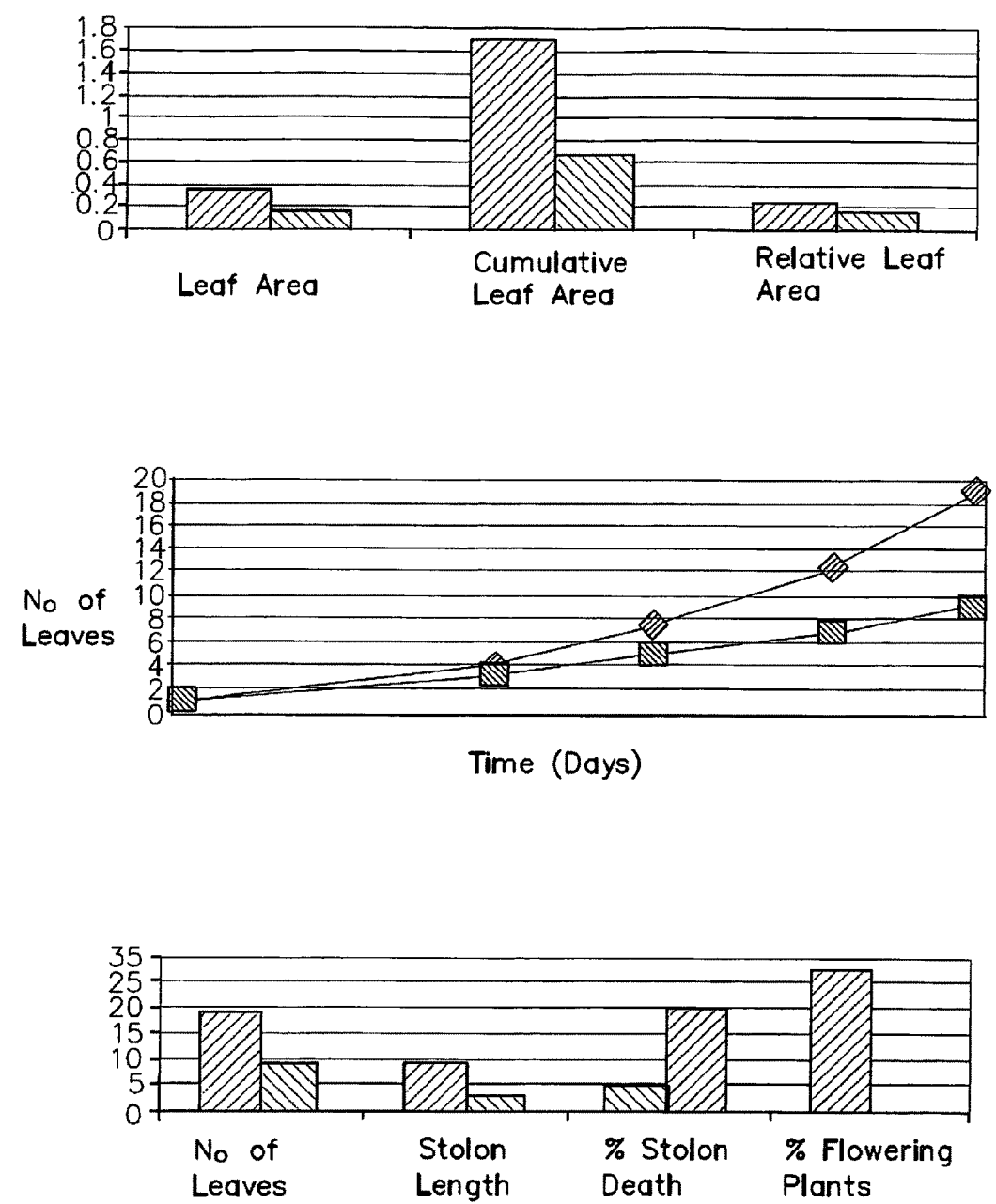

FIG. 30 shows comparative assessment of growth rates and growth dynamics of transgenic white clover plants expressing chimeric Atmyb32::ipt genes with non-transgenic control white clover plants. A) Growth Rates B) Growth Dynamics C) Growth Characteristics (after 45 days)

Figure 31:
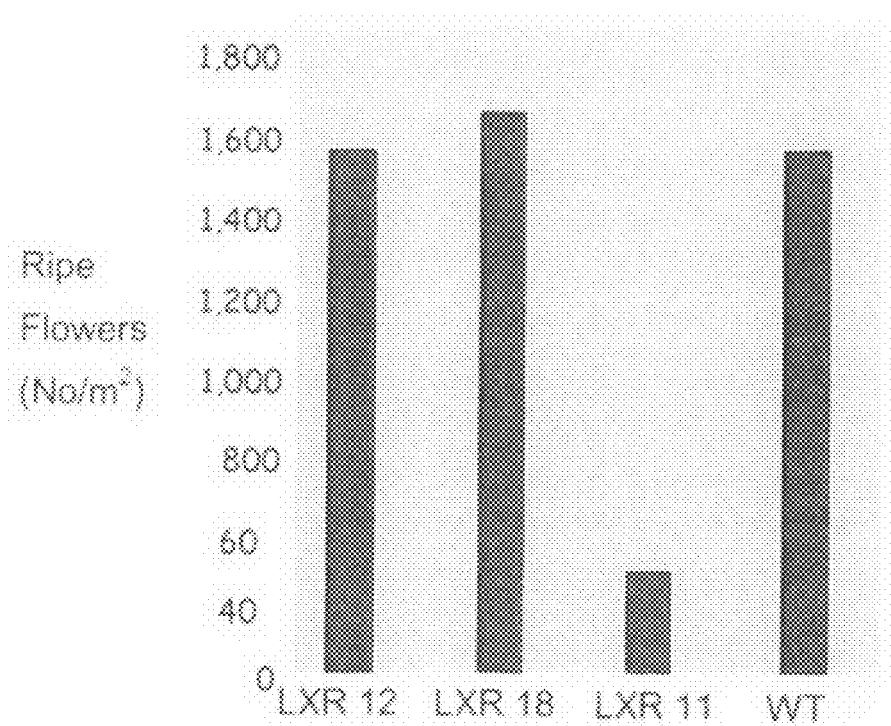

FIG. 31 shows flowering intensity (i.e. number of ripe flower per $m^2$) of transgenic white clover plants expressing chimeric Atmyb32::ipt genes (i.e. LXR 12, LXR 18 and LXR 11) and non-transgenic control white clover plants (i.e. WT) under contained field conditions.

Figure 32:
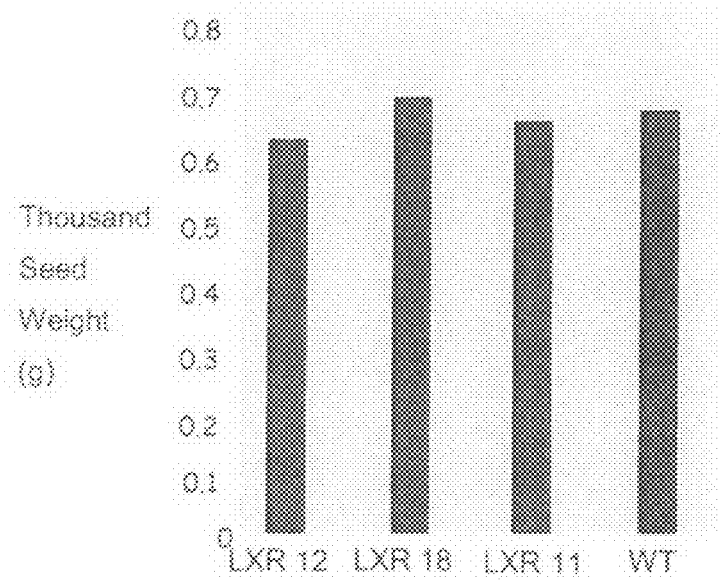

FIG. 32 shows seed weight (i.e. weight of thousand seeds, in grams) of transgenic white clover plants expressing chimeric Atmyb32::ipt genes (i.e. LXR 12, LXR 18 and LXR 11) and non-transgenic control white clover plants (i.e. WT) under contained field conditions.

Figure 33:
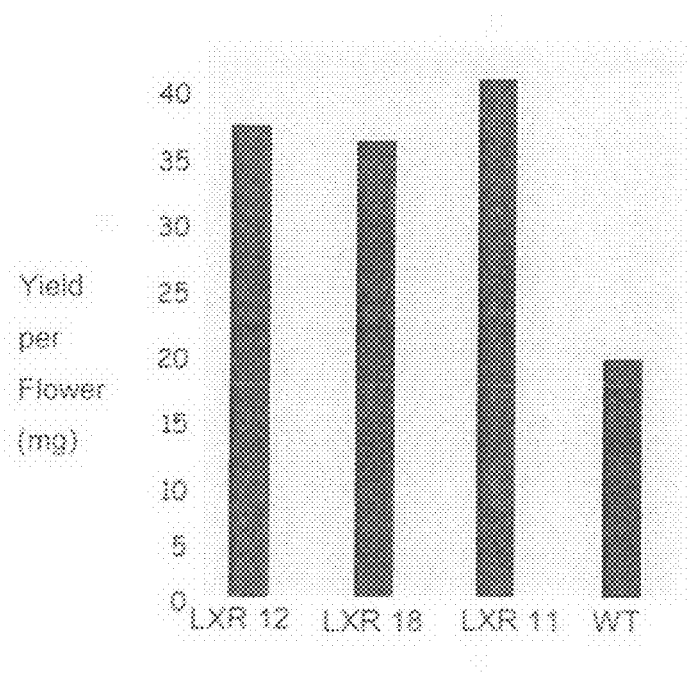

FIG. 33 shows seed yield per flower (in milligrams) of transgenic white clover plants expressing chimeric Atmyb32::ipt genes (i.e. LXR 12, LXR 18 and LXR 11) and non-transgenic control white clover plants (i.e. WT) under contained field conditions.

Figure 34:
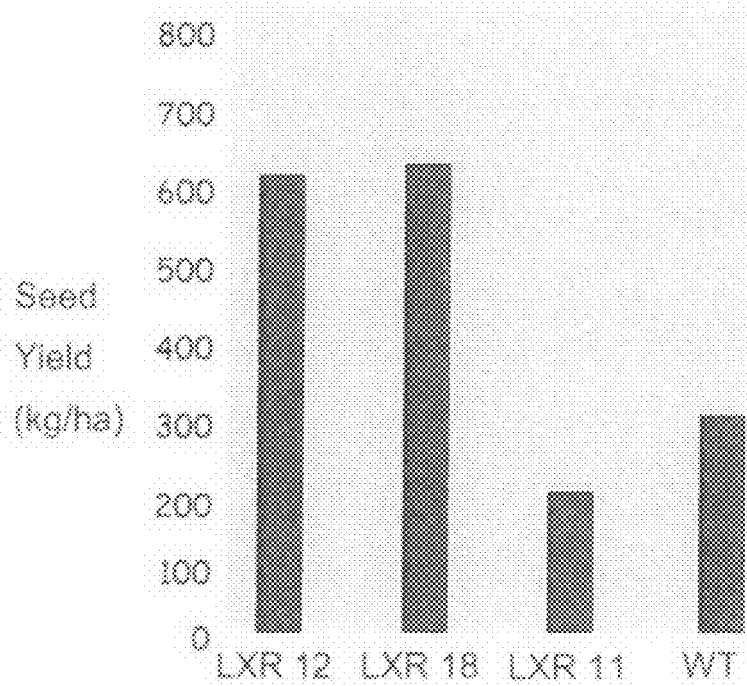

FIG. 34 shows seed yield per area (in kg/ha) of transgenic white clover plants expressing chimeric Atmyb32::ipt genes (i.e. LXR 12, LXR 18 and LXR 11) and non-transgenic control white clover plants (i.e. WT) under contained field conditions.

Figure 35:
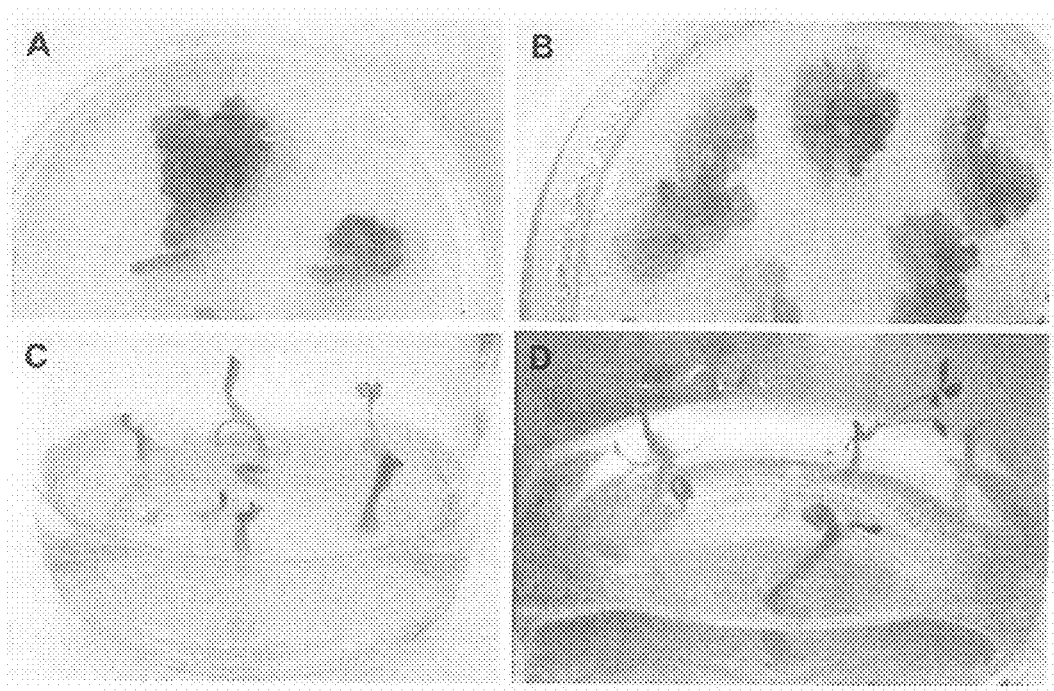

FIG. 35 shows generation of transgenic alfalfa plants containing the chimeric pBMVkATMYB3-900::ipt-nos and pBMVkATMYB32xs::ipt-nos genes A. Petiole explants from alfalfa clones C2-3, C2-4 and 19-17 are used for inoculation with an *Agrobacterium* suspension and lead to the production of transformed embryogenic calli following selection in presence of kanamycin; B-D. Regeneration of transgenic alfalfa plantlets carrying chimeric genes from pBMVkATMYB3-900::ipt-nos and pBMVkATMYB32xs::ipt-nos vectors, from somatic embryos grown in vitro.

Figure 36:
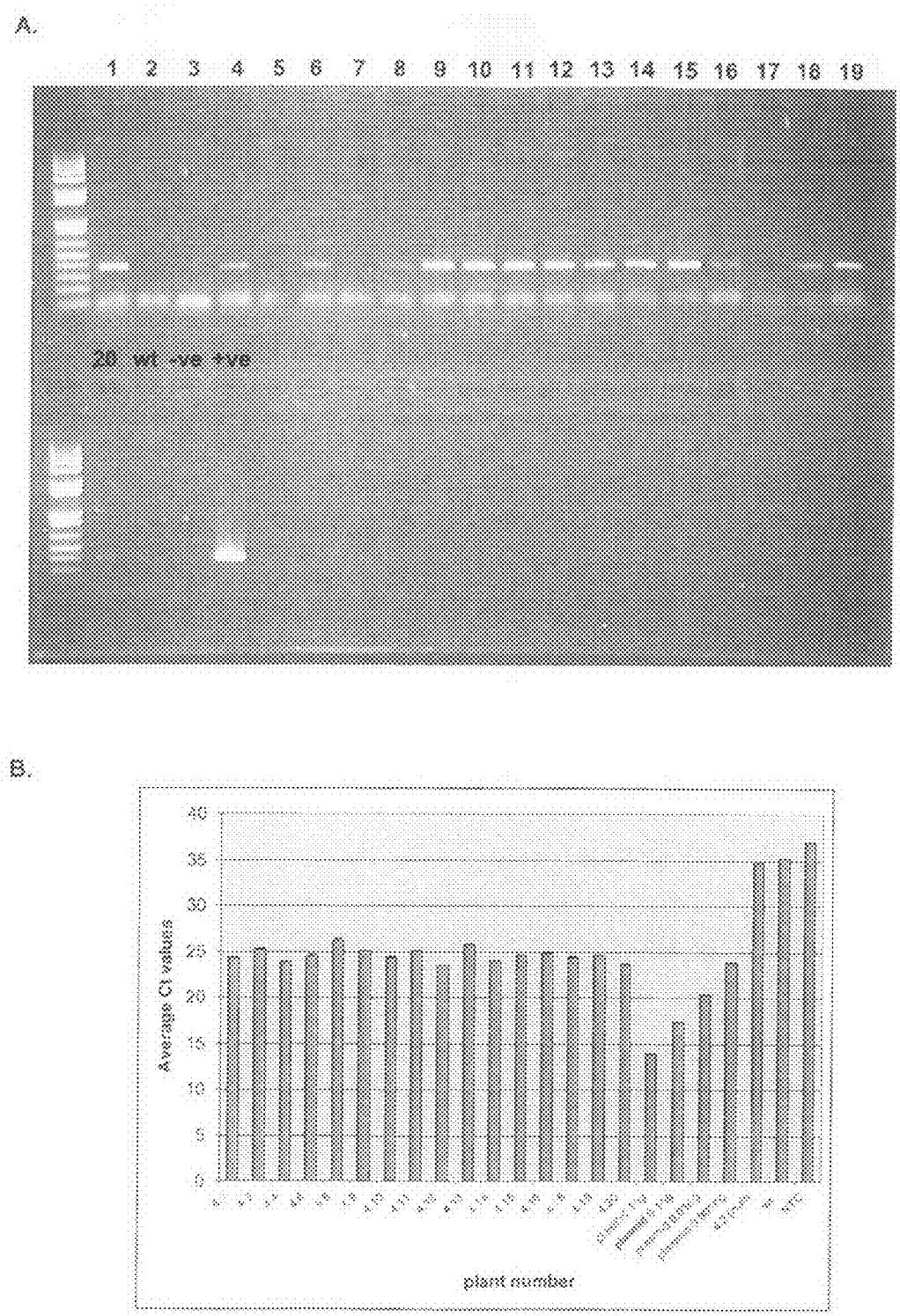

FIG. 36 shows PCR analysis of transgenic canola plants (T1 LXR canola plants Line 4). Genomic DNA was isolated from different transgenic canola plants of $T_1$ LXR04 lines and subjected to PCR using primers specific for A. the selectable marker (hph) or B. the candidate gene of interest (IPT).

Figure 37:
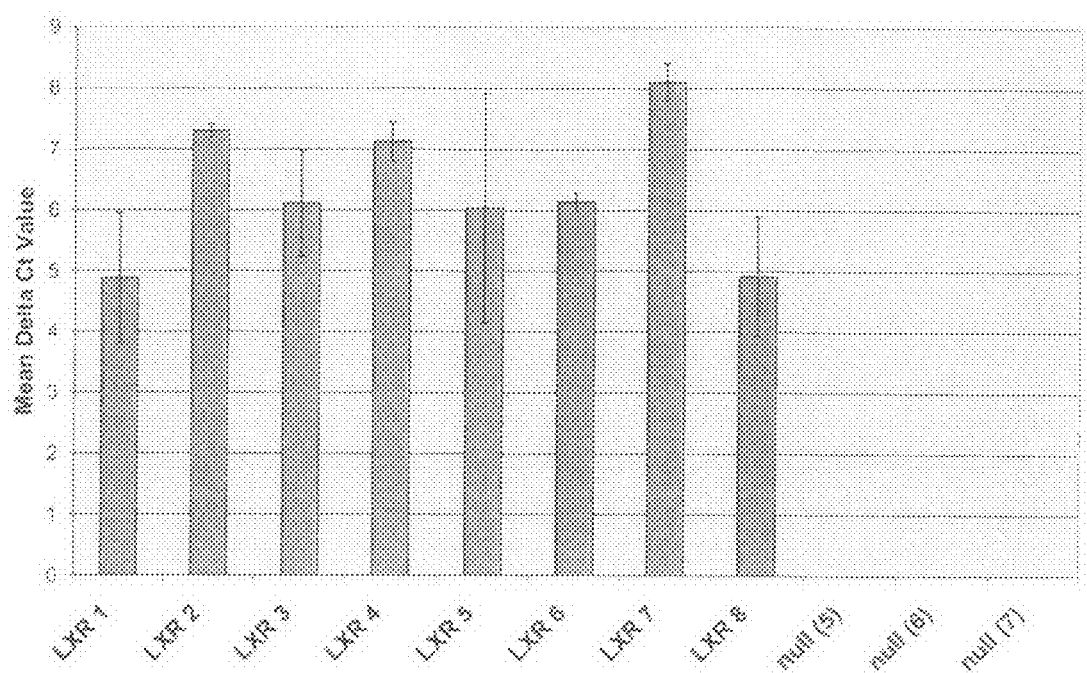

FIG. 37 shows expression analysis of the IPT gene in $T_1$ transgenic canola plants (T1 LXR canola relative IPT leaf expression).

Figure 38:
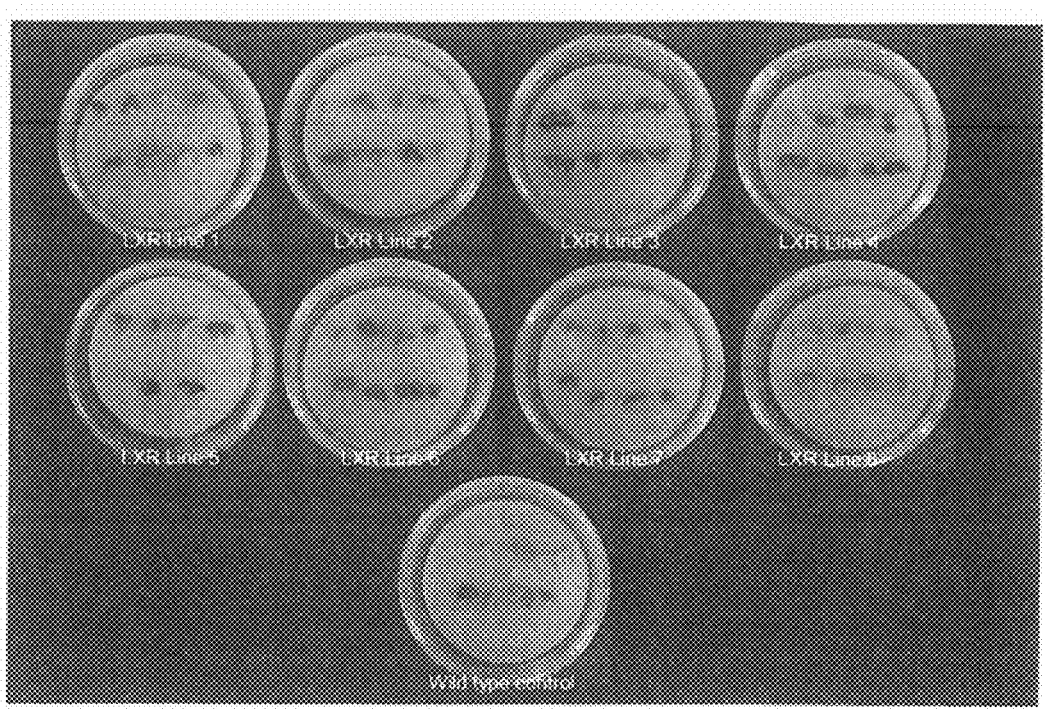

FIG. 38 shows transgenic canola displaying delay of detached cotyledon senescence as compared to wild-type control cotyledons 7 days following detachment.

Figure 39:
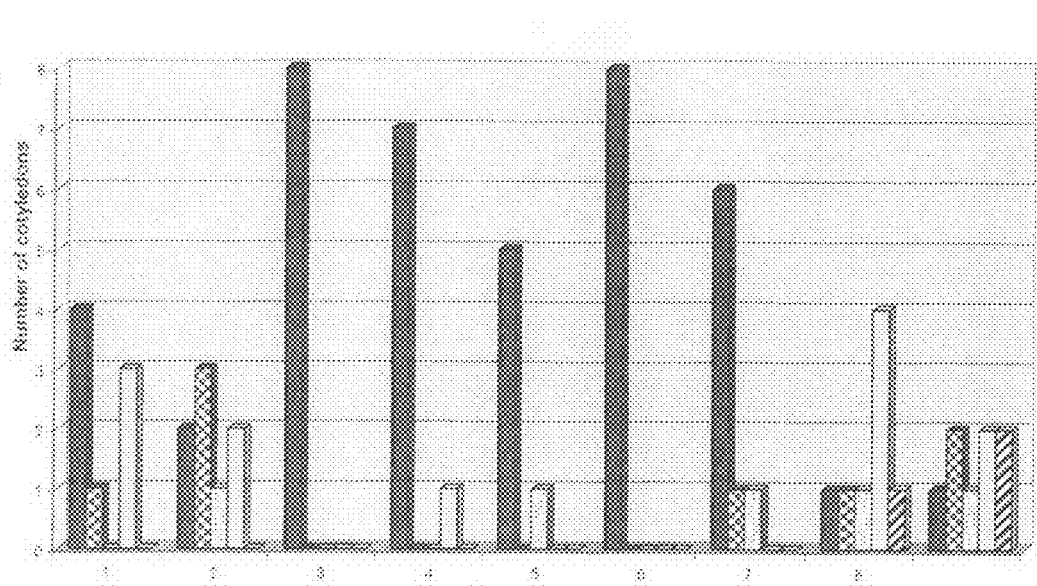

FIG. 39 shows the senescence score of $T_1$ transgenic canola cotyledons at 7 days following detachment.

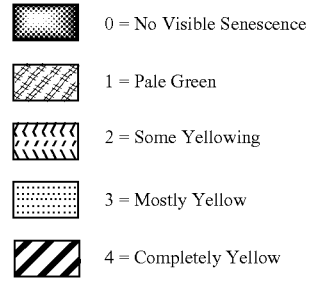

Figure 40:
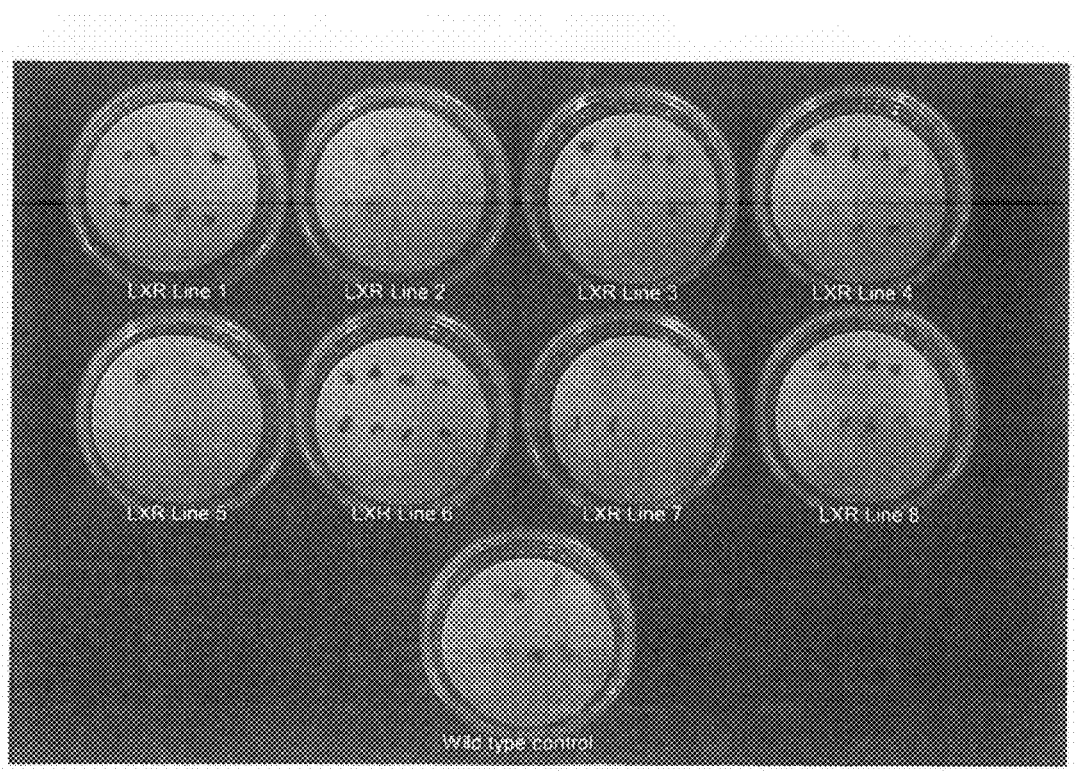

FIG. 40 shows transgenic canola displaying delay of detached juvenile leaf senescence as compared to wild-type control cotyledons 14 days following detachment.

Figure 41:
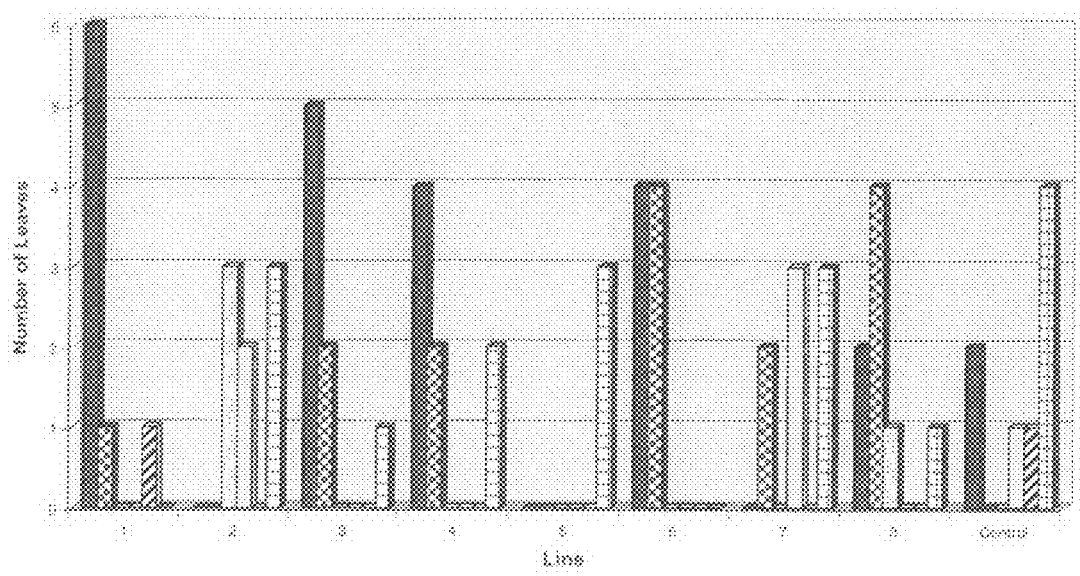

FIG. 41 shows senescence score of $T_1$ transgenic canola juvenile first leaves at 14 days following detachment.

Figure 42:
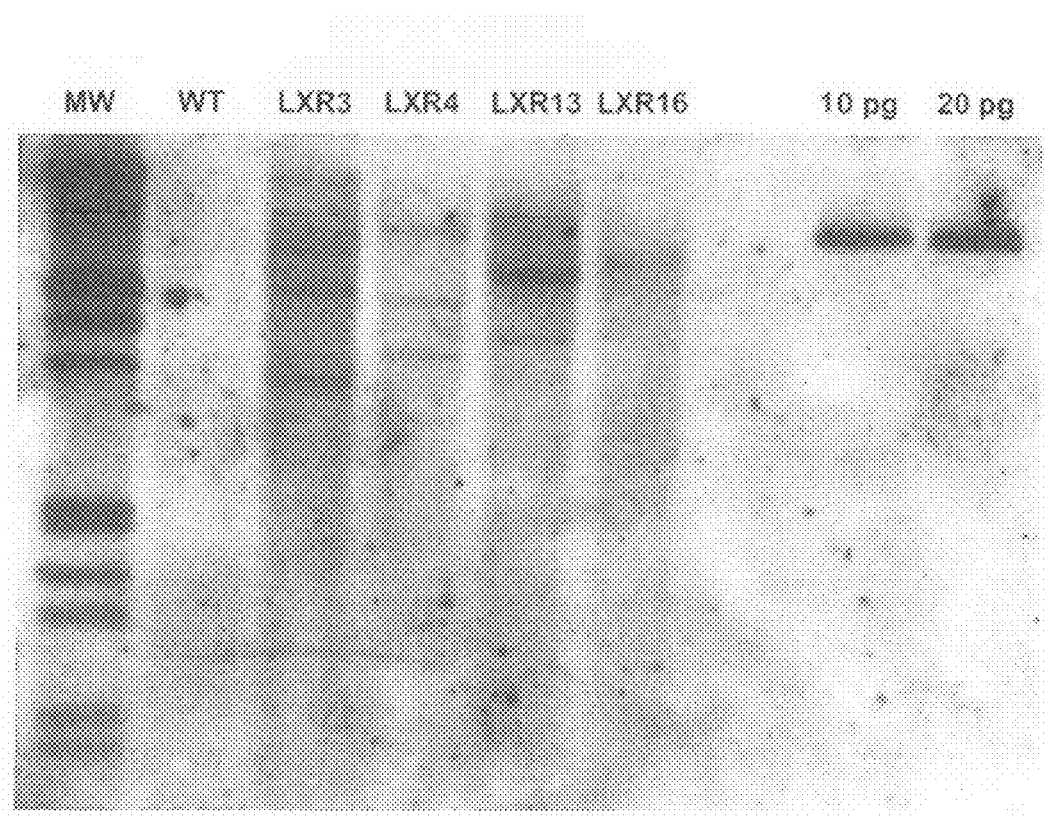

FIG. 42 shows Southern hybridisation analysis of transgenic wheat lines. Lanes include: MW—molecular weight; WT—wild-type; Transgenic wheat lines LXR3, LXR4, LXR13, LXR16 and positive plasmid controls containing 10 and 20 pg.

Figure 43:
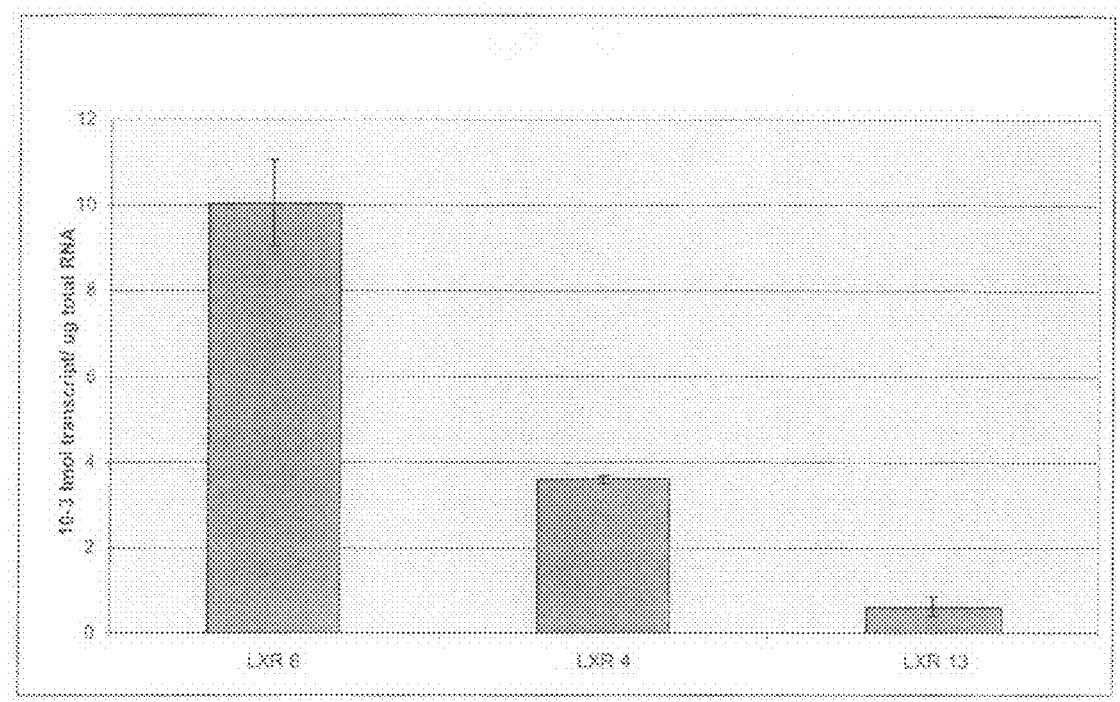

FIG. 43 shows expression analysis of independent $T_1$ transgenic wheat lines (IPT quantitative expression in wheat). Quantitative transcript values were determined in femtomoles (fmol) per microgram of RNA using a standard curve derived from plasmid DNA containing the target sequence. Samples represent high, medium and low expression classes for candidate gene IPT.

Figure 44:
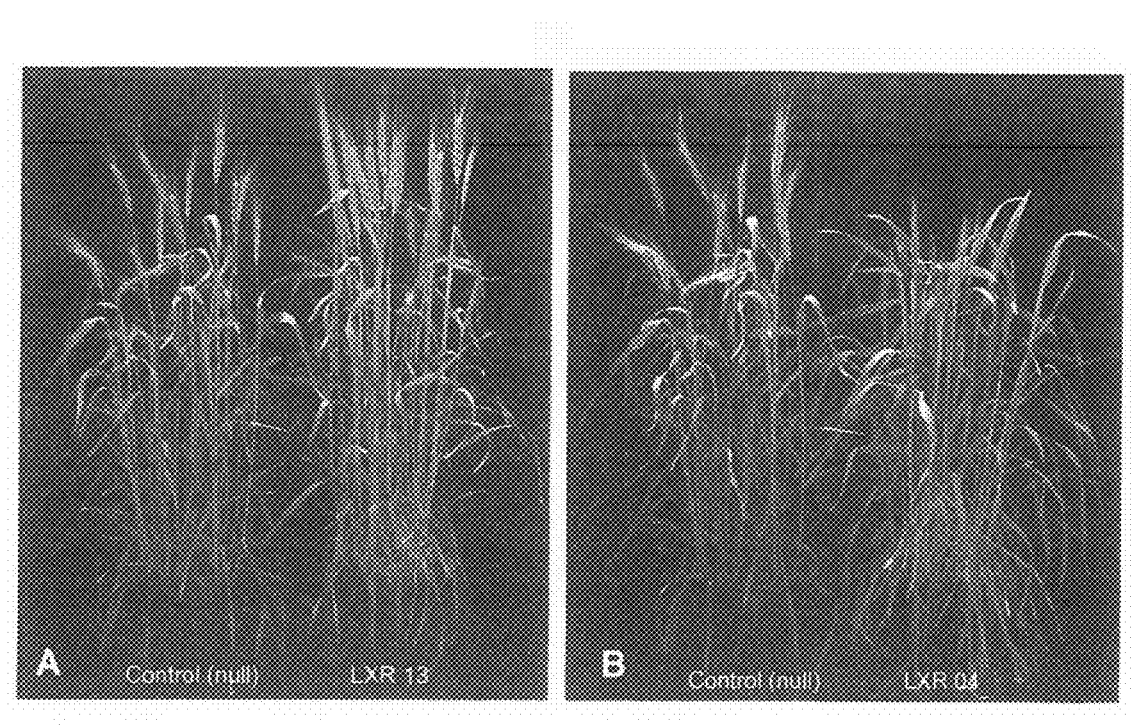

FIG. 44 shows phenotypic variation of glasshouse grown $T_1$ transgenic wheat plants. A. $T_1$ LXR 13 wheat plants displaying normal phenotype as compared to null control wheat plants. B. $T_1$ LXR 04 wheat plants displaying stunted phenotype and increased flag leaf number as compared to null control wheat plants.

Figure 45:
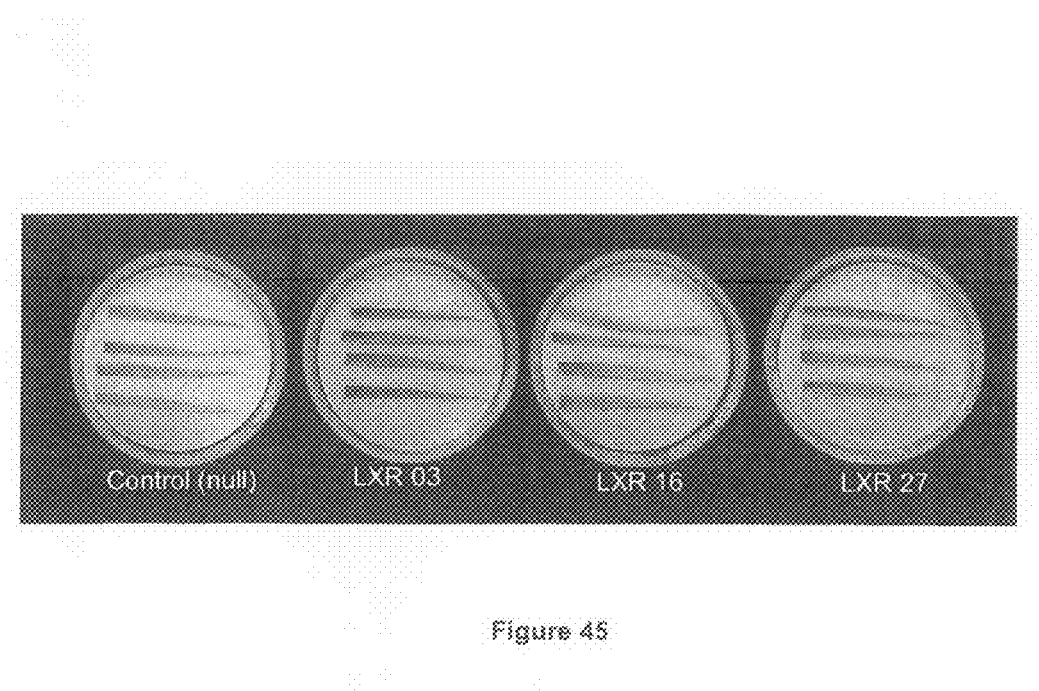

FIG. 45 shows transgenic wheat displaying delay of leaf senescence as compared to null control leaves 7 days following detachment.

Figure 46:
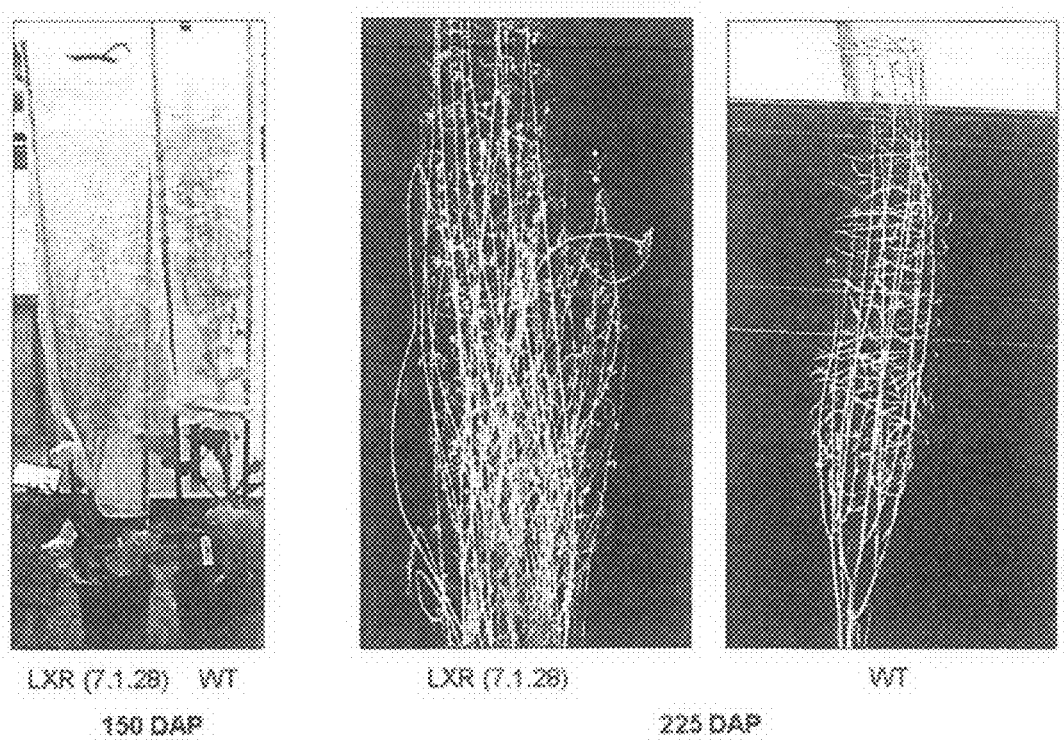

FIG. 46 shows phenotypes of the T2 transgenic canola plants expressing the chimeric atmyb32::ipt transgene (i.e. LXR lines), compared to wild-type non-transgenic control canola plants (i.e. WT), 150 DAP (left) and 225 DAP (right).

Figure 47:
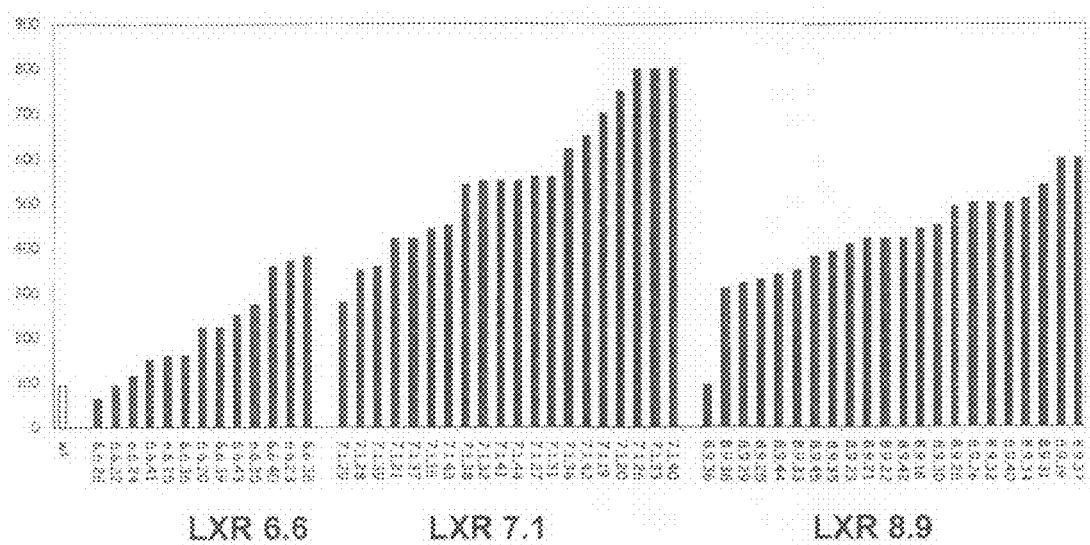

FIG. 47 shows flowering intensity in transgenic canola plants expressing the chimeric atmyb32::ipt transgene (i.e. LXR lines), compared to wild-type non-transgenic control canola plants (i.e. WT).

Figure 48:
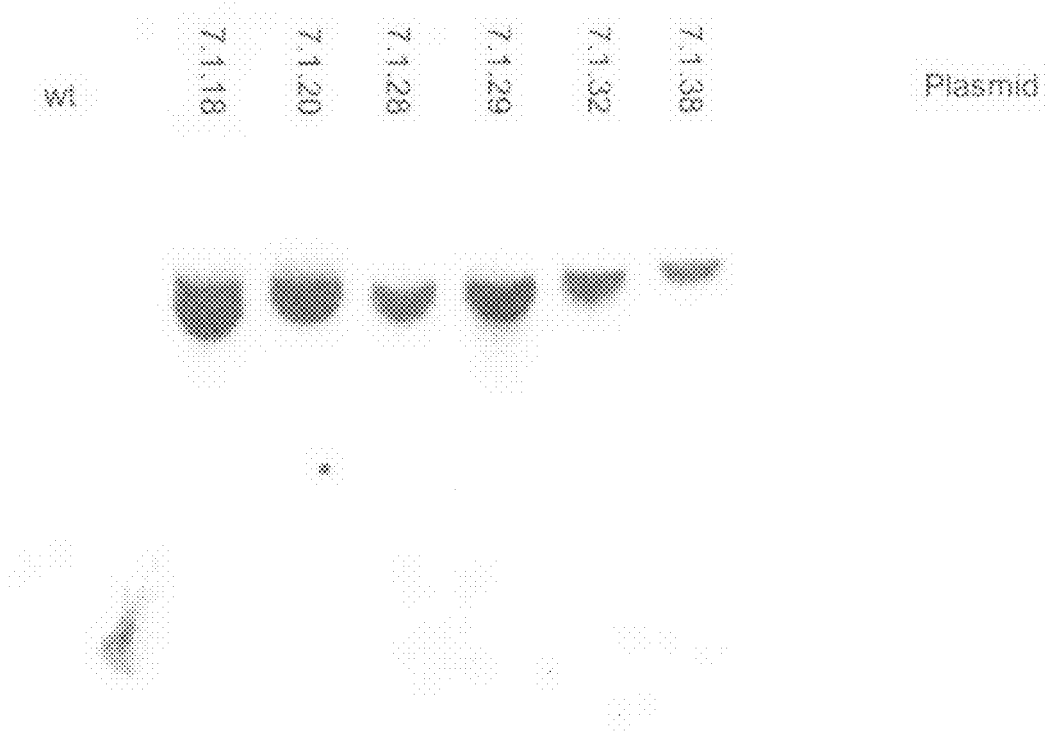

FIG. 48 shows southern hybridisation analyses of T2 transgenic canola lines (i.e. LXR 7.1 lines) expressing the chimeric atmyb32::ipt transgene. WT: wild-type, negative, non-transgenic control.

Figure 49:
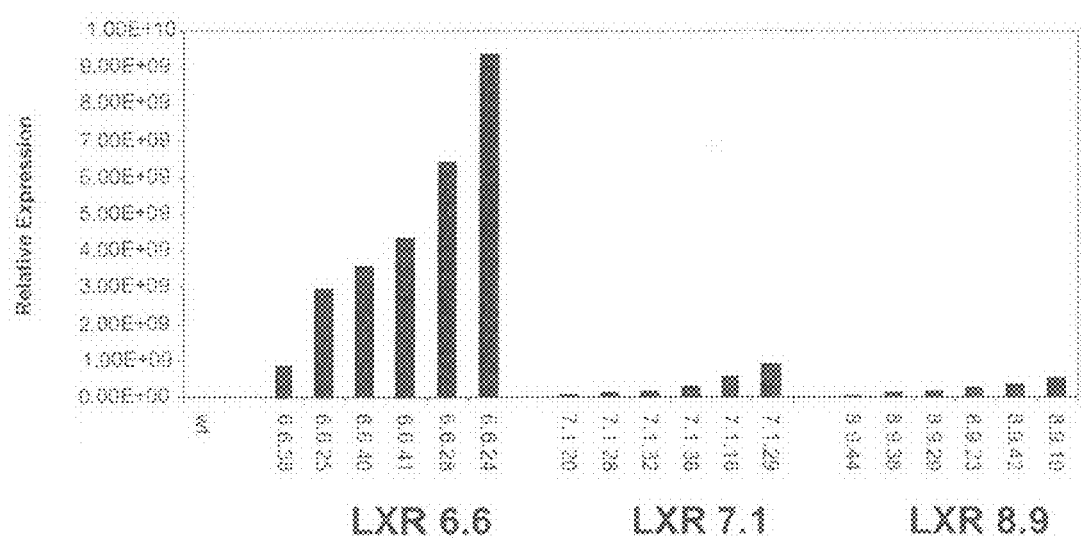

FIG. 49 Relative expression level of atmyb32::ipt transgene in T2 transgenic canola lines (i.e. LXR 6.6-, 7.1- and 8.9 T2 lines). WT: wild-type, negative, non-transgenic control.

Figure 50:
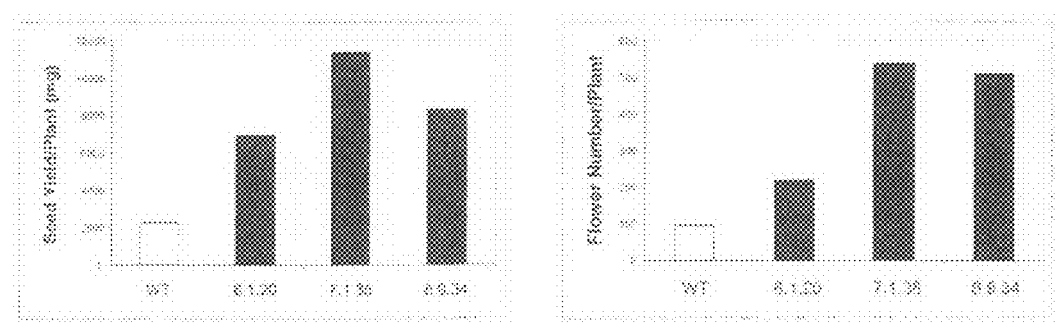

FIG. 50 Flowering intensity and seed yield in T2 transgenic canola lines expressing the chimeric atmyb32::ipt transgene (i.e. lines 6.6-, 7.1- and 8.9) compared to wild-type, negative, non-transgenic control (i.e. WT).

Figure 51:
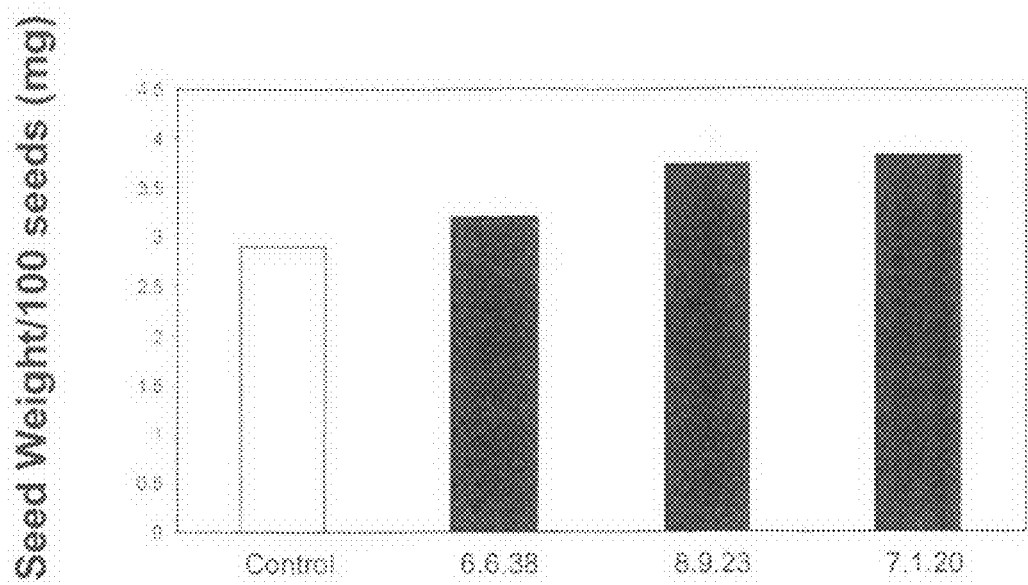

FIG. 51 Seed weight of T2 transgenic canola lines expressing the chimeric atmyb32::ipt transgene (i.e. lines 6.6-, 7.1- and 8.9) compared to wild-type, negative, non-transgenic control (i.e. WT).

EXAMPLES

Example 1

Atmyb32 Promoter Sequence and Promoter Sequence Variants

The Atmybb32 promoter sequence and variants thereof are shown in FIGS. 1-4.

Example 2

Cytokinin Biosynthesis Genes

Examples of cytokinin biosynthesis genes suitable for use in the present invention are shown in FIGS. 6, 8 and 10. Suitable genes also include those encoding the polypeptides shown in FIGS. 7, 9 and 11.

Example 3

Production of Transgenic White Clover Plants

Transgenic white clover plants (*Trifolium repens* cv. Haifa and Irrigation) were produced by *Agrobacterium*-mediated transformation using a binary vector carrying the chimeric atmyb32::ipt gene (FIG. 12*a*). The transgenic plants were screened by PCR using ipt and nptll primers (FIG. 12*b*). HindIII digested genomic DNA samples subjected to Southern DNA hybridization analysis showed that the DNA fragments greater than 4.4 kb were detected in all lanes by both ipt and nptII probes, demonstrating the presence and integration of full-length T-DNA into the white clover genome (FIG. 12). Transgenic lines Hmi01, Imi06, Imi11, and Imi18 (Lane 1, 3, 5, 8 and 12 respectively) appeared to have a single copy of full-length T-DNA integrated in the genome. Other transgenic lines had multiple copies of the atmyb32::ipt transgene.

Example 4

IPT Gene Expression in Transgenic White Clover Plants

The expression of the atmyb32::ipt transgene in transgenic white clover (*T. repens*) plants was assessed by RT-PCR. The ipt mRNA was detected in leaf tissues of all atmyb32::ipt transgenic white clover plants examined, with varying levels of PCR products detected (FIG. 13).

Example 5

Delayed Detached Leaf Senescence in Transgenic White Clover Plants

Experiments were performed to assess detached leaf senescence of atmyb32::ipt transgenic plants. Rapid yellowing was observed in detached leaves from non-transformed and atmyb32::gusA transgenic white clover plants of both cultivars within one week. Transgenic lines Hmi01, Hmi08, Imi16 and Imi18 showed delayed senescence while Imi11 and Imi12 showed no sign of yellowing by the end of 7 days. After two weeks, the leaves of all atmyb32::ipt transgenic plants were much greener than those of non-transformed and atmyb32::gusA control transgenic plants (FIG. 14). The degree of senescence in excised leaves was in the order HC, Hmg>Hmi01>Hmi08 for cv. Haifa, and IC and Img>Imi16>Imi18>Imi11 and Imi12 for cv. Irrigation. HC is Haifa untransformed control, Hmg is Haifa atmyb32::gusA control, IC is Irrigation untransformed control, Img is Irrigation atmyb32::gusA control. Hmi01, Hmi08, Imi16, Imi18, Imi11 and Imi12 are independent atmyb32::ipt transgenic white clover plants from the cultivar Haifa (H) and Irrigation (I), respectively.

Example 6

Plant Morphology and Root Development in Transgenic White Clover Plants

Normal plant morphology as well as normal shoot and normal root development was observed in atmyb32:ipt transgenic white clover plants (FIG. 6), thus indicating that the regulated expression of the ipt gene under control of the atmyb32 promoter did not negatively affect neither rooting nor apical dominance of the transgenic white clover plants (Table 1).

TABLE 1

| Transformant | Cultivar | Construct | ipt copy No | Phenotype |
|---|---|---|---|---|
| Hmi01 | Haifa | Atmyb32::ipt | 1 | Normal |
| Hmi08 | Haifa | Atmyb32::ipt | >3 | Normal |
| Imi06 | Irrigation | Atmyb32::ipt | 1 | Normal |
| Imi07 | Irrigation | Atmyb32::ipt | 3 | Normal |
| Imi09 | Irrigation | Atmyb32::ipt | >3 | Normal |
| Imi10 | Irrigation | Atmyb32::ipt | >3 | Normal |
| Imi11 | Irrigation | Atmyb32::ipt | 1 | Normal |

TABLE 1-continued

| Transformant | Cultivar | Construct | ipt copy No | Phenotype |
|---|---|---|---|---|
| Imi12 | Irrigation | Atmyb32::ipt | 2 | Normal |
| Imi16 | Irrigation | Atmyb32::ipt | 2 | Normal |
| Imi18 | Irrigation | Atmyb32::ipt | 1 | Normal |

Normal plant morphology and normal rooting was observed in ten independent atmyb32::ipttransgenic white clover lines analysed. Estimated ipt gene copy numbers in the ten independent atmyb32::ipttransgenic white clover lines are shown.

Example 7

Generation of Vectors for Plant Transformation

Four binary vectors have been generated for *Agrobacterium*-mediated transformation of plants (FIGS. 16-19). Each vector has a pPZP200 vector backbone (Hajdukiewicz et al., 1994) and contains either chimeric Atmyb32-900::ipt-nos or Atmyb32-xs::ipt-nos with or without a chimeric 35S::nptII-35st or 35S::hph-35st selectable marker cassettes.

One transformation vector has been constructed for biolistic transformation (FIGS. 20 and 21). The transformation vector contains chimeric Atmyb32-900::ipt-35st with a chimeric Ubi::bar-nos selectable marker cassette.

The Atmyb32 promoter, promoter variant Atmyb32xs, the isopentyl transferase gene and terminators 35st and nos were amplified by PCR using Gateway™ (Invitrogen) adapted primers and cloned into a pDONR221 entry vectors. These were subsequently cloned using recombination into destination vectors containing the conventionally cloned selectable marker cassettes. All vectors were fully sequenced following strict quality assurance protocols.

Example 8

*Agrobacterium*-mediated Transformation of Canola (*Brassica napus*)

Binary vectors pBMVhATMYB3-900::ipt-nos (FIG. 20) and pBMVhATMYB32xs::ipt-nos (FIG. 22) containing chimeric ipt genes under control of Atmyb32 promoter (FIG. 1) and Atmyb32xs variant promoter sequence with deleted root-specific motifs (FIG. 2) were used for *Agrobacterium*-mediated transformation of *Brassica napus* hypocotyl segments (FIG. 26).

*Brassica napus* seeds are surface sterilised in 70% ethanol for 2 minutes, washed 3 times in sterile water then further surface sterilised in a solution containing 1% (w/v) Calcium hypochlorite and 0.1% (v/v) Tween 20 for 30 minutes. The seeds are washed at least 3 times in sterile water and planted in 120 ml culture vessels containing a solidified germination medium containing 1× Murashige and Skoog (Murashige and Skoog *Physiol. Plant,* 15: 473-497, 1962) macronutrients, 1× micronutrients and B5 organic vitamins, supplemented with 500 mg/L MES, 2% (w/v) sucrose at a pH of 5.8 with the addition of 4 g/L Gelrite. The vessels are incubated at 25° C. under 16 h light/8 h dark conditions for 7 days to encourage germination.

After 7 days, seedlings of *Brassica napus* (whole seedlings) are transferred to a liquid medium consisting of 1× Murashige and Skoog macronutrients, 1× micronutrients and B5 organic vitamins, supplemented with 500 mg/L MES, 3% (w/v) sucrose at a pH of 5.8. Seedlings are grouped together and the roots and cotyledons removed prior to cutting the hypocotyls into 7-10 mm sections and plating on 9×1.5 cm petri dishes containing a preconditioning medium consisting of 1× Murashige and Skoog macronutrients, 1× micronutrients and B5 organic vitamins, supplemented with 500 mg/L MES, 3% (w/v) sucrose at a pH of 5.8 solidified with 6.4 g/l Bacto-Agar.

Hypocotyl sections are cultured for 24 hours prior to inoculation with an *Agrobacterium* suspension $OD_{600}$=0.2 for 30 minutes consisting of 1× Murashige and Skoog macronutrients, 1× micronutrients and B5 organic vitamins, supplemented with 500 mg/L MES, 100 μM Acetosyringone, 3% (w/v) sucrose at a pH of 5.8.

Following inoculation, hypocotyl sections are blotted on sterile paper towels and transferred to 9×1.5 cm petri dishes containing 1× Murashige and Skoog macronutrients, 1× micronutrients and B5 organic vitamins, supplemented with 500 mg/L MES, 100 μM Acetosyringone, 1 mg/L 2,4-D, 3% (w/v) sucrose at a pH of 5.8 solidified with 8 g/l Bacto-Agar. Explants are incubated at 25° C. under 16 h light/8 h dark conditions for 72 hours for co-cultivation.

Following co-cultivation, 20-30 hypocotyl explants are transferred to 9×1.5 cm petri dishes containing a solidified selection medium consisting of 1× Murashige and Skoog macronutrients, 1× micronutrients and B5 organic vitamins, supplemented with 500 mg/L MES, 1 mg/L 2,4-D, 3% (w/v) sucrose at a pH of 5.8 solidified with 8 g/l Bacto-Agar, supplemented with 250 mg/l timentin and 10 mg/l hygromycin to select for hygromycin-resistant shoots. Plates are incubated at 25° C. under 16 h light/8 h dark conditions.

After 7 days hypocotyl explants are transferred to 9×2.0 cm petri dishes containing a solidified regeneration media consisting of 1× Murashige and Skoog macronutrients, 1× micronutrients and B5 organic vitamins, supplemented with 500 mg/L MES, 1 mg/L 2,4-D, 3% (w/v) sucrose at a pH of 5.8 solidified with 8 g/l Bacto-Agar, supplemented with 4 mg/l BAP, 2 mg/l Zeatin, 5 mg/l Silver Nitrate, 250 mg/l timentin and 10 mg/l hygromycin. Plates are incubated under direct light at 25° C. under fluorescent light conditions (16 hr light/8 hr dark photoperiod; 55 μmol $m^{-2}$ $sec^{-1}$) for 4 weeks to encourage shoot development.

Regeneration is monitored weekly and hypocotyl explants transferred to fresh 9×2.0 cm petri dishes containing solidified regeneration media, RM supplemented with 4 mg/l benzyladenine, 2 mg/l zeatin, 5 mg/l silver nitrate, 250 mg/l timentin and 10 mg/l hygromycin for 6-8 weeks to encourage shoot development.

Hygromycin-resistant ($Hyg^r$) shoots are transferred to 120 ml vessels containing solidified root induction medium, RIM1, consisting of 1× Murashige and Skoog macronutrients, 1× micronutrients and B5 organic vitamins, supplemented with 500 mg/L MES, 1 mg/L 2,4-D, 1% (w/v) sucrose at a pH of 5.8 solidified with 8 g/l Bacto-Agar supplemented with 250 mg/l timentin. Shoots are incubated under direct fluorescent light at 25° C. (16 hr light/8 hr dark photoperiod; 55 μmol $m^{-2}$ $sec^{-1}$) to encourage shoot elongation and root development over 4-5 weeks. All $Hyg^r$ shoots with developed shoot and root systems are transferred to soil and grown under glasshouse conditions.

Example 9

Biolistic Transformation of Wheat (*Triticum aestivum* L.)

Transformation vectors containing chimeric ipt genes under control of Atmyb32 promoter (FIG. 1) and Atmyb32xs variant promoter sequence with deleted root-specific motifs (FIG. 2) were used for biolistic transformation of wheat (*Triticum aestivum* L. MPB Bobwhite 26). A representative vector is shown in FIG. 24. A schematic of the procedure for biolistic transformation of wheat is outlined in FIG. 27. The transformation procedure includes the following steps:

Step 1 (Donor Plant Production):

*Triticum aestivum* (Bobwhite 26) seed is used for the production of donor plant material. Wheat plants are grown in a nursery mix consisting of composted pine bark, perlite and vermiculite, with five plants per pot to a maximum pot size of 20 cm. Plants are kept under glasshouse conditions at approximately 22-24° C. for 12-16 weeks (FIG. 28A). Once the first spike emerges from the flag leaf, plants are tagged and embryos collected from the tallest heads 12-15 days post anthesis.

Step 2 (Day 1)

Spikes at the desired stage of development are harvested (FIG. 28B). Caryopsis are removed from the spikes and surface sterilised for 20 minutes in a 0.8% (v/v) NaOCl solution and rinsed at least four times in sterile distilled water.

Embryos up to 10 mm in length are aseptically excised from each caryopsis (removing the axis) using a dissecting microscope and cultured axial side down on an osmotic medium (E3maltose) consisting of 2× Murashige and Skoog (1962) macronutrients, 1× micronutrients and organic vitamins, 40 mg/L thiamine, 150 mg/L L-asparagine, supplemented with 15% (w/v) maltose, 0.8% (w/v) Sigma-agar and 2.5 mg/L 2,4-D (FIG. 28C & D). Embryos are cultured on 60 mm×15 mm clear polypropylene petrie dishes with 15 mL of media. Culture plates are incubated at 24° C. in the dark for 4 hours prior to bombardment. Embryos are bombarded using a BioRad PDS1000 gene gun at 900 psi and at 6 cm with 1 μg of vector plasmid DNA precipitated onto 0.6 μm gold particles. Following bombardment, embryos are incubated overnight in the dark on the osmotic media.

Step 3 (Day 2):

Embryos are transferred to a callus induction medium (E3calli) consisting of 2× Murashige and Skoog (1962) macronutrients and 1× micronutrients and organic vitamins, 40 mg/L thiamine, 150 mg/L L-asparagine, supplemented with 6% (w/v) sucrose, 0.8% (w/v) Sigma-agar and 2.5 mg/L 2,4-D. Embryos are cultured for two weeks at 24° C. in the dark.

Step 4 (Day 16):

After 2 weeks of culture on E3calli, embryos have produced embryogenic callus and are subcultured onto a selection medium (E3Select) consisting of 2× Murashige and Skoog (1962) macronutrients and 1× micronutrients and organic vitamins, 40 mg/L thiamine, 150 mg/L L-asparagine, supplemented with 2% (w/v) sucrose, 0.8% (w/v) Sigma-agar, 5 mg/L of D,L phosphinothricin (PPT) and no plant growth regulators (FIG. 28E-G). Cultures are incubated for further 14 days on E3Select at 24° C. in the light and a 12-hour photoperiod.

Step 5 (Day 30):

After 14 days culture on E3Select, embryogenic callus is sub-cultured onto fresh E3Select for a further 14 days (FIG. 28E-G).

Step 6 (Day 44):

After about 4 weeks on E3Select, developing plantlets are excised from the embryonic callus mass and grown for a further three weeks in 65 mm×80 mm or 65 mm×150 mm polycarbonate tissue culture vessels containing rooting induction medium (RM). Root induction medium consists of 1× Murashige and Skoog (1962) macronutrients, micronutrients and organic vitamins, 40 mg/L thiamine, 150 mg/L L-aspar-agine, supplemented with 2% (w/v) sucrose, 0.8% (w/v) Sigma-agar, and 5 mg/L of PPT (FIG. 28H). Remaining embryogenic callus is sub-cultured onto E3Select for another 14 days.

Step 7 (Day 65+):

Regenerated plantlets surviving greater than 3 weeks on RM with healthy root formation are potted into a nursery mix consisting of peat and sand (1:1) and kept at 22-24° C. with elevated humidity under a nursery humidity chamber system (FIG. 28). After two weeks, plants are removed from the humidity chamber and hand watered and liquid fed Aquasol™ weekly until maturity. The $T_0$ plants are sampled for genomic DNA and molecular analysis. $T_1$ seed is collected and planted for high-throughput Q-PCR analysis (FIG. 28J).

Example 10

Agronomic Performance of Transgenic White Clover Plants

The agronomic performance of atmyb32::ipt transgenic white clover (*Trifolium repens*) plants, relative to that of non-transgenic control white clover plants, was evaluated under environmentally controlled growth chamber conditions and in contained field trials (FIG. 29).

Transgenic white clover plants expressing chimeric Atmyb32::ipt genes assessed under controlled growth chamber conditions revealed a significantly enhanced biomass accumulation and reductions in manifestations of senescence, when compared with non-transgenic control white clover plants (FIG. 30). The transgenic white clover plants expressing chimeric Atmyb32::ipt genes showed enhanced total leaf area, increased cumulative leaf area, higher leaf growth dynamics (i.e. number of leaves over time), higher stolon length and increased % flowering plants as well as reduced stolon senescence and death compared with non-transgenic control white clover plants (FIG. 30A-C).

The seed yield performance of 3 independent atmyb32::ipt expressing transgenic white clover plants (i.e. LXR 12, LXR 18 and LXR 11) was also comparatively assessed with non-transgenic control plants (i.e. wild type, WT) under contained field conditions. Two independent atmyb32::ipt expressing transgenic white clover plants (i.e. LXR 12 and LXR 18) with indistinguishable flowering intensity (i.e. number of ripe flowers per m²) to the non-transgenic control plant (i.e. WT) were selected for field evaluation (FIG. 31).

While the seed weight (i.e. weight of thousand seeds) of transgenic white clover plants expressing chimeric Atmyb32::ipt genes (i.e. LXR 12, LXR 18 and LXR 11) was indistinguishable from non-transgenic control white clover plants (i.e. WT) (FIG. 32), the total seed yield expressed on the basis of per flower (FIG. 33), and per area sown (FIG. 34) was doubled in transgenic white clover plants expressing chimeric Atmyb32::ipt genes (i.e. LXR 12 and LXR 18) when compared with non-transgenic control white clover plants of equivalent flowering intensity (i.e. WT).

Example 11

*Agrobacterium*-mediated transformation of alfalfa (*Medicago sativa*)

The binary vector pBMVkATMYB32xs::ipt-nos (FIG. 18) containing chimeric ipt genes under control of Atmyb32xs variant promoter sequence with deleted root-specific motifs (FIG. 2) was used for *Agrobacterium*-mediated transformation of *Medicago sativa* petiole explants from highly-regenerable alfalfa (*M. sativa*) clones C2-3, C2-4 and 19-17 (FIG. 35).

Following co-cultivation with *Agrobacterium tumefaciens* strain LBA 4404 harbouring the binary vector pBMVkATMYB32xs::ipt-nos, the alfalfa explants were washed with medium containing cefotaxime and used for induction of embryogenic callus under selective medium containing 25 mg/l kanamycin. Transgenic embryogenic alfalfa calli were recovered and allowed to regenerate transgenic alfalfa shoots, which were transferred on rooting medium leading to the recovery of transgenic alfalfa plants expressing chimeric ipt genes under control of Atmyb32xs variant promoter (FIG. 35).

It will be understood that the invention disclosed and defined in this specification extends to all alternative combinations of two or more of the individual features mentioned or evident from the text or drawings. All of these different combinations constitute various alternative aspects of the invention.

Example 12

Production of Transgenic Canola Plants

Transgenic canola plants (*Brassica napus*) were produced by *Agrobacterium*-mediated transformation using binary vectors (FIGS. 20 and 22) carrying the chimeric atmyb32::ipt gene. The genetic modification has been characterised for the presence of the candidate gene (IPT) or the selectable marker (hph) using PCR at the $T_1$ generation (FIG. 36).

FIG. 36 illustrates PCR analysis of transgenic canola plants. Genomic DNA was isolated from different transgenic canola plants of $T_1$ LXR04 lines and subjected to PCR using primers specific for the selectable marker (hph gene) or the candidate gene of interest (IPT). In FIG. 36A hph specific primers were used to amplify a product from genomic DNA and were visualised on an agarose gel. FIG. 36B demonstrates the use of IPT specific primers to amplify genomic DNA using a fluorescent PCR method. The primers are specific for the target sequence which results in detectable fluorescence that is inversely proportional to the amount of accumulated PCR product.

Example 13

IPT Gene Expression in Transgenic Canola Plants

The expression of the atmyb32::ipt transgene in transgenic canola was assessed using a fluorescent RT-PCR method specific for the target sequence (FIG. 37). The IPT mRNA was detected in tissues and relative expression levels were compared among lines and with null controls. Null controls are progeny lines that have undergone the transformation process but do not contain target sequences after crossing.

Example 14

Delayed Detached Leaf Senescence in Transgenic Canola Plants

Experiments were performed to assess detached leaf senescence of atmyb32::ipt transgenic plants. FIGS. 38 to 41 indicate detached senescence assay data associated with expression of the candidate gene in canola. Assays for detached cotyledons and leaves were conducted to induce aging and assess the senescence phenotype of transformed canola as compared to wild-type controls. At day 7 and 14 of the detached senescence assays the progress of senescence was qualitatively scored for each tissue sample as either 0—no possible signs of senescence; 1—first visible signs of senescence with a paling of the green colour: 2—further progression of senescence with yellowing in colour becoming noticeable; 3—the tissue was mostly yellow in colour, however a pale green colour remained evident; 4—progression to completely yellow in colour; 5—yellow in colour with some bleaching and patches of necrosis (FIGS. 39 and 41).

Example 15

Production of Transgenic Wheat Plants

Genetic transformation of wheat was based on biolistic transformation of zygotic embryos from *Triticum aestivum* L Bobwhite 26 wheat line as outlined in FIGS. 27 and 28.

The chimeric atmyb32::ipt gene was inserted into the wheat genome by particle bombardment using whole plasmids so vector backbone sequences may also be incorporated into the genome (FIG. 24).

The transformation vector has been fully sequenced (FIG. 25). The genetic modification has been characterised for the presence of the candidate gene by Southern analysis at the $T_1$ generation (FIG. 42).

FIG. 42 illustrates Southern hybridisation analysis of transgenic wheat plants. Genomic DNA was isolated from different $T_1$ lines of transgenic wheat plants and digested with a restriction enzyme to determine candidate gene copy number. The control is non-transformed wild-type *Triticum aestivum* 'Bobwhite 26'. Digests were electrophoresed, transferred to nylon membrane and probed with a full-length DIG labelled IPT gene, as a probe. A range of copy numbers was observed.

Example 16

IPT Gene Expression in Transgenic Wheat Plants

RNA was extracted from young leaf tissue of glasshouse grown transgenic $T_1$ wheat plants containing the IPT gene driven by the AtMYB32 promoter and first strand cDNA prepared.

Quantitative expression of the transgene was determined using a probe based qRT-PCR method for the target sequence. Representative examples of high, medium and low expressing lines for each of the constructs are presented in FIG. 43. A primer/probe set designed to the endogenous sucrose synthase gene was also used as a control. All amplification plots of the control gene began with in one cycle of each other indicating differences in the level of detection of the GMOs is due to variation in expression.

Both the PCR primers and probe are specific for the target sequence which results in detectable fluorescence that is proportional to the amount of accumulated PCR product. Serially diluted plasmid DNA containing the target sequence being detected was employed to create a standard curve for quantification.

Example 17

Plant Morphology in Transgenic Wheat Plants

Differences in growth characteristics were observed in the glasshouse within and among transgenic wheat lines. The phenotypes predominantly observed among $T_1$ wheat plants included stunted plant height, tillering intensity, leaf number, as well as vegetative biomass (FIG. 44).

Example 18

Delayed Detached Leaf Senescence in Transgenic Wheat Plants

A detached leaf assay was used to assess induced aging and the senescence phenotype of transformed wheat leaves as compared to null controls (FIG. 45). Null controls are progeny lines that have undergone the transformation process but do not contain target sequences after crossing.

Example 19

Analysis of Transgenic Canola Plants

Transgenic T2 canola plants expressing the chimeric atmyb32::ipt transgene showed a higher number of stems, inflorescences, flowers and mature siliques than control plants. FIGS. 46 and 47 show the numbers of stems, inflorescences, flowers and siliques 150 and 225 days after planting for atmyb32::ipt transgenic canola (i.e. LXR lines) compared to the wild type non-transgenic control (WT).

Molecular analysis of T2 transgenic canola lines (i.e. LXR 7.1 lines) expressing the chimeric atmyb32::ipttransgene showed a single copy of the transgene in all analysed lines (FIG. 48).

Analysis of the expression level of the chimeric atmyb32::ipt transgene in T2 transgenic canola lines revealing a range of expression levels in the 6.6-, 7.1- and 8.9-derived lines. LXR 6.6-derived lines showed highest level of expression of the atmyb32::ipt transgene. No expression observed in the wild-type, negative control line (FIG. 49).

T2 transgenic canola lines expressing the chimeric atmyb32::ipt transgene showed up to a 5 fold increase in flower number and up to a 6 fold increase in seed yield when compared to wild-type, negative, non-transgenic controls (FIG. 50).

Analysis of the seed weight (seed weight/100 seeds) showed up to a 30% increase in seed weight in the transgenic canola plants expressing the chimeric atmyb32::ipt transgene relative to the wild-type, negative, non-transgenic control. (FIG. 51).

It will also be understood that the term "comprises" (or its grammatical variants) as used in this specification is equivalent to the term "includes" and should not be taken as excluding the presence of other elements or features.

Documents cited in this specification are for reference purposes only and their inclusion is not an acknowledgement that they form part of the common general knowledge in the relevant art.

Finally, it is to be understood that various alterations, modifications and/or additions may be made without departing from the spirit of the present invention as outlined herein.

The invention claimed is:

1. A method of manipulating senescence in a plant or for enhancing plant biomass, said method comprising introducing into said plant a genetic construct comprising a modified myb gene promoter, said modified myb gene promoter comprising a nucleotide sequence selected from the group consisting of:

SEQ ID NO: 1 modified such that one or more root specific motifs in the sequence are deleted or inactivated, and wherein each of said root specific motifs comprises the consensus sequence ATATT or AATAT, and SEQ ID NO: 1 modified such that one or more pollen specific motifs in the sequence are deleted or inactivated, and wherein each of said pollen specific motifs comprises the consensus sequence TTCT or AGAA;

said modified myb gene promoter being operatively linked to a cytokinin biosynthesis gene.

2. The method according to claim 1, wherein said modified myb gene promoter comprises the nucleotide sequence of SEQ ID NO: 1 modified such that between one and ten root specific motifs in the sequence are deleted or inactivated.

3. The method according to claim 1, wherein said modified myb gene promoter comprises the nucleotide sequence of SEQ ID NO: 1 modified such that between one and thirty pollen specific motifs are deleted or inactivated.

4. The method according to claim 1, wherein said myb gene promoter is from *Arabidopsis*.

5. The method according to claim 1, wherein said cytokinin biosynthesis gene is selected from the group consisting of an isopentenyl transferase (ipt) gene and a sho gene.

6. The method according to claim 5, wherein said cytokinin biosynthesis gene is from a genus selected from the group consisting of *Agrobacterium, Lotus* and *Petunia*.

7. The method according to claim 5, wherein said cytokinin biosynthesis gene comprises a nucleotide sequence selected from the group consisting of SEQ ID NOS: 5, 7 and 9, and nucleotide sequences encoding the polypeptides having a sequence of SEQ ID NOS: 6, 8 and 10.

8. The method according to claim 1, wherein said genetic construct is introduced into said plant by *Agrobacterium*-mediated or biolistic transformation of plant cells.

9. The method according to claim 8, wherein plant cells incorporating the genetic construct are selected and then cultured to regenerate transformed plants.

10. A. vector comprising a modified myb gene promoter, said myb gene promoter comprising a nucleotide sequence selected from the group consisting of:
   SEQ ID NO: 1 modified such that one or more root specific motifs in the sequence are deleted or inactivated, and wherein each of said root specific motifs comprises the consensus sequence ATATT or AATAT, and
   SEQ ID NO: 1 modified such that one or more pollen specific motifs in the sequence are deleted or inactivated, and wherein each of said pollen specific motifs comprises the consensus sequence TTCT or AGAA;
   said modified myb gene promoter being operatively linked to a cytokinin biosynthesis gene.

11. The vector according to claim 10, further comprising a terminator; said promoter, gene and terminator being operatively linked.

12. The vector according to claim 10, wherein said modified myb gene promoter comprises the nucleotide sequence of SEQ ID NO: 1 modified such that between one and ten root specific motifs in the sequence are deleted or inactivated.

13. The vector according to claim 10, wherein said modified myb gene promoter comprises the nucleotide sequence of SEQ ID NO: 1 modified such that between one and thirty pollen specific motifs are deleted or inactivated.

14. The vector according to claim 10, wherein said modified myb gene promoter is from *Arabidopsis*.

15. The vector according to claim 10, wherein said cytokinin biosynthesis gene is selected from the group consisting of an isopentenyl transferase (ipt) gene and a sho gene.

16. The vector according to claim 15, wherein said cytokinin biosynthesis gene is from a genus selected from the group consisting of *Agrobacterium, Lotus* and *Petunia*.

17. The vector according to claim 15, wherein said cytokinin biosynthesis gene comprises a nucleotide sequence selected from the group consisting of SEQ ID NOS: 5, 7 and 9, and nucleotide sequences encoding polypeptides having a sequence of SEQ ID NOS: 6, 8 and 10.

18. A transgenic plant cell, plant, plant seed or other plant part, with modified senescence characteristics, said plant cell, plant, plant seed or other plant part comprising a genetic construct comprising a modified myb gene promoter, said modified myb gene promoter comprising a nucleotide sequence selected from the group consisting of:
   SEQ ID NO: 1 modified such that one or more root specific motifs in the sequence are deleted or inactivated, and wherein each of said root specific motifs comprises the consensus sequence ATATT or AATAT, and
   SEQ ID NO: 1 modified such that one or more pollen specific motifs in the sequence are deleted or inactivated, and wherein each of said pollen specific motifs comprises the consensus sequence TTCT or AGAA;
   said modified myb gene promoter being operatively linked to a cytokinin biosynthesis gene.

19. A transgenic plant, plant seed or other plant part derived from the transgenic plant cell according to claim 18.

20. A transgenic plant, plant seed or other plant part derived from the transgenic plant cell, plant, plant seed or other plant part of claim 18.

21. The method according to claim 1, wherein said modified myb gene promoter comprises a nucleotide sequence selected from the group consisting of SEQ ID NOS: 2, 3 and 4.

22. The vector according to claim 10 wherein said modified myb gene promoter comprises a nucleotide sequence selected from the group consisting of SEQ ID NOS: 2, 3 and 4.

23. A transgenic plant cell, plant, plant seed or other plant part, with modified senescence characteristics, said plant cell, plant, plant seed or other plant part being produced by the method according to claim 1.

* * * * *

UNITED STATES PATENT AND TRADEMARK OFFICE
CERTIFICATE OF CORRECTION

PATENT NO. : 8,399,739 B2
APPLICATION NO. : 12/605214
DATED : March 19, 2013
INVENTOR(S) : G. Spangenberg et al.

It is certified that error appears in the above-identified patent and that said Letters Patent is hereby corrected as shown below:

Delete title page and substitute the attached title page therefor.

In the Claims

| COLUMN | LINE | ERROR |
|---|---|---|
| 76 (Claim 21, | 30 line 1) | Claim has been canceled, delete claim in its entirety. |
| 76 (Claim 22, | 34 line 1) | Claim has been canceled, delete claim in its entirety. |
| 76 (Claim 23, | 37 line 1) | Delete "23" and insert --21-- |

Signed and Sealed this
Eighteenth Day of February, 2014

Michelle K. Lee
*Deputy Director of the United States Patent and Trademark Office*

(12) United States Patent
Spangenberg et al.

(10) Patent No.: US 8,399,739 B2
(45) Date of Patent: Mar. 19, 2013

(54) MANIPULATION OF PLANT SENESCENCE USING MODIFIED PROMOTERS

(75) Inventors: German Spangenberg, Bundoora (AU); Carl McDonald Ramage, Craigieburn (AU); Melissa Ann Palviainen, Eden Park (AU); Roger W. Parish, Warrandyte (AU); Joshua Heazlewood, Duncraig (AU)

(73) Assignees: Agriculture Victoria Services Pty, Attwood (AU); La Trobe University, Bundoora (AU)

( * ) Notice: Subject to any disclaimer, the term of this patent is extended or adjusted under 35 U.S.C. 154(b) by 445 days.

(21) Appl. No.: 12/605,214

(22) Filed: Oct. 23, 2009

(65) Prior Publication Data

US 2010/0192259 A1 Jul. 29, 2010

Related U.S. Application Data

(63) Continuation-in-part of application No. 11/789,526, filed on Apr. 24, 2007, now abandoned, which is a continuation-in-part of application No. 10/363,723, filed as application No. PCT/AU01/01092 on Aug. 30, 2001, now Pat. No. 7,227,055, application No. 12/605,214, which is a continuation-in-part of application No. PCT/AU2008/000566, filed on Apr. 21, 2008.

(30) Foreign Application Priority Data

Sep. 6, 2000 (AU) .................................. PQ9946

(51) Int. Cl.
  *A01H 1/00* (2006.01)
  *A01H 5/00* (2006.01)
  *A01H 5/10* (2006.01)
  *C12N 15/09* (2006.01)
  *C12N 15/82* (2006.01)

(52) U.S. Cl. ........ 800/290; 800/278; 800/298; 800/295; 435/320.1; 435/419; 435/468

(58) Field of Classification Search .................... None
See application file for complete search history.

(56) References Cited

FOREIGN PATENT DOCUMENTS

| | | |
|---|---|---|
| WO | WO 96/29858 A1 | 10/1996 |
| WO | WO 00/70061 A2 | 11/2000 |
| WO | WO 02/20772 A1 | 3/2002 |

OTHER PUBLICATIONS

Agriculture Victoria Services Pty Ltd et al., "International Search Report and Written Opinion of the International Searching Authority," issued in related International Patent Application No. PCT/AU2008/000556 by the Australian Patent Office on Jun. 2008, citing the five references disclosed in this Information Disclosure Statement.

Gan S. et al., "Developmental Targeting of Gene Expression by the Use of a Senescence-specific Promoter," Inducible Gene Expression in Plants, Reynolds P.H.S. (ED). 1999, CABI Publishing, Wallingford, U.K., pp. 169-186.

Gans S. et al., "Inhibition of Leaf Senescence by Autoregulated Production of Cytokinin," Science, vol. 270, 1995, pp. 1986-1988.

Smart C.M. et al., "Delayed Leaf Senescence in Tobacco Plants Transformed With tmr, a Gene for Cytokinin Production in Agrobacterium," The Plant Cell, vol. 3, No. 7, 1991, pp. 647-656.

Zhang J. et al., "Development of Flooding-tolerant *Arabidopsis thaliana* by Autoregulated Cytokinin Production," Molecular Breeding, vol. 6, No. 2, 2000, pp. 135-144.

Kranz H.D. et al., "Towards functional characterisation of the members of the R2R3-MYB gene family from *Arabidopsis thaliana*," The Plant Journal (1998) vol. 16, No. 2, pp. 236-276, Blackwell Science Ltd., Oxford, GB.

Song Feng Li, et al., "A novel myb-related gene from *Arabidopsis thaliana*," Febs Letters, Elsevier, Amsterdam, NL, vol. 379, Jan. 1, 1996, pp. 117-121.

Yi Han Lin et al., "Organ-specific, developmentally-regulated and abiotic stress-induced activities of four *Arabidopsis thaliana* promoters in transgenic white clover (*Trifolium repens* L.)," Plant Science, Elsevier Ireland Ltd., J. Plant Sci. 2003-08-01 1, vol. 165, No. 6, Dec. 1, 2003, pp. 1437-1444.

Sidorenko L.V. et al., "Complex structure of a maize Myb gene promoter: functional analysis in transgenic plants," The Plant Journal, vol. 22, No. 6, Jun. 2000, pp. 471-482.

Agriculture Victoria Services Pty Ltd. et al., Supplementary European Search Report issued on corresponding European Patent Application No. 08733383.7 on Jun. 1, 2010, 9 pages.

Extended European Search Report mailed Mar. 29, 2012, issued in corresponding European Patent Application No. 12153159.4, filed Apr. 21, 2008, 8 pages.

*Primary Examiner* — Medina A Ibrahim
(74) *Attorney, Agent, or Firm* — Christensen O'Connor Johnson Kindness PLLC

(57) ABSTRACT

The present invention relates to methods of manipulating senescence in plants. The invention also relates to vectors useful in such methods, transformed plants with modified senescence characteristics and plant cells, seeds and other parts of such plants.

21 Claims, 65 Drawing Sheets

SEQUENCE LISTING

```
<160> NUMBER OF SEQ ID NOS: 15

<210> SEQ ID NO 1
<211> LENGTH: 941
<212> TYPE: DNA
<213> ORGANISM: Arabidopsis thaliana

<400> SEQUENCE: 1
gtttgtgtct tctagattaa tcctccaaac ttttgattaa ccaaaaaaat tatcaaacta      60
acatgttctc cttttttctt tagaaattct aacgaattta tctttatact gatttgaata     120
tacttaattt ggtcatttgg atgcccttta caacctcctt accaaactca ctatggcaaa     180
tatatactat tttccattgt aacataaatg tccataattt gaattaaatt cgttgcagta     240
cgaaaccatc caactttgtc caaaaacaaa atccttataa ctatttactt taatgtaaat     300
atatcctcta cttttgtttt tacaaccctta gctcaaacaa atttattatt tgcgataaaa     360
aatcatatcg aacaaactcg atgatttttt ttttcttacg ttattaatga aactaaaata     420
tagaaaaaaa caagatgaac caaatttctca cctatctaac tacttaaata taatatgatt     480
aaatttggta aagtttgaaa agtttctttta gaaatgtgaa atattgatca cagtttctat     540
tgctaaaatc accaacaaaa cgcatgtcgc cattcataat tatggtttca cacctacaac     600
taggctaata agtaaataag tagacaacta gactcaggtt tgaaaaaacc ataaaagcca     660
tatagcgttt tctcattgaa actgcgaaca cgatcgtgtg aatgttgcag tttctagttt     720
tgatacaaac aaacaaaaac acaatttaat cttagattaa aaagaaaaaa gagaacggag     780
cccactagcc actccttcaa acgtgtctta ccaactctct tctagaaaca aattaggctt     840 cccttcctc ttccaacctc tctctctctc tctctctctt tttctcaaac catctctcca     900
taaagcccta atttcttcat cacaagaatc agaagaagaa a                         941
```

<210> SEQ ID NO 2
<211> LENGTH: 588
<212> TYPE: DNA
<213> ORGANISM: Arabidopsis thaliana

<400> SEQUENCE: 2
gtttgtgtct tctagattaa tcctccaaac ttttgattaa ccaaaaaaat tatcaaacta     60
acatgttctc cttttttctt tagaaattct aacgaattta tctttatact gatttgaata    120
tacttaattt ggtcatttgg atgccctttta caacctcctt accaaactca ttgatcacag    180
tttctattgc taaaatcacc aacaaaacgc atgtcgccat tcataattat ggtttcacac    240
ctacaactag gctaataagt aaataagtag acaactagac tcaggtttga aaaaaccata    300
aaagccatat agcgttttct cattgaaact gcgaacacga tcgtgtgaat gttgcagttt    360
ctagttttga tacaaacaaa caaaaacaca atttaatctt agattaaaaa gaaaaaagag    420
aacggagccc actagccact ccttcaaacg tgtcttacca actctcttct agaaacaaat    480
taggcttcac cttcctcttc caacctctct ctctctctct ctctcttttt ctcaaaccat    540
ctctccataa agccctaatt tcttcatcac aagaatcaga agaagaaa              588

<210> SEQ ID NO 3
<211> LENGTH: 468
<212> TYPE: DNA
<213> ORGANISM: Arabidopsis thaliana

<400> SEQUENCE: 3
tacttaattt ggtcatttgg atgccctttta caacctcctt accaaactca ttgatcacag     60
tttctattgc taaaatcacc aacaaaacgc atgtcgccat tcataattat ggtttcacac    120
ctacaactag gctaataagt aaataagtag acaactagac tcaggtttga aaaaaccata    180
aaagccatat agcgttttct cattgaaact gcgaacacga tcgtgtgaat gttgcagttt    240
ctagttttga tacaaacaaa caaaaacaca atttaatctt agattaaaaa gaaaaaagag    300
aacggagccc actagccact ccttcaaacg tgtcttacca actctcttct agaaacaaat    360
taggcttcac cttcctcttc caacctctct ctctctctct ctctcttttt ctcaaaccat    420
ctctccataa agccctaatt tcttcatcac aagaatcaga agaagaaa              468

<210> SEQ ID NO 4
<211> LENGTH: 419
<212> TYPE: DNA
<213> ORGANISM: Arabidopsis thaliana

<400> SEQUENCE: 4
attgatcaca gtttctattg ctaaaatcac caacaaaacg catgtcgcca ttcataatta     60
tggtttcaca cctacaacta ggctaataag taaataagta gacaactaga ctcaggtttg    120
aaaaaaccat aaaagccata tagcgttttc tcattgaaac tgcgaacacg atcgtgtgaa    180
tgttgcagtt tctagttttg atacaaacaa acaaaaacac aatttaatct tagattaaaa    240
agaaaaaaga gaacggagcc cactagccac tccttcaaac gtgtcttacc aactctcttc    300
tagaaacaaa ttaggcttca ccttcctctt ccaacctctc tctctctctc tctctctttt    360
tctcaaacca tctctccata aagccctaat tcttcatca aagaatcag aagaagaaa      419

<210> SEQ ID NO 5
<211> LENGTH: 723
<212> TYPE: DNA
<213> ORGANISM: Agrobacterium tumefaciens -continued

<400> SEQUENCE: 5

```
atggacctgc atctaatttt cggtccaact tgcacaggaa agacgacgac cgcgatagct    60
cttgcccagc agacagggct tccagtcctt tcgcttgatc gggtccaatg ctgtcctcaa   120
ctatcaaccg gaagcggacg accaacagtg aagaactgaa aggaacgac  gcgtctctac   180
cttgatgatc ggcctctggt ggagggtatc atcgcagcca agcaagctca tcataggctg   240
atcgaggagg tgtataatca tgaggccaac ggcgggctta ttcttgaggg aggatccacc   300
tcgttgctca actgcatggc gcgaaacagc tattggagtg cagattttcg ttggcatatt   360
attcgccaca agttacccga ccaagagacc ttcatgaaag cggccaaggc cagagttaag   420
cagatgttgc accccgctgc aggccattct attattcaag agttggttta tctttggaat   480
gaacctcggc tgaggcccat tctgaaagag atcgatggat atcgatatgc catgttgttt   540
gctagccaga accagatcac ggcagatatg ctattgcagc ttgacgcaaa tatggaaggt   600
aagttgatta atgggatcgc tcaggagtat ttcatccatg cgcgccaaca ggaacagaaa   660
ttcccccaag ttaacgcagc cgctttcgac ggattcgaag gtcatccgtt cggaatgtat   720
tag                                                                 723
```

<210> SEQ ID NO 6
<211> LENGTH: 240
<212> TYPE: PRT
<213> ORGANISM: Agrobacterium tumefaciens

<400> SEQUENCE: 6

```
Met Asp Leu His Leu Ile Phe Gly Pro Thr Cys Thr Gly Lys Thr Thr
  1               5                  10                  15

Thr Ala Ile Ala Leu Ala Gln Gln Thr Gly Leu Pro Val Leu Ser Leu
             20                  25                  30

Asp Arg Val Gln Cys Cys Pro Gln Leu Ser Thr Gly Ser Gly Arg Pro
         35                  40                  45

Thr Val Glu Glu Leu Lys Gly Thr Thr Arg Leu Tyr Leu Asp Asp Arg
     50                  55                  60

Pro Leu Val Glu Gly Ile Ile Ala Ala Lys Gln Ala His His Arg Leu
 65                  70                  75                  80

Ile Glu Glu Val Tyr Asn His Glu Ala Asn Gly Gly Leu Ile Leu Glu
                 85                  90                  95

Gly Gly Ser Thr Ser Leu Leu Asn Cys Met Ala Arg Asn Ser Tyr Trp
            100                 105                 110

Ser Ala Asp Phe Arg Trp His Ile Ile Arg His Lys Leu Pro Asp Gln
        115                 120                 125

Glu Thr Phe Met Lys Ala Ala Lys Ala Arg Val Lys Gln Met Leu His
    130                 135                 140

Pro Ala Ala Gly His Ser Ile Ile Gln Glu Leu Val Tyr Leu Trp Asn
145                 150                 155                 160

Glu Pro Arg Leu Arg Pro Ile Leu Lys Glu Ile Asp Gly Tyr Arg Tyr
                165                 170                 175

Ala Met Leu Phe Ala Ser Gln Asn Gln Ile Thr Ala Asp Met Leu Leu
            180                 185                 190

Gln Leu Asp Ala Asn Met Glu Gly Lys Leu Ile Asn Gly Ile Ala Gln
        195                 200                 205

Glu Tyr Phe Ile His Ala Arg Gln Gln Glu Gln Lys Phe Pro Gln Val
    210                 215                 220

Asn Ala Ala Ala Phe Asp Gly Phe Glu Gly His Pro Phe Gly Met Tyr
225                 230                 235                 240
```

<210> SEQ ID NO 7
<211> LENGTH: 975
<212> TYPE: DNA
<213> ORGANISM: Lotus japonicus

<400> SEQUENCE: 7

```
atgtccatct caatgctaat gtgcagacta agacaaccct taataaacgt tccctgcagt      60
ggcaaaaaac tgagcatgag gcagattcaa aaggagaagg tagtgttggt gatgggagct     120
acagggacag gaaagtcaaa gctctccatt gacctcgcca cctgtttccc ctcagaaatc     180
atcaactccg acaagattca aatctacgac ggcctcgaca tcgtcaccaa caaaatctcc     240
aaggaagaac aacgtggaat ccccaccac ctcctcggaa ctcaaaaccc taacacagac      300
ttcaccgccg gcgatttcag tgactgttcc accgccgcca ttgacgcaat cacaagccgc     360
gaccaccttc cgatcatcgc cggaggttcg aactcctacc tggaggcgtt aatcgacgac     420
gacgactaca aattccgatc gaggtacgac ttctgctgcc tctgggtcga cgtggcaatg     480
ccggtgctgg actcatacgt ggcggcgcgt gtggatcaga tgctccggag cggaatggtg     540
gaggagctga accgtttttt caacgcgaac ggcgactact cgagaggaat cagaagagcg     600
attggggttc ctgaattcga cgagtatttc cggcgggaag ggttcgccga tgaggaaacg     660
aggaaattgt tactggagcg agcggtgagg gagatgaagg tgaacacgtg caagctcgcg     720
aggaggcaat ggggaagat tcagaggctg aggaatgtga agaggtggga gattcaccgt      780
gttgatgcga cgccggtgtt ttggaagcgt ggggaggagg ctgatgaggc gtggcggaag     840
gtggtggcag agcctagtgc tatgatcgta gcgcagtttc tgtataaggc aaagagtgat     900
gtgaatgttg tttctggcgg tttcagagtg ccggcgggtt caacggagag tgttatggcg     960
gcggcgacgt gttag                                                      975
```

<210> SEQ ID NO 8
<211> LENGTH: 324
<212> TYPE: PRT
<213> ORGANISM: Lotus japonicus

<400> SEQUENCE: 8

```
Met Ser Ile Ser Met Leu Met Cys Arg Leu Arg Gln Pro Leu Ile Asn
1               5                   10                  15

Val Pro Cys Ser Gly Lys Lys Leu Ser Met Arg Gln Ile Gln Lys Glu
            20                  25                  30

Lys Val Val Leu Val Met Gly Ala Thr Gly Thr Gly Lys Ser Lys Leu
        35                  40                  45

Ser Ile Asp Leu Ala Thr Cys Phe Pro Ser Glu Ile Ile Asn Ser Asp
    50                  55                  60

Lys Ile Gln Ile Tyr Asp Gly Leu Asp Ile Val Thr Asn Lys Ile Ser
65                  70                  75                  80

Lys Glu Glu Gln Arg Gly Ile Pro His His Leu Leu Gly Thr Gln Asn
                85                  90                  95

Pro Asn Thr Asp Phe Thr Ala Gly Asp Phe Ser Asp Cys Ser Thr Ala
            100                 105                 110

Ala Ile Asp Ala Ile Thr Ser Arg Asp His Leu Pro Ile Ile Ala Gly
        115                 120                 125

Gly Ser Asn Ser Tyr Leu Glu Ala Leu Ile Asp Asp Asp Tyr Lys
    130                 135                 140

Phe Arg Ser Arg Tyr Asp Phe Cys Cys Leu Trp Val Asp Val Ala Met
145                 150                 155                 160
```

```
Pro Val Leu Asp Ser Tyr Val Ala Ala Arg Val Asp Gln Met Leu Arg
                165                 170                 175
Ser Gly Met Val Glu Glu Leu Arg Pro Phe Phe Asn Ala Asn Gly Asp
            180                 185                 190
Tyr Ser Arg Gly Ile Arg Arg Ala Ile Gly Val Pro Glu Phe Asp Glu
        195                 200                 205
Tyr Phe Arg Arg Glu Gly Phe Ala Asp Glu Thr Arg Lys Leu Leu
    210                 215                 220
Leu Glu Arg Ala Val Arg Glu Met Lys Val Asn Thr Cys Lys Leu Ala
225                 230                 235                 240
Arg Arg Gln Leu Gly Lys Ile Gln Arg Leu Arg Asn Val Lys Arg Trp
                245                 250                 255
Glu Ile His Arg Val Asp Ala Thr Pro Val Phe Trp Lys Arg Gly Glu
            260                 265                 270
Glu Ala Asp Glu Ala Trp Arg Lys Val Val Ala Glu Pro Ser Ala Met
        275                 280                 285
Ile Val Ala Gln Phe Leu Tyr Lys Ala Lys Ser Asp Val Asn Val Val
    290                 295                 300
Ser Gly Gly Phe Arg Val Pro Ala Gly Ser Thr Glu Ser Val Met Ala
305                 310                 315                 320
Ala Ala Thr Cys

<210> SEQ ID NO 9
<211> LENGTH: 1053
<212> TYPE: DNA
<213> ORGANISM: Petunia x hybrida

<400> SEQUENCE: 9
atgttaattg tagtacatat tattagcatc acacgcatca tattcatcac cttaacccat      60
aatcatctcc atttccttat gtttagatca ttatcataca atcacaagca cctcaaattc     120
cttacaaacc cgaccacacg ggtactccga agaaacatgt cgtcatccac tgtagtaaca     180
atacccggcc ccacacaaaa aaacaaaaac aaaatcatag taataatggg tgcaacaggt     240
tcaggaaaat caaaactctc aatagacctc gtcacacgtc actatccttt tccgaaatc      300
attaactccg acaaaatcca aattaccaaa ggtttaaaca taaccacaaa caaaatcact     360
gtacccgacc gacgtggcgt agttcatcat ttactcggcg agattgaccc cgactttaac     420
tttctccttt ctcatttccg gtcaattgct ggtcaacgca ttaactccat tattaatcgc     480
cataaactcc cattcctcgt tggtgggtcc aactcatata tctacgcttt attaacaaac     540
cggttcgacc cggattttaa ccctgattca aacccggttc attttatatc caacgagtta     600
cgctacaact gttgttttat ttgggtcgat gtattaaacc cggttttgaa tgagtatttg     660
gataaacggg tcgatgagat gatgaactcg ggtatgtatg aagaactgga acagttttt      720
aaagaaaaca ggttttcgga tccgggtttg aaccgggtc gggccaccgg gttgaggaaa     780
gcgataggg taccggaaat ggagaggtat tttaagaaga gctgtacgta tgaggaagca     840
gtgagggaaa taaagaaaa cacgtggcgg ttagcgaaga agcagatgtg gaagatccaa     900
cggttgagag aagcagggtg ggacctacaa agagtagatg ccacggaggc atttgtggag     960
gcgatgagta ataagaagga aaagggaatt atttgggaaa acaagtagt ggaaccaagt    1020
gtcaagattg tgaaccgttt tttgttggac tga                                 1053

<210> SEQ ID NO 10
<211> LENGTH: 350
```

<212> TYPE: PRT
<213> ORGANISM: Petunia x hybrida

<400> SEQUENCE: 10

```
Met Leu Ile Val Val His Ile Ile Ser Ile Thr Arg Ile Ile Phe Ile
1               5                   10                  15

Thr Leu Thr His Asn His Leu His Phe Leu Met Phe Arg Ser Leu Ser
            20                  25                  30

Tyr Asn His Lys His Leu Lys Phe Leu Thr Asn Pro Thr Arg Val
        35                  40                  45

Leu Arg Arg Asn Met Ser Ser Ser Thr Val Val Thr Ile Pro Gly Pro
    50                  55                  60

Thr Gln Lys Asn Lys Asn Lys Ile Ile Val Ile Met Gly Ala Thr Gly
65                  70                  75                  80

Ser Gly Lys Ser Lys Leu Ser Ile Asp Leu Val Thr Arg His Tyr Pro
                85                  90                  95

Phe Ser Glu Ile Ile Asn Ser Asp Lys Ile Gln Ile Thr Lys Gly Leu
            100                 105                 110

Asn Ile Thr Thr Asn Lys Ile Thr Val Pro Asp Arg Arg Gly Val Val
        115                 120                 125

His His Leu Leu Gly Glu Ile Asp Pro Asp Phe Asn Phe Ser Pro Ser
    130                 135                 140

His Phe Arg Ser Ile Ala Gly Gln Arg Ile Asn Ser Ile Asn Arg
145                 150                 155                 160

His Lys Leu Pro Phe Leu Val Gly Gly Ser Asn Ser Tyr Ile Tyr Ala
                165                 170                 175

Leu Leu Thr Asn Arg Phe Asp Pro Asp Phe Asn Pro Asp Ser Asn Pro
            180                 185                 190

Val His Phe Ile Ser Asn Glu Leu Arg Tyr Asn Cys Cys Phe Ile Trp
        195                 200                 205

Val Asp Val Leu Asn Pro Val Leu Asn Glu Tyr Leu Asp Lys Arg Val
    210                 215                 220

Asp Glu Met Met Asn Ser Gly Met Tyr Glu Glu Leu Glu Gln Phe Phe
225                 230                 235                 240

Lys Glu Asn Arg Phe Ser Asp Pro Gly Leu Glu Pro Gly Arg Ala Thr
                245                 250                 255

Gly Leu Arg Lys Ala Ile Gly Val Pro Glu Met Glu Arg Tyr Phe Lys
            260                 265                 270

Lys Ser Cys Thr Tyr Glu Glu Ala Val Arg Glu Ile Lys Glu Asn Thr
        275                 280                 285

Trp Arg Leu Ala Lys Lys Gln Met Trp Lys Ile Gln Arg Leu Arg Glu
    290                 295                 300

Ala Gly Trp Asp Leu Gln Arg Val Asp Ala Thr Glu Ala Phe Val Glu
305                 310                 315                 320

Ala Met Ser Asn Lys Lys Glu Lys Gly Ile Ile Trp Glu Lys Gln Val
                325                 330                 335

Val Glu Pro Ser Val Lys Ile Val Asn Arg Phe Leu Leu Asp
            340                 345                 350
```

<210> SEQ ID NO 11
<211> LENGTH: 10786
<212> TYPE: DNA
<213> ORGANISM: Artificial
<220> FEATURE:
<223> OTHER INFORMATION: Synthetic construct

<400> SEQUENCE: 11

-continued

```
gtcccgtatc acgcagcgcg tgagctaccc aggcactgcc gccgccggca caaccgttct      60
tgaatcagaa cccgagggcg acgctgcccg cgaggtccag gcgctggccg ctgaaattaa     120
atcaaaactc atttgagtta atgaggtaaa gagaaaatga gcaaaagcac aaacacgcta     180
agtgccggcc gtccgagcgc acgcagcagc aaggctgcaa cgttggccag cctggcagac     240
acgccagcca tgaagcgggt caactttcag ttgccggcgg aggatcacac caagctgaag     300
atgtacgcgg tacgccaagg caagaccatt accgagctgc tatctgaata catcgcgcag     360
ctaccagagt aaatgagcaa atgaataaat gagtagatga attttagcgg ctaaaggagg     420
cggcatggaa aatcaagaac aaccaggcac cgacgccgtg gaatgcccca tgtgtggagg     480
aacgggcggt tggccaggcg taagcggctg ggttgtctgc cggccctgca atggcactgg     540
aaccccaag cccgaggaat cggcgtgacg gtcgcaaacc atccggcccg gtacaaatcg      600
gcgcggcgct gggtgatgac ctggtggaga agttgaaggc cgcgcaggcc gcccagcggc     660
aacgcatcga ggcagaagca cgccccggtg aatcgtggca agcggccgct gatcgaatcc     720
gcaaagaatc ccggcaaccg ccggcagccg gtgcgccgtc gattaggaag ccgcccaagg     780
gcgacgagca accagatttt ttcgttccga tgctctatga cgtgggcacc cgcgatagtc     840
gcagcatcat ggacgtggcc gttttccgtc tgtcgaagcg tgaccgacga gctggcgagg     900
tgatccgcta cgagcttcca gacgggcacg tagaggtttc cgcagggccg gccggcatgg     960
ccagtgtgtg ggattacgac ctggtactga tggcggtttc ccatctaacc gaatccatga    1020
accgataccg ggaagggaag ggagacaagc ccggccgcgt gttccgtcca cacgttgcgg    1080
acgtactcaa gttctgccgg cgagccgatg gcggaaagca gaaagacgac ctggtagaaa    1140
cctgcattcg gttaaacacc acgcacgttg ccatgcagcg tacgaagaag gccaagaacg    1200
gccgcctggt gacggtatcc gagggtgaag ccttgattag ccgctacaag atcgtaaaga    1260
gcgaaaccgg gcggccggag tacatcgaga tcgagctagc tgattggatg taccgcgaga    1320
tcacagaagg caagaacccg gacgtgctga cggttcaccc cgattacttt ttgatcgatc    1380
ccggcatcgg ccgttttctc taccgcctgg cacgccgcgc gcaggcaag gcagaagcca     1440
gatggttgtt caagacgatc tacgaacgca gtggcagcgc cggagagttc aagaagttct    1500
gtttcaccgt gcgcaagctg atcgggtcaa atgacctgcc ggagtacgat ttgaaggagg    1560
aggcggggca ggctggcccg atcctagtca tgcgctaccg caacctgatc gagggcgaag    1620
catccgccgg ttcctaatgt acggagcaga tgctagggca aattgcccta gcaggggaaa    1680
aaggtcgaaa aggtctcttt cctgtggata gcacgtacat tgggaaccca aagccgtaca    1740
ttgggaaccg gaacccgtac attgggaacc caaagccgta cattgggaac cggtcacaca    1800
tgtaagtgac tgatataaaa gagaaaaaag gcgattttc cgcctaaaac tctttaaaac     1860
ttattaaaac tcttaaaacc cgcctggcct gtgcataact gtctggccag cgcacagccg    1920
aagagctgca aaaagcgcct acccttcggt cgctgcgctc cctacgcccc gccgcttcgc    1980
gtcggcctat cgcggccgct ggccgctcaa aaatggctgg cctacggcca gcaatctac     2040
cagggcgcgg acaagccgcg ccgtcgccac tcgaccgccg gcgcccacat caaggcaccc    2100
tgcctcgcgc gtttcggtga tgacggtgaa aacctctgac acatgcagct cccggagacg    2160
gtcacagctt gtctgtaagc ggatgccggg agcagacaag cccgtcaggg cgcgtcagcg    2220
ggtgttggcg ggtgtcgggg cgcagccatg acccagtcac gtagcgatag cggagtgtat    2280
actggcttaa ctatgcggca tcagagcaga ttgtactgag agtgcaccat atgcggtgtg    2340
aaataccgca cagatgcgta aggagaaaat accgcatcag gcgctcttcc gcttcctcgc    2400
```

```
tcactgactc gctgcgctcg gtcgttcggc tgcggcgagc ggtatcagct cactcaaagg    2460
cggtaatacg gttatccaca gaatcagggg ataacgcagg aaagaacatg tgagcaaaag    2520
gccagcaaaa ggccaggaac cgtaaaaagg ccgcgttgct ggcgtttttc cataggctcc    2580
gcccccctga cgagcatcac aaaaatcgac gctcaagtca gaggtggcga acccgacag    2640 gactataaag ataccaggcg tttccccctg gaagctccct cgtgcgctct cctgttccga    2700
ccctgccgct taccggatac ctgtccgcct ttctcccttc gggaagcgtg gcgctttctc    2760
atagctcacg ctgtaggtat ctcagttcgg tgtaggtcgt tcgctccaag ctgggctgtg    2820
tgcacgaacc ccccgttcag cccgaccgct gcgccttatc cggtaactat cgtcttgagt    2880
ccaacccggt aagacacgac ttatcgccac tggcagcagc cactggtaac aggattagca    2940
gagcgaggta tgtaggcggt gctacagagt tcttgaagtg gtggcctaac tacggctaca    3000
ctagaaggac agtatttggt atctgcgctc tgctgaagcc agttaccttc ggaaaaagag    3060
ttggtagctc ttgatccggc aaacaaacca ccgctggtag cggtggtttt tttgtttgca    3120
agcagcagat tacgcgcaga aaaaaggat ctcaagaaga tcctttgatc ttttctacgg    3180
ggtctgacgc tcagtggaac gaaaactcac gttaagggat tttggtcatg catgatatat    3240
ctcccaattt gtgtagggct tattatgcac gcttaaaaat aataaaagca gacttgacct    3300
gatagtttgg ctgtgagcaa ttatgtgctt agtgcatcta atcgcttgag ttaacgccgg    3360
cgaagcggcg tcggcttgaa cgaatttcta gctagacatt atttgccgac taccttggtg    3420
atctcgcctt tcacgtagtg acaaattct tccaactgat ctgcgcgcga ggccaagcga    3480
tcttcttctt gtccaagata agcctgtcta gcttcaagta tgacgggctg atactgggcc    3540
ggcaggcgct ccattgccca gtcggcagcg acatccttcg gcgcgatttt gccggttact    3600
gcgctgtacc aaatgcggga caacgtaagc actacatttc gctcatcgcc agcccagtcg    3660
ggcggcgagt tccatagcgt taaggtttca tttagcgcct caaatagatc ctgttcagga    3720
accggatcaa agagttcctc cgccgctgga cctaccaagg caacgctatg ttctcttgct    3780
tttgtcagca agatagccag atcaatgtcg atcgtggctg gctcgaagat acctgcaaga    3840
atgtcattgc gctgccattc tccaaattgc agttcgcgct tagctggata acgccacgga    3900
atgatgtcgt cgtgcacaac aatggtgact tctacagcgc ggagaatctc gctctctcca    3960
ggggaagccg aagtttccaa aaggtcgttg atcaaagctc gccgcgttgt ttcatcaagc    4020
cttacggtca ccgtaaccag caaatcaata tcactgtgtg gcttcaggcc gccatccact    4080
gcggagccgt acaaatgtac ggccagcaac gtcggttcga gatggcgctc gatgacgcca    4140
actacctctg atagttgagt cgatacttcg gcgatcaccg cttcccccat gatgtttaac    4200
tttgttttag ggcgactgcc ctgctgcgta acatcgttgc tgctccataa catcaaacat    4260
cgacccacgg cgtaacgcgc ttgctgcttg gatgcccgag gcatagactg taccccaaaa    4320
aaacatgtca taacaagaag ccatgaaaac cgccactgcg ccgttaccac cgctgcgttc    4380
ggtcaaggtt ctggaccagt tgcgtgacgg cagttacgct acttgcatta cagcttacga    4440
accgaacgag gcttatgtcc actgggttcg tgcccgaatt gatcacaggc agcaacgctc    4500
tgtcatcgtt acaatcaaca tgctaccctc cgcgagatca tccgtgtttc aaacccggca    4560
gcttagttgc cgttcttccg aatagcatcg gtaacatgag caaagtctgc cgccttacaa    4620
cggctctccc gctgacgccg tcccggactg atgggctgcc tgtatcgagt ggtgattttg    4680
tgccgagctg ccggtcgggg agctgttggc tggctggtgg caggatatat tgtggtgtaa    4740
acaaattgac gcttagacaa cttaataaca cattgcggac gtttttaatg tactgaatta    4800
```

```
acgccgaatt gaattcctcg agtacgtagg atccatttaa attctagagg cgcgccgata    4860
tcctctctta aggtagcgag ctcttaatta atagggataa cagggtaatg cggccgcaag    4920
ctaaaacgac ggccagtgaa ttatcaactt tgtatagaaa agttgctctg ccgacagtgg    4980
tcccaaagat ggaccccccac ccacgaggag catcgtggaa aaagaagacg ttccaaccac   5040
gtcttcaaag caagtggatt gatgtgataa catggtggag cacgcactc tcgtctactc     5100 caagaatatc aaagatacag tctcagaaga ccaaagggct attgagactt tcaacaaag     5160 ggtaatatcg ggaaacctcc tcggattcca ttgcccagct atctgtcact tcatcaaaag    5220
gacagtagaa aaggaaggtg gcacctacaa atgccatcat tgcgataaag gaaaggctat    5280
cgttcaagat gcctctgccg acagtggtcc caaagatgga cccccaccca cgaggagcat    5340
cgtggaaaaa gaagacgttc caaccacgtc ttcaaagcaa gtggattgat gtgatatctc    5400
cactgacgta agggatgacg cacaatccca ctatccttcg caagacccct tcctctatata   5460 aggaagttca tttcatttgg agaggacacg ctgcaagttt gtacaaaaaa gcaggctatg    5520
gcaattacct tatccgcaac ttctttacct atttccgccc ggatccgggc aggttctccg    5580
gccgcttggg tggagaggct attcggctat gactgggcac aacagacaat cggctgctct    5640
gatgccgccg tgttccggct gtcagcgcag gggcgcccgg ttcttttttgt caagaccgac   5700 ctgtccggtg ccctgaatga actgcaggac gaggcagcgc ggctatcgtg gctggccacg    5760
acgggcgttc cttgcgcagc tgtgctcgac gttgtcactg aagcgggaag gactggctg     5820 ctattgggcg aagtgccggg gcaggatctc ctgtcatctc accttgctcc tgccgagaaa    5880
gtatccatca tggctgatgc aatgcggcgg ctgcatacgc ttgatccggc tacctgccca    5940
ttcgaccacc aagcgaaaca tcgcatcgag cgagcacgta ctcggatgga agccggtctt    6000
gtcgatcagg atgatctgga cgaagagcat caggggctcg cgccagccga actgttcgcc    6060
aggctcaagg cgcgcatgcc cgacggcgag gatctcgtcg tgacccatgg cgatgcctgc    6120
ttgccgaata tcatggtgga aaatggccgc ttttctggat tcatcgactg tggccggctg    6180
ggtgtggcgg accgctatca ggacatagcg ttggctaccc gtgatattgc tgaagagctt    6240
ggcggcgaat gggctgaccg cttcctcgtg ctttacggta tcgccgctcc cgattcgcag    6300
cgcatcgcct tctatcgcct tcttgacgag ttcttctgaa cccagctttc ttgtacaaag    6360
tggagtccgc aaaaatcacc agtctctctc tacaaatcta tctctctcta tttttctcca    6420
gaataatgtg tgagtagttc ccagataagg gaattagggt tcttataggg tttcgctcat    6480
gtgttgagca tataagaaac ccttagtatg tatttgtatt tgtaaaatac ttctatcaat    6540
aaaatttcta attcctaaaa ccaaaatcca gtgacctcaa ctttattata catagttgat    6600
aattcactgg ccgtgcttat tccatggctg caggtcgacg aattcaccgg ttagggataa    6660
cagggtaatc gctaccttag gaccgttata gttacggcca gtgccattac cctgttatcc    6720
ctaaccggtg acaactttgt atagaaaagt tggtttgtgt cttctagatt aatcctccaa    6780
acttttgatt aaccaaaaaa attatcaaac taacatgttc tccttttttc tttagaaatt    6840
ctaacgaatt tatctttata ctgatttgaa tatacttaat ttggtcattt ggatgccctt    6900
tacaacctcc ttaccaaact cactatggca aatatatact attttccatt gtaacataaa    6960
tgtccataat ttgaattaaa ttcgttgcag tacgaaacca tccaactttg tccaaaaaca    7020
aaatccttat aactatttac tttaatgtaa atatatcctc tacttttgtt tttacaaccc    7080
tagctcaaac aaatttatta tttgcgataa aaaatcatat cgaacaaact cgatgatttt    7140 tttttttctta cgttattaat gaaactaaaa tatagaaaaa aacaagatga accaaatttt    7200
```

```
cacctatcta actacttaaa tataatatga ttaaatttgg taaagtttga aaagtttctt    7260
tagaaatgtg aaatattgat cacagtttct attgctaaaa tcaccaacaa aacgcatgtc    7320
gccattcata attatggttt cacacctaca actaggctaa taagtaaata agtagacaac    7380
tagactcagg tttgaaaaaa ccataaaagc catatagcgt tttctcattg aaactgcgaa    7440
cacgatcgtg tgaatgttgc agtttctagt tttgatacaa acaaacaaaa acacaattta    7500
atcttagatt aaaagaaaa aagagaacgg agcccactag ccactccttc aaacgtgtct     7560
taccaactct cttctagaaa caaattaggc ttcaccttcc tcttccaacc tctctctctc    7620
tctctctctc tttttctcaa accatctctc cataaagccc taatttcttc atcacaagaa    7680
tcagaagaag aaacaagttt gtacaaaaaa gcaggcttac tgcaaaaaac ttatggacct    7740
gcatctaatt ttcggtccaa cttgcacagg aaagacgacg accgcgatag ctcttgccca    7800
gcagacaggg cttccagtcc tttcgcttga tcgggtccaa tgctgtcctc aactatcaac    7860
cggaagcgga cgaccaacag tggaagaact gaaaggaacg acgcgtctct accttgatga    7920
tcggcctctg gtggagggta tcatcgcagc caagcaagct catcataggc tgatcgagga    7980
ggtgtataat catgaggcca acggcgggct tattcttgag ggaggatcca cctcgttgct    8040
caactgcatg gcgcgaaaca gctattggag tgcagatttt cgttggcata ttattcgcca    8100
caagttaccc gaccaagaga ccttcatgaa agcggccaag gccagagtta agcagatgtt    8160
gcaccccgct gcaggccatt ctattattca agagttggtt tatctttgga atgaacctcg    8220
gctgaggccc attctgaaag agatcgatgg atatcgatat gccatgttgt ttgctagcca    8280
gaaccagatc acggcagata tgctattgca gcttgacgca aatatggaag gtaagttgat    8340
taatgggatc gctcaggagt atttcatcca tgcgcgccaa caggaacaga aattccccca    8400
agttaacgca gccgctttcg acggattcga aggtcatccg ttcggaatgt attaggtacc    8460
cagctttctt gtacaaagtg ggatcgttca aacatttggc aataaagttt cttaagattg    8520
aatcctgttg ccggtcttgc gatgattatc atataatttc tgttgaatta cgttaagcat    8580
gtaataatta acatgtaatg catgacgtta tttatgagat gggttttat gattagagtc      8640 ccgcaattat acatttaata cgcgatagaa acaaaatat agcgcgcaaa ctaggataaa       8700
ttatcgcgcg cggtgtcatc tatgttacta gatccaactt tattatacat agttgattcg    8760
tcgacctgca gtcgctacct taggaccgtt atagttatgg caaacagcta ttatgggtat    8820
tatgggtggt tctttatgcg gacactgacg gctttatgcc tgcaggtcgc gagcgatcgc    8880
ggtaccgccc gggcgtcgac aggcctaagc ttagcttgag cttggatcag attgtcgttt    8940
cccgccttca gtttaaacta tcagtgtttg acaggatata ttggcgggta aacctaagag    9000
aaaagagcgt ttattagaat aacggatatt taaagggcg tgaaaaggtt tatccgttcg     9060
tccatttgta tgtgcatgcc aaccacaggg ttccctcgg gatcaaagta ctttgatcca     9120 accctccgc tgctatagtg cagtcggctt ctgacgttca gtgcagccgt cttctgaaaa     9180
cgacatgtcg cacaagtcct aagttacgcg acaggctgcc gccctgccct tttcctggcg    9240
ttttcttgtc gcgtgtttta gtcgcataaa gtagaatact tgcgactaga accggagaca    9300
ttacgccatg aacaagagcg ccgccgctgg cctgctgggc tatgcccgcg tcagcaccga    9360
cgaccaggac ttgaccaacc aacggccga actgcacgcg gccggctgca ccaagctgtt    9420
ttccgagaag atcaccggca ccaggcgcga ccgccggag ctggccagga tgcttgacca    9480
cctacgccct ggcgacgttg tgacagtgac caggctagac cgcctggccc gcagcacccg    9540
cgacctactg gacattgccg agcgcatcca ggaggccggc gcgggcctgc gtagcctggc    9600
```

```
agagccgtgg gccgacacca ccacgccggc cggccgcatg gtgttgaccg tgttcgccgg    9660
cattgccgag ttcgagcgtt ccctaatcat cgaccgcacc cggagcgggc gcgaggccgc    9720
caaggcccga ggcgtgaagt ttggcccccg ccctaccctc accccggcac agatcgcgca    9780
cgcccgcgag ctgatcgacc aggaaggccg caccgtgaaa gaggcggctg cactgcttgg    9840
cgtgcatcgc tcgaccctgt accgcgcact tgagcgcagc gaggaagtga cgcccaccga    9900
ggccaggcgg cgcggtgcct tccgtgagga cgcattgacc gaggccgacg ccctggcggc    9960
cgccgagaat gaacgccaag aggaacaagc atgaaaccgc accaggacgg ccaggacgaa   10020 ccgttttttca ttaccgaaga gatcgaggcg gagatgatcg cggccgggta cgtgttcgag   10080
ccgcccgcgc acgtctcaac cgtgcggctg catgaaatcc tggccggttt gtctgatgcc   10140
aagctggcgg cctggccggc cagcttggcc gctgaagaaa ccgagcgccg ccgtctaaaa   10200
aggtgatgtg tatttgagta aaacagcttg cgtcatgcgg tcgctgcgta tatgatgcga   10260
tgagtaaata aacaaatacg caaggggaac gcatgaaggt tatcgctgta cttaaccaga   10320
aaggcgggtc aggcaagacg accatcgcaa cccatctagc ccgcgccctg caactcgccg   10380
gggccgatgt tctgttagtc gattccgatc cccaggggcag tgcccgcgat tgggcggccg   10440
tgcgggaaga tcaaccgcta accgttgtcg gcatcgaccg cccgacgatt gaccgcgacg   10500
tgaaggccat cggccggcgc gacttcgtag tgatcgacgg agcgcccag gcggcggact   10560 tggctgtgtc cgcgatcaag gcagccgact tcgtgctgat tccggtgcag ccaagcccctt   10620 acgacatatg ggccaccgcc gacctggtgg agctggttaa gcagcgcatt gaggtcacgg   10680
atggaaggct acaagcggcc tttgtcgtgt cgcgggcgat caaaggcacg cgcatcggcg   10740
gtgaggttgc cgaggcgctg gccgggtacg agctgcccat tcttga                  10786

<210> SEQ ID NO 12
<211> LENGTH: 10468
<212> TYPE: DNA
<213> ORGANISM: Artificial
<220> FEATURE:
<223> OTHER INFORMATION: Synthetic construct

<400> SEQUENCE: 12
gtcccgtatc acgcagcgcg tgagctaccc aggcactgcc gccgccggca caaccgttct     60
tgaatcagaa cccgagggcg acgctgcccg cgaggtccag gcgctggccg ctgaaattaa    120
atcaaaactc atttgagtta atgaggtaaa gagaaaatga gcaaaagcac aaacacgcta    180
agtgccggcc gtccgagcgc acgcagcagc aaggctgcaa cgttggccag cctggcagac    240
acgccagcca tgaagcgggt caactttcag ttgccggcgg aggatcacac caagctgaag    300
atgtacgcgg tacgccaagg caagaccatt accgagctgc tatctgaata catcgcgcag    360
ctaccagagt aaatgagcaa atgaataaat gagtagatga attttagcgg ctaaaggagg    420
cggcatggaa aatcaagaac aaccaggcac cgacgccgtg gaatgcccca tgtgtggagg    480
aacgggcggt tggccaggcg taagcggctg ggttgtctgc cggccctgca atggcactgg    540
aacccccaag cccgaggaat cggcgtgacg gtcgcaaacc atccggcccg gtacaaatcg    600
gcgcggcgct gggtgatgac ctggtggaga gttgaaggc cgcgcaggcc gcccagcggc    660
aacgcatcga ggcagaagca cgccccgtg aatcgtggca agcggccgct gatcgaatcc    720
gcaaagaatc ccggcaaccg ccggcagccg gtgcgccgtc gattaggaag ccgcccaagg    780
gcgacgagca accagattt ttcgttccga tgctctatga cgtgggcacc cgcgatagtc    840
gcagcatcat ggacgtggcc gttttccgtc tgtcgaagcg tgaccgacga gctggcgagg    900
```

```
tgatccgcta cgagcttcca gacgggcacg tagaggtttc cgcagggccg gccggcatgg      960
ccagtgtgtg ggattacgac ctggtactga tggcggtttc ccatctaacc gaatccatga     1020
accgataccg ggaagggaag ggagacaagc ccggccgcgt gttccgtcca cacgttgcgg     1080
acgtactcaa gttctgccgg cgagccgatg gcggaaagca gaaagacgac ctggtagaaa     1140
cctgcattcg gttaaacacc acgcacgttg ccatgcagcg tacgaagaag gccaagaacg     1200
gccgcctggt gacggtatcc gagggtgaag ccttgattag ccgctacaag atcgtaaaga     1260
gcgaaaccgg gcggccggag tacatcgaga tcgagctagc tgattggatg taccgcgaga     1320
tcacagaagg caagaacccg gacgtgctga cggttcaccc cgattacttt ttgatcgatc     1380
ccggcatcgg ccgttttctc taccgcctgg cacgccgcgc cgcaggcaag gcagaagcca     1440
gatggttgtt caagacgatc tacgaacgca gtggcagcgc cggagagttc aagaagttct     1500
gtttcaccgt gcgcaagctg atcgggtcaa atgacctgcc ggagtacgat ttgaaggagg     1560
aggcggggca ggctggcccg atcctagtca tgcgctaccg caacctgatc gagggcgaag     1620
catccgccgg ttcctaatgt acggagcaga tgctagggca aattgcccta gcaggggaaa     1680
aaggtcgaaa aggtctcttt cctgtggata gcacgtacat tgggaaccca aagccgtaca     1740
ttgggaaccg gaacccgtac attgggaacc caaagccgta cattgggaac cggtcacaca     1800
tgtaagtgac tgatataaaa gagaaaaaag gcgattttc cgcctaaaac tctttaaaac      1860
ttattaaaac tcttaaaacc cgcctggcct gtgcataact gtctggccag cgcacagccg     1920
aagagctgca aaaagcgcct acccttcggt cgctgcgctc cctacgcccc gccgcttcgc     1980
gtcggcctat cgcggccgct ggccgctcaa aaatggctgg cctacggcca gcaatctac      2040 cagggcgcgc acaagccgcg ccgtcgccac tcgaccgccg gcgcccacat caaggcaccc     2100
tgcctcgcgc gtttcggtga tgacggtgaa aacctctgac acatgcagct cccggagacg     2160
gtcacagctt gtctgtaagc ggatgccggg agcagacaag cccgtcaggg cgcgtcagcg     2220
ggtgttggcg ggtgtcgggg cgcagccatg acccagtcac gtagcgatag cggagtgtat     2280
actggcttaa ctatgcggca tcagagcaga ttgtactgag agtgcaccat atgcggtgtg     2340
aaataccgca cagatgcgta aggagaaaat accgcatcag gcgctcttcc gcttcctcgc     2400
tcactgactc gctgcgctcg tcgttcggc tgcggcgagc ggtatcagct cactcaaagg     2460
cggtaatacg gttatccaca gaatcagggg ataacgcagg aaagaacatg tgagcaaaag     2520
gccagcaaaa ggccaggaac cgtaaaaagg ccgcgttgct ggcgtttttc cataggctcc     2580
gcccccctga cgagcatcac aaaaatcgac gctcaagtca gaggtggcga aacccgacag     2640
gactataaag ataccaggcg tttccccctg gaagctccct cgtgcgctct cctgttccga     2700
ccctgccgct taccggatac ctgtccgcct ttctcccttc gggaagcgtg gcgctttctc     2760
atagctcacg ctgtaggtat ctcagttcgg tgtaggtcgt tcgctccaag ctgggctgtg     2820
tgcacgaacc ccccgttcag cccgaccgct gcgccttatc cggtaactat cgtcttgagt     2880
ccaacccggt aagacacgac ttatcgccac tggcagcagc cactggtaac aggattagca     2940
gagcgaggta tgtaggcggt gctacagagt tcttgaagtg gtggcctaac tacggctaca     3000
ctagaaggac agtatttggt atctgcgctc tgctgaagcc agttaccttc ggaaaaagag     3060
ttggtagctc ttgatccggc aaacaaacca ccgctggtag cggtggtttt tttgtttgca     3120
agcagcagat tacgcgcaga aaaaaaggat ctcaagaaga tcctttgatc ttttctacgg     3180
ggtctgacgc tcagtggaac gaaaactcac gttaagggat tttggtcatg catgatatat     3240
ctcccaattt gtgtagggct tattatgcac gcttaaaaat aataaaagca gacttgacct     3300
```

```
gatagtttgg ctgtgagcaa ttatgtgctt agtgcatcta atcgcttgag ttaacgccgg   3360
cgaagcggcg tcggcttgaa cgaatttcta gctagacatt atttgccgac taccttggtg   3420
atctcgcctt tcacgtagtg gacaaattct tccaactgat ctgcgcgcga ggccaagcga   3480
tcttcttctt gtccaagata agcctgtcta gcttcaagta tgacgggctg atactgggcc   3540
ggcaggcgct ccattgccca gtcggcagcg acatccttcg gcgcgatttt gccggttact   3600
gcgctgtacc aaatgcggga caacgtaagc actacatttc gctcatcgcc agcccagtcg   3660
ggcggcgagt tccatagcgt taaggtttca tttagcgcct caaatagatc ctgttcagga   3720
accggatcaa agagttcctc cgccgctgga cctaccaagg caacgctatg ttctcttgct   3780
tttgtcagca agatagccag atcaatgtcg atcgtggctg gctcgaagat acctgcaaga   3840
atgtcattgc gctgccattc tccaaattgc agttcgcgct tagctggata acgccacgga   3900
atgatgtcgt cgtgcacaac aatggtgact tctacagcgc ggagaatctc gctctctcca   3960
ggggaagccg aagtttccaa aaggtcgttg atcaaagctc gccgcgttgt tcatcaagc    4020 cttacggtca ccgtaaccag caaatcaata tcactgtgtg gcttcaggcc gccatccact   4080
gcggagccgt acaaatgtac ggccagcaac gtcggttcga gatggcgctc gatgacgcca   4140
actacctctg atagttgagt cgatacttcg gcgatcaccg cttcccccat gatgtttaac   4200 tttgtttttag ggcgactgcc ctgctgcgta acatcgttgc tgctccataa catcaaacat   4260
cgacccacgg cgtaacgcgc ttgctgcttg gatgcccgag gcatagactg taccccaaaa   4320
aaacatgtca taacaagaag ccatgaaaac cgccactgcg ccgttaccac cgctgcgttc   4380
ggtcaaggtt ctggaccagt tgcgtgacgg cagttacgct acttgcatta cagcttacga   4440
accgaacgag gcttatgtcc actgggttcg tgcccgaatt gatcacaggc agcaacgctc   4500
tgtcatcgtt acaatcaaca tgctaccctc cgcgagatca tccgtgtttc aaacccggca   4560
gcttagttgc cgttcttccg aatagcatcg gtaacatgag caaagtctgc cgccttacaa   4620
cggctctccc gctgacgccg tcccggactg atgggctgcc tgtatcgagt ggtgattttg   4680
tgccgagctg ccggtcgggg agctgttggc tggctggtgg caggatatat tgtggtgtaa   4740
acaaattgac gcttagacaa cttaataaca cattgcggac gtttttaatg tactgaatta   4800
acgccgaatt gaattcctcg agtacgtagg atccatttaa attctagagg cgcgccgata   4860
tcctctctta aggtagcgag ctcttaatta atagggataa cagggtaatg cggccgcaag   4920
ctaaaacgac ggccagtgaa ttatcaactt tgtatagaaa agttgctctg ccgacagtgg   4980
tcccaaagat ggacccccac ccacgaggag catcgtggaa aagaagacg ttccaaccac    5040 gtcttcaaag caagtggatt gatgtgtaaa catggtggag cacgacactc tcgtctactc   5100
caagaatatc aaagatacag tctcagaaga ccaaagggct attgagactt tcaacaaag    5160 ggtaatatcg ggaaacctcc tcggattcca ttgcccagct atctgtcact tcatcaaaag   5220
gacagtagaa aaggaaggtg gcacctacaa atgccatcat tgcgataaag gaaaggctat   5280
cgttcaagat gcctctgccg acagtggtcc caaagatgga cccccaccca cgaggagcat   5340
cgtggaaaaa gaagacgttc caaccacgtc ttcaaagcaa gtggattgat gtgatatctc   5400
cactgacgta aggatgacg cacaatccca ctatccttcg caagacccctt cctctatata   5460 aggaagttca tttcatttgg agaggacacg ctgcaagttt gtacaaaaaa gcaggctatg   5520
gcaattacct tatccgcaac ttctttacct atttccgccc ggatccgggc aggttctccg   5580
gccgcttggg tggagaggct attcggctat gactgggcac aacagacaat cggctgctct   5640
gatgccgccg tgttccggct gtcagcgcag gggcgcccgg ttcttttgt caagaccgac    5700
```

```
ctgtccggtg ccctgaatga actgcaggac gaggcagcgc ggctatcgtg gctggccacg   5760
acgggcgttc cttgcgcagc tgtgctcgac gttgtcactg aagcgggaag ggactggctg   5820
ctattgggcg aagtgccggg gcaggatctc ctgtcatctc accttgctcc tgccgagaaa   5880
gtatccatca tggctgatgc aatgcggcgg ctgcatacgc ttgatccggc tacctgccca   5940
ttcgaccacc aagcgaaaca tcgcatcgag cgagcacgta ctcggatgga agccggtctt   6000
gtcgatcagg atgatctgga cgaagagcat caggggctcg cgccagccga actgttcgcc   6060
aggctcaagg cgcgcatgcc cgacggcgag gatctcgtcg tgacccatgg cgatgcctgc   6120
ttgccgaata tcatggtgga aaatggccgc ttttctggat tcatcgactg tggccggctg   6180
ggtgtggcgg accgctatca ggacatagcg ttggctaccc gtgatattgc tgaagagctt   6240
ggcggcgaat gggctgaccg cttcctcgtg ctttacggta tcgccgctcc cgattcgcag   6300
cgcatcgcct tctatcgcct tcttgacgag ttccttctga cccagctttc ttgtacaaag   6360
tggagtccgc aaaaatcacc agtctctctc tacaaatcta tctctctcta tttttctcca   6420
gaataatgtg tgagtagttc ccagataagg gaattagggt tcttatatggg tttcgctcat   6480
gtgttgagca tataagaaac ccttagtatg tatttgtatt tgtaaaatac ttctatcaat   6540
aaaatttcta attcctaaaa ccaaaatcca gtgacctcaa ctttattata catagttgat   6600
aattcactgg ccgtgcttat tccatggctg caggtcgacg aattcaccgg ttagggataa   6660
cagggtaata actataacgg tcctaaggta gcgagcggcc gcaagctaaa acgacggcca   6720
gtgaattatc aactttgtat agaaaagttg gtttgtgtct tctagattaa tcctccaaac   6780
ttttgattaa ccaaaaaaat tatcaaacta acatgttctc cttttttctt tagaaattct   6840
aacgaattta tctttatact gatttgaata tacttaattt ggtcatttgg atgcccttta   6900
caacctcctt accaaaatat tgatcacagt ttctattgct aaaatcacca acaaaacgca   6960
tgtcgccatt cataattatg gtttcacacc tacaactagg ctaataagta aataagtaga   7020
caactagact caggtttgaa aaaaccataa aagccatata gcgttttctc attgaaactg   7080
cgaacacgat cgtgtgaatg ttgcagtttc tagttttgat acaaacaaac aaaaacacaa   7140
tttaatctta gattaaaaag aaaaaagaga acggagccca ctagccactc cttcaaacgt   7200
gtcttaccaa ctctcttcta gaaacaaatt aggcttcacc ttcctcttcc aacctctctc   7260
tctctctctc tctctctttc tcaaaccatc tctccataaa gccctaattt cttcatcaca   7320
agaatcagaa gaagaaacaa gtttgtacaa aaaagcaggc ttactgcaaa aaacttatgg   7380
acctgcatct aattttcggt ccaacttgca caggaaagac gacgaccgcg atagctcttg   7440
cccagcagac agggcttcca gtcctttcgc ttgatcgggt ccaatgctgt cctcaactat   7500
caaccggaag cggacgacca acagtggaag aactgaaagg aacgacgcgt ctctaccttg   7560
atgatcggcc tctggtggag ggtatcatcg cagccaagca agctcatcat aggctgatcg   7620
aggaggtgta taatcatgag gccaacggcg ggcttattct tgagggagga tccacctcgt   7680
tgctcaactg catggcgcga aacagctatt ggagtgcaga ttttcgttgg catattattc   7740
gccacaagtt acccgaccaa gagaccttca tgaaagcggc caaggccaga gttaagcaga   7800
tgttgcaccc cgctgcaggc cattctatta ttcaagagtt ggtttatctt tggaatgaac   7860
ctcggctgag gcccattctg aaagagatcg atggatatcg atatgccatg ttgtttgcta   7920
gccagaacca gatcacggca gatatgctat tgcagcttga cgcaaatatg gaaggtaagt   7980
tgattaatgg gatcgctcag gagtatttca tccatgcgcg ccaacaggaa cagaaattcc   8040
cccaagttaa cgcagccgct ttcgacggat tcgaaggtca tccgttcgga atgtattagg   8100
```

```
tacccagctt tcttgtacaa agtgggatcg ttcaaacatt tggcaataaa gtttcttaag   8160
attgaatcct gttgccggtc ttgcgatgat tatcatataa tttctgttga attacgttaa   8220
gcatgtaata attaacatgt aatgcatgac gttatttatg agatgggttt ttatgattag   8280
agtcccgcaa ttatacattt aatacgcgat agaaaacaaa atatagcgcg caaactagga   8340
taaattatcg cgcgcggtgt catctatgtt actagatcca actttattat acatagttga   8400
taattcactg gccgtcgctt attccatggc tgcaggtcga cgaattcacc ggttaactat   8460
aacggtccta aggtagcgat ggcaaacagc tattatgggt attatgggtg gttctttatg   8520
cggacactga cggctttatg cctgcaggtc gcgagcgatc gcggtaccgc ccgggcgtcg   8580
acaggcctaa gcttagcttg agcttggatc agattgtcgt ttcccgcctt cagtttaaac   8640
tatcagtgtt tgacaggata tattggcggg taaacctaag agaaaagagc gtttattaga   8700
ataacggata tttaaaaggg cgtgaaaagg tttatccgtt cgtccatttg tatgtgcatg   8760
ccaaccacag ggttcccctc gggatcaaag tactttgatc caacccctcc gctgctatag   8820
tgcagtcggc ttctgacgtt cagtgcagcc gtcttctgaa aacgacatgt cgcacaagtc   8880
ctaagttacg cgacaggctg ccgccctgcc ctttcctgg cgtttcttg tcgcgtgttt   8940
tagtcgcata aagtagaata cttgcgacta gaaccggaga cattacgcca tgaacaagag   9000
cgccgccgct ggcctgctgg gctatgcccg cgtcagcacc gacgaccagg acttgaccaa   9060
ccaacgggcc gaactgcacg cggccggctg caccaagctg ttttccgaga agatcaccgg   9120
caccaggcgc gaccgcccgg agctggccag gatgcttgac cacctacgcc ctggcgacgt   9180
tgtgacagtg accaggctag accgcctggc ccgcagcacc cgcgacctac tggacattgc   9240
cgagcgcatc caggaggccg gcgcgggcct cgtagcctg gcagagccgt gggccgacac   9300
caccacgccg gccggccgca tggtgttgac cgtgttcgcc ggcattgccg agttcgagcg   9360
ttccctaatc atcgaccgca cccggagcgg gcgcgaggcc gccaaggccc gaggcgtgaa   9420
gtttggcccc cgccctaccc tcaccccggc acagatcgcg cacgcccgcg agctgatcga   9480
ccaggaaggc cgcaccgtga agaggcggc tgcactgctt ggcgtgcatc gctcgaccct   9540
gtaccgcgca cttgagcgca gcgaggaagt gacgcccacc gaggccaggc ggcgcggtgc   9600
cttccgtgag gacgcattga ccgaggccga cgccctggcg gccgccgaga atgaacgcca   9660
agaggaacaa gcatgaaacc gcaccaggac ggccaggacg aaccgttttt cattaccgaa   9720
gagatcgagg cggagatgat cgcggccggg tacgtgttcg agccgccgc gcacgtctca   9780
accgtgcggc tgcatgaaat cctggccggt ttgtctgatg ccaagctggc ggcctggccg   9840
gccagcttgg ccgctgaaga aaccgagcgc cgccgtctaa aaaggtgatg tgtatttgag   9900
taaaacagct tgcgtcatgc ggtcgctgcg tatatgatgc gatgagtaaa taaacaaata   9960
cgcaagggga acgcatgaag gttatcgctg tacttaacca gaaaggcggg tcaggcaaga  10020
cgaccatcgc aacccatcta gcccgcgccc tgcaactcgc cggggccgat gttctgttag  10080
tcgattccga tccccagggc agtgcccgcg attgggcggc cgtgcgggaa gatcaaccgc  10140
taaccgttgt cggcatcgac cgcccgacga ttgaccgcga cgtgaaggcc atcggccggc  10200
gcgacttcgt agtgatcgac ggagcgcccc aggcggcgga cttggctgtg tccgcgatca  10260
aggcagccga cttcgtgctg attccggtgc agccaagccc ttacgacata tgggccaccg  10320
ccgacctggt ggagctggtt aagcagcgca ttgaggtcac ggatggaagg ctacaagcgg  10380
cctttgtcgt gtcgcgggcg atcaaaggca cgcgcatcgg cggtgaggtt gccgaggcgc  10440
tggccgggta cgagctgccc attcttga                                     10468
```

<210> SEQ ID NO 13
<211> LENGTH: 11000
<212> TYPE: DNA
<213> ORGANISM: Artificial
<220> FEATURE:
<223> OTHER INFORMATION: Synthetic construct

<400> SEQUENCE: 13

| | | | | | |
|---|---|---|---|---|---|
| gtcccgtatc | acgcagcgcg | tgagctaccc | aggcactgcc | gccgccggca | caaccgttct | 60 |
| tgaatcagaa | cccgagggcg | acgctgcccg | cgaggtccag | gcgctggccg | ctgaaattaa | 120 |
| atcaaaactc | atttgagtta | atgaggtaaa | gagaaaatga | gcaaaagcac | aaacacgcta | 180 |
| agtgccggcc | gtccgagcgc | acgcagcagc | aaggctgcaa | cgttggccag | cctggcagac | 240 |
| acgccagcca | tgaagcgggt | caactttcag | ttgccggcgg | aggatcacac | caagctgaag | 300 |
| atgtacgcgg | tacgccaagg | caagaccatt | accgagctgc | tatctgaata | catcgcgcag | 360 |
| ctaccagagt | aaatgagcaa | atgaataaat | gagtagatga | attttagcgg | ctaaaggagg | 420 |
| cggcatggaa | aatcaagaac | aaccaggcac | cgacgccgtg | gaatgcccca | tgtgtggagg | 480 |
| aacgggcggt | tggccaggcg | taagcggctg | ggttgtctgc | cggccctgca | atggcactgg | 540 |
| aacccccaag | cccgaggaat | cggcgtgacg | gtcgcaaacc | atccggcccg | gtacaaatcg | 600 |
| gcgcggcgct | gggtgatgac | ctggtggaga | agttgaaggc | cgcgcaggcc | gcccagcggc | 660 |
| aacgcatcga | ggcagaagca | cgccccggtg | aatcgtggca | agcggccgct | gatcgaatcc | 720 |
| gcaaagaatc | ccggcaaccg | ccggcagccg | gtgcgccgtc | gattaggaag | ccgcccaagg | 780 |
| gcgacgagca | accagatttt | ttcgttccga | tgctctatga | cgtgggcacc | cgcgatagtc | 840 |
| gcagcatcat | ggacgtggcc | gttttccgtc | tgtcgaagcg | tgaccgacga | gctggcgagg | 900 |
| tgatccgcta | cgagcttcca | gacgggcacg | tagaggtttc | cgcagggccg | ccggcatgg | 960 |
| ccagtgtgtg | ggattacgac | ctggtactga | tggcggtttc | ccatctaacc | gaatccatga | 1020 |
| accgataccg | ggaagggaag | ggagacaagc | ccggccgcgt | gttccgtcca | cacgttgcgg | 1080 |
| acgtactcaa | gttctgccgg | cgagccgatg | gcggaaagca | gaaagacgac | ctggtagaaa | 1140 |
| cctgcattcg | gttaaacacc | acgcacgttg | ccatgcagcg | tacgaagaag | gccaagaacg | 1200 |
| gccgcctggt | gacggtatcc | gagggtgaag | ccttgattag | ccgctacaag | atcgtaaaga | 1260 |
| gcgaaaccgg | gcggccggag | tacatcgaga | tcgagctagc | tgattggatg | taccgcgaga | 1320 |
| tcacagaagg | caagaacccg | gacgtgctga | cggttcaccc | cgattacttt | ttgatcgatc | 1380 |
| ccggcatcgg | ccgttttctc | taccgcctgg | cacgccgcgc | cgcaggcaag | gcagaagcca | 1440 |
| gatggttgtt | caagacgatc | tacgaacgca | gtggcagcgc | cggagagttc | aagaagttct | 1500 |
| gtttcaccgt | gcgcaagctg | atcgggtcaa | atgacctgcc | ggagtacgat | ttgaaggagg | 1560 |
| aggcggggca | ggctggcccg | atcctagtca | tgcgctaccg | caacctgatc | gagggcgaag | 1620 |
| catccgccgg | ttcctaatgt | acggagcaga | tgctagggca | aattgcccta | gcagggggaaa | 1680 |
| aaggtcgaaa | aggtctcttt | cctgtggata | gcacgtacat | tgggaaccca | aagccgtaca | 1740 |
| ttgggaaccg | gaacccgtac | attgggaacc | caaagccgta | cattgggaac | cggtcacaca | 1800 |
| tgtaagtgac | tgatataaaa | gagaaaaaag | gcgatttttc | cgcctaaaac | tctttaaaac | 1860 |
| ttattaaaac | tcttaaaacc | cgcctggcct | gtgcataact | gtctggccag | cgcacagccg | 1920 |
| aagagctgca | aaaagcgcct | acccttcggt | cgctgcgctc | cctacgcccc | gccgcttcgc | 1980 |
| gtcggcctat | cgcggccgct | ggccgctcaa | aaatggctgg | cctacggcca | ggcaatctac | 2040 |
| cagggcgcgg | acaagccgcg | ccgtcgccac | tcgaccgccg | gcgcccacat | caaggcaccc | 2100 |

```
tgcctcgcgc gtttcggtga tgacggtgaa aacctctgac acatgcagct cccggagacg    2160
gtcacagctt gtctgtaagc ggatgccggg agcagacaag cccgtcaggg cgcgtcagcg    2220
ggtgttggcg ggtgtcgggg cgcagccatg acccagtcac gtagcgatag cggagtgtat    2280
actggcttaa ctatgcggca tcagagcaga ttgtactgag agtgcaccat atgcggtgtg    2340
aaataccgca cagatgcgta aggagaaaat accgcatcag cgctcttcc gcttcctcgc     2400 tcactgactc gctgcgctcg gtcgttcggc tgcggcgagc ggtatcagct cactcaaagg    2460
cggtaatacg gttatccaca gaatcagggg ataacgcagg aaagaacatg tgagcaaaag    2520
gccagcaaaa ggccaggaac cgtaaaaagg ccgcgttgct ggcgtttttc cataggctcc    2580
gcccccctga cgagcatcac aaaaatcgac gctcaagtca gaggtggcga acccgacag     2640 gactataaag ataccaggcg tttccccctg gaagctccct cgtgcgctct cctgttccga    2700
ccctgccgct taccggatac ctgtccgcct ttctcccttc gggaagcgtg gcgctttctc    2760
atagctcacg ctgtaggtat ctcagttcgg tgtaggtcgt tcgctccaag ctgggctgtg    2820
tgcacgaacc ccccgttcag cccgaccgct gcgccttatc cggtaactat cgtcttgagt    2880
ccaacccggt aagacacgac ttatcgccac tggcagcagc cactggtaac aggattagca    2940
gagcgaggta tgtaggcggt gctacagagt tcttgaagtg gtggcctaac tacggctaca    3000
ctagaaggac agtatttggt atctgcgctc tgctgaagcc agttaccttc ggaaaaagag    3060
ttggtagctc ttgatccggc aaacaaacca ccgctggtag cggtggtttt tttgtttgca    3120
agcagcagat tacgcgcaga aaaaaaggat ctcaagaaga tcctttgatc ttttctacgg    3180
ggtctgacgc tcagtggaac gaaaactcac gttaagggat tttggtcatg catgatatat    3240
ctcccaattt gtgtagggct tattatgcac gcttaaaaat aataaaagca gacttgacct    3300
gatagtttgg ctgtgagcaa ttatgtgctt agtgcatcta atcgcttgag ttaacgccgg    3360
cgaagcggcg tcggcttgaa cgaatttcta gctagacatt atttgccgac taccttggtg    3420
atctcgcctt tcacgtagtg gacaaattct tccaactgat ctgcgcgcga ggccaagcga    3480
tcttcttctt gtccaagata agcctgtcta gcttcaagta tgacgggctg atactgggcc    3540
ggcaggcgct ccattgccca gtcggcagcg acatccttcg gcgcgatttt gccggttact    3600
gcgctgtacc aaatgcggga caacgtaagc actacatttc gctcatcgcc agcccagtcg    3660
ggcggcgagt tccatagcgt taaggtttca tttagcgcct caaatagatc ctgttcagga    3720
accggatcaa agagttcctc cgccgctgga cctaccaagg caacgctatg ttctcttgct    3780
tttgtcagca agatagccag atcaatgtcg atcgtggctg gctcgaagat acctgcaaga    3840
atgtcattgc gctgccattc tccaaattgc agttcgcgct tagctggata acgcacgga    3900 atgatgtcgt cgtgcacaac aatggtgact tctacagcgc ggagaatctc gctctctcca    3960
ggggaagccg aagtttccaa aaggtcgttg atcaaagctc gccgcgttgt ttcatcaagc    4020
cttacggtca ccgtaaccag caaatcaata tcactgtgtg gcttcaggcc gccatccact    4080
gcggagccgt acaaatgtac ggccagcaac gtcggttcga gatggcgctc gatgacgcca    4140
actacctctg atagttgagt cgatacttcg gcgatcaccg cttccccat gatgtttaac     4200 tttgttttag gcgactgccc tgctgcgta acatcgttgc tgctccataa catcaaacat     4260
cgacccacgg cgtaacgcgc ttgctgcttg gatgcccgag gcatagactg taccccaaaa    4320
aaacatgtca taacaagaag ccatgaaaac cgccactgcg ccgttaccac cgctgcgttc    4380
ggtcaaggtt ctgaccagt tgcgtgacgg cagttacgct acttgcatta cagcttacga    4440
accgaacgag gcttatgtcc actgggttcg tgcccgaatt gatcacaggc agcaacgctc    4500
```

```
tgtcatcgtt acaatcaaca tgctaccctc cgcgagatca tccgtgtttc aaacccggca   4560
gcttagttgc cgttcttccg aatagcatcg gtaacatgag caaagtctgc cgccttacaa   4620
cggctctccc gctgacgccg tcccggactg atgggctgcc tgtatcgagt ggtgattttg   4680
tgccgagctg ccggtcgggg agctgttggc tggctggtgg caggatatat tgtggtgtaa   4740
acaaattgac gcttagacaa cttaataaca cattgcggac gtttttaatg tactgaatta   4800
acgccgaatt gaattcctcg agtacgtagg atccatttaa attctagagg cgcgccgata   4860
tcctctctta aggtagcgag ctcttaatta atagggataa cagggtaatg cggccgcaag   4920
ctaaaacgac ggccagtgaa ttatcaactt tgtatagaaa agttgctctg ccgacagtgg   4980
tcccaaagat ggacccccac ccacgaggag catcgtggaa aaagaagacg ttccaaccac   5040
gtcttcaaag caagtggatt gatgtgataa catggtggag cacgacactc tcgtctactc   5100
caagaatatc aaagatacag tctcagaaga ccaaagggct attgagactt ttcaacaaag   5160
ggtaatatcg gaaacctcc tcggattcca ttgcccagct atctgtcact tcatcaaaag   5220
gacagtagaa aaggaaggtg gcacctacaa atgccatcat tgcgataaag gaaaggctat   5280
cgttcaagat gcctctgccg acagtggtcc caaagatgga cccccaccca cgaggagcat   5340
cgtggaaaaa gaagacgttc caaccacgtc ttcaaagcaa gtggattgat gtgatatctc   5400
cactgacgta agggatgacg cacaatccca ctatccttcg caagaccctt cctctatata   5460
aggaagttca tttcatttgg agaggacacg ctgcaagttt gtacaaaaaa gcaggctaga   5520 ccgggggca atgagatatg aaaaagcctg aactcaccgc gacgtctgtc gagaagtttc   5580
tgatcgaaaa gttcgacagc gtctccgacc tgatgcagct ctcggagggc gaagaatctc   5640
gtgctttcag cttcgatgta ggagggcgtg gatatgtcct gcgggtaaat agctgcgccg   5700
atggtttcta caaagatcgt tatgtttatc ggcactttgc atcggccgcg ctcccgattc   5760
cggaagtgct tgacattggg gaattcagcg agagcctgac ctattgcatc tcccgccgtg   5820
cacagggtgt cacgttgcaa gacctgcctg aaaccgaact gcccgctgtt ctgcagccgg   5880
tcgcggaggc catggatgcg atcgctgcgg ccgatcttag ccagacgagc gggttcggcc   5940
cattcggacc gcaaggaatc ggtcaataca ctacatggcg tgatttcata tgcgcgattg   6000
ctgatcccca tgtgtatcac tggcaaactg tgatggacga caccgtcagt gcgtccgtcg   6060
cgcaggctct cgatgagctg atgctttggg ccgaggactg ccccgaagtc cggcacctcg   6120
tgcacgcgga tttcggctcc aacaatgtcc tgacggacaa tggccgcata acagcggtca   6180
ttgactggag cgaggcgatg ttcggggatt cccaatacga ggtcgccaac atcttcttct   6240
ggaggccgtg gttggcttgt atggagcagc agacgcgcta cttcgagcgg aggcatccgg   6300
agcttgcagg atcgccgcgg ctccgggcgt atatgctccg cattggtctt gaccaactct   6360
atcagagctt ggttgacggc aatttcgatg atgcagcttg ggcgcagggt cgatgcgacg   6420
caatcgtccg atccggagcc gggactgtcg gcgtacaca atcgcccgc agaagcgcgg   6480 ccggccgtct ggaccgatgg ctgtgtagaa gtactcgccg atagtggaaa ccgacgcccc   6540
agcactcgtc cggacccagc tttcttgtac aaagtggagt ccgcaaaaat caccagtctc   6600
tctctacaaa tctatctctc tctattttc tccagaataa tgtgtgagta gttcccagat   6660
aagggaatta gggttcttat agggtttcgc tcatgtgttg agcatataag aaacccttag   6720
tatgtatttg tatttgtaaa atacttctat caataaaatt tctaattcct aaaaccaaaa   6780
tccagtgacc tcaactttat tatacatagt tgataattca ctggccgtgc ttattccatg   6840
gctgcaggtc gacgaattca ccggttaggg ataacagggt aatcgctacc ttaggaccgt   6900
```

```
tatagttacg gccagtgcca ttaccctgtt atccctaacc ggtgacaact ttgtatagaa   6960
aagttggttt gtgtcttcta gattaatcct ccaaacttt gattaaccaa aaaaattatc   7020
aaactaacat gttctccttt tttctttaga aattctaacg aatttatctt tatactgatt   7080
tgaatatact taatttggtc atttggatgc cctttacaac ctccttacca aactcactat   7140
ggcaaatata tactattttc cattgtaaca taaatgtcca taatttgaat taaattcgtt   7200
gcagtacgaa accatccaac tttgtccaaa aacaaaatcc ttataactat ttactttaat   7260
gtaaatatat cctctacttt tgttttaca accctagctc aaacaaattt attatttgcg   7320
ataaaaaatc atatcgaaca aactcgatga ttttttttt cttacgttat taatgaaact   7380
aaaatataga aaaaaacaag atgaaccaaa ttttcaccta tctaactact taaatataat   7440
atgattaaat ttggtaaagt ttgaaaagtt tctttagaaa tgtgaaatat tgatcacagt   7500
ttctattgct aaaatcacca acaaaacgca tgtcgccatt cataattatg gtttcacacc   7560
tacaactagg ctaataagta aataagtaga caactagact caggtttgaa aaaccataa   7620 aagccatata gcgttttctc attgaaactg cgaacacgat cgtgtgaatg ttgcagtttc   7680
tagttttgat acaaacaaac aaaaacacaa tttaatctta gattaaaaag aaaaaagaga   7740
acggagccca ctagccactc cttcaaacgt gtcttaccaa ctctcttcta gaaacaaatt   7800
aggcttcacc ttcctcttcc aacctctctc tctctctctc tctcttttc tcaaaccatc   7860 tctccataaa gccctaattt cttcatcaca agaatcagaa gaagaaacaa gtttgtacaa   7920
aaaagcaggc ttactgcaaa aaacttatgg acctgcatct aattttcggt ccaacttgca   7980
caggaaagac gacgaccgcg atagctcttg cccagcagac agggcttcca gtcctttcgc   8040
ttgatcgggt ccaatgctgt cctcaactat caaccggaag cggacgacca acagtggaag   8100
aactgaaagg aacgacgcgt ctctaccttg atgatcggcc tctggtggag ggtatcatcg   8160
cagccaagca agctcatcat aggctgatcg aggaggtgta taatcatgag gccaacggcg   8220
ggcttattct tgagggagga tccacctcgt tgctcaactg catggcgcga aacagctatt   8280
ggagtgcaga ttttcgttgg catattattc gccacaagtt acccgaccaa gagaccttca   8340
tgaaagcggc caaggccaga gttaagcaga tgttgcaccc cgctgcaggc cattctatta   8400
ttcaagagtt ggtttatctt tggaatgaac ctcggctgag gcccattctg aaagagatcg   8460
atggatatcg atatgccatg ttgtttgcta gccagaacca gatcacggca gatatgctat   8520
tgcagcttga cgcaaatatg gaaggtaagt tgattaatgg gatcgctcag gagtatttca   8580
tccatgcgcg ccaacaggaa cagaaattcc cccaagttaa cgcagccgct ttcgacggat   8640
tcgaaggtca tccgttcgga atgtattagg tacccagctt tcttgtacaa agtgggatcg   8700
ttcaaacatt tggcaataaa gtttcttaag attgaatcct gttgccggtc ttgcgatgat   8760
tatcatataa tttctgttga attacgttaa gcatgtaata attaacatgt aatgcatgac   8820
gttatttatg agatgggttt ttatgattag agtcccgcaa ttatacattt aatacgcgat   8880
agaaaacaaa atatagcgcg caaactagga taaattatcg cgcgcggtgt catctatgtt   8940
actagatcca actttattat acatagttga ttcgtcgacc tgcagtcgct accttaggac   9000
cgttatagtt atggcaaaca gctattatgg gtattatggg tggttcttta tgcggacact   9060
gacggcttta tgcctgcagg tcgcgagcga tcgcggtacc gcccgggcgt cgacaggcct   9120
aagcttagct tgagcttgga tcagattgtc gtttcccgcc ttcagtttaa actatcagtg   9180
tttgacagga tatattggcg ggtaaaccta agagaaaaga gcgttattat gaataacgga   9240
tatttaaaag ggcgtgaaaa ggtttatccg ttcgtccatt tgtatgtgca tgccaaccac   9300
```

```
agggttcccc tcgggatcaa agtactttga tccaacccct ccgctgctat agtgcagtcg   9360
gcttctgacg ttcagtgcag ccgtcttctg aaaacgacat gtcgcacaag tcctaagtta   9420
cgcgacaggc tgccgccctg ccctttcct ggcgttttct tgtcgcgtgt tttagtcgca    9480
taaagtagaa tacttgcgac tagaaccgga gacattacgc catgaacaag agcgccgccg   9540
ctggcctgct gggctatgcc cgcgtcagca ccgacgacca ggacttgacc aaccaacggg   9600
ccgaactgca cgcggccggc tgcaccaagc tgttttccga aagatcacc ggcaccaggc    9660 gcgaccgccc ggagctggcc aggatgcttg accacctacg ccctggcgac gttgtgacag   9720
tgaccaggct agaccgcctg gcccgcagca cccgcgacct actggacatt gccgagcgca   9780
tccaggaggc cggcgcgggc ctgcgtagcc tggcagagcc gtgggccgac accaccacgc   9840
cggccggccg catggtgttg accgtgttcg ccggcattgc cgagttcgag cgttccctaa   9900
tcatcgaccg cacccggagc gggcgcgagg ccgccaaggc ccgaggcgtg aagtttggcc   9960
cccgccctac cctcaccccg gcacagatcg cgcacgcccg cgagctgatc gaccaggaag  10020
gccgcaccgt gaaagaggcg gctgcactgc ttggcgtgca tcgctcgacc ctgtaccgcg  10080
cacttgagcg cagcgaggaa gtgacgccca ccgaggccag gcggcgcggt gccttccgtg  10140
aggacgcatt gaccgaggcc gacgccctgg cggccgccga aatgaacgc caagaggaac    10200 aagcatgaaa ccgcaccagg acggccagga cgaaccgttt tcattaccg aagagatcga    10260 ggcggagatg atcgcggccg ggtacgtgtt cgagccgccc gcgcacgtct caaccgtgcg  10320
gctgcatgaa atcctggccg gtttgtctga tgccaagctg gcggcctggc cggccagctt   10380
ggccgctgaa gaaaccgagc gccgccgtct aaaaaggtga tgtgtatttg agtaaaacag  10440
cttgcgtcat gcggtcgctg cgtatatgat gcgatgagta aataaacaaa tacgcaaggg  10500
gaacgcatga aggttatcgc tgtacttaac cagaaaggcg ggtcaggcaa gacgaccatc  10560
gcaacccatc tagcccgcgc cctgcaactc gccggggccg atgttctgtt agtcgattcc  10620
gatccccagg gcagtgcccg cgattgggcg ccgtgcggg aagatcaacc gctaaccgtt    10680
gtcggcatcg accgcccgac gattgaccgc gacgtgaagg ccatcggccg gcgcgacttc  10740
gtagtgatcg acggagcgcc ccaggcggcg gacttggctg tgtccgcgat caaggcagcc  10800
gacttcgtgc tgattccggt gcagccaagc ccttacgaca tatgggccac cgccgacctg  10860
gtggagctgg ttaagcagcg cattgaggtc acggatggaa ggctacaagc ggcctttgtc  10920
gtgtcgcggg cgatcaaagg cacgcgcatc ggcggtgagg ttgccgaggc gctggccggg  10980
tacgagctgc ccattcttga                                              11000
```

<210> SEQ ID NO 14
<211> LENGTH: 10682
<212> TYPE: DNA
<213> ORGANISM: Artificial
<220> FEATURE:
<223> OTHER INFORMATION: Synthetic construct

<400> SEQUENCE: 14

```
gtcccgtatc acgcagcgcg tgagctaccc aggcactgcc gccgccggca caaccgttct     60
tgaatcagaa cccgagggcg acgctgcccg cgaggtccag gcgctggccg ctgaaattaa    120
atcaaaactc atttgagtta atgaggtaaa gagaaaatga gcaaaagcac aaacacgcta    180
agtgccggcc gtccgagcgc acgcagcagc aaggctgcaa cgttggccag cctggcagac    240
acgccagcca tgaagcgggt caactttcag ttgccggcgg aggatcacac caagctgaag    300
atgtacgcgg tacgccaagg caagaccatt accgagctgc tatctgaata catcgcgcag    360
```

```
ctaccagagt aaatgagcaa atgaataaat gagtagatga attttagcgg ctaaaggagg    420
cggcatggaa aatcaagaac aaccaggcac cgacgccgtg gaatgcccca tgtgtggagg    480
aacgggcggt tggccaggcg taagcggctg ggttgtctgc cggccctgca atggcactgg    540
aaccccaag cccgaggaat cggcgtgacg gtcgcaaacc atccggcccg gtacaaatcg    600
gcgcggcgct gggtgatgac ctggtggaga agttgaaggc cgcgcaggcc gcccagcggc    660
aacgcatcga ggcagaagca cgccccggtg aatcgtggca agcggccgct gatcgaatcc    720
gcaaagaatc ccggcaaccg ccggcagccg gtgcgccgtc gattaggaag ccgcccaagg    780
gcgacgagca accagatttt ttcgttccga tgctctatga cgtgggcacc cgcgatagtc    840
gcagcatcat ggacgtggcc gttttccgtc tgtcgaagcg tgaccgacga gctggcgagg    900
tgatccgcta cgagcttcca gacgggcacg tagaggtttc cgcagggccg gccggcatgg    960
ccagtgtgtg ggattacgac ctggtactga tggcggtttc ccatctaacc gaatccatga   1020
accgataccg ggaagggaag ggagacaagc ccggccgcgt gttccgtcca cacgttgcgg   1080
acgtactcaa gttctgccgg cgagccgatg gcggaaagca gaaagacgac ctggtagaaa   1140
cctgcattcg gttaaacacc acgcacgttg ccatgcagcg tacgaagaag gccaagaacg   1200
gccgcctggt gacggtatcc gagggtgaag ccttgattag ccgctacaag atcgtaaaga   1260
gcgaaaccgg gcgccggag tacatcgaga tcgagctagc tgattggatg taccgcgaga   1320
tcacagaagg caagaacccg gacgtgctga cggttcaccc cgattacttt ttgatcgatc   1380
ccggcatcgg ccgttttctc taccgcctgg cacgccgcgc cgcaggcaag gcagaagcca   1440
gatggttgtt caagacgatc tacgaacgca gtggcagcgc cggagagttc aagaagttct   1500
gtttcaccgt gcgcaagctg atcgggtcaa atgacctgcc ggagtacgat ttgaaggagg   1560
aggcggggca ggctggcccg atcctagtca tgcgctaccg caacctgatc gagggcgaag   1620
catccgccgg ttcctaatgt acggagcaga tgctagggca aattgcccta gcaggggaaa   1680
aaggtcgaaa aggtctcttt cctgtggata gcacgtacat tgggaaccca aagccgtaca   1740
ttggaaccg gaacccgtac attgggaacc caaagccgta cattgggaac cggtcacaca   1800
tgtaagtgac tgatataaaa gagaaaaaag gcgatttttc cgcctaaaac tctttaaaac   1860
ttattaaaac tcttaaaacc cgcctggcct gtgcataact gtctggccag cgcacagccg   1920
aagagctgca aaaagcgcct acccttcggt cgctgcgctc cctacgcccc gccgcttcgc   1980
gtcggcctat cgcggccgct ggccgctcaa aaatggctgg cctacggcca ggcaatctac   2040
cagggcgcgg acaagccgcg ccgtcgccac tcgaccgccg gcgcccacat caaggcaccc   2100
tgcctcgcgc gtttcggtga tgacggtgaa aacctctgac acatgcagct cccggagacg   2160
gtcacagctt gtctgtaagc ggatgccggg agcagacaag cccgtcaggg cgcgtcagcg   2220
ggtgttggcg ggtgtcgggg cgcagccatg acccagtcac gtagcgatag cggagtgtat   2280
actggcttaa ctatgcggca tcagagcaga ttgtactgag agtgcaccat atgcggtgtg   2340
aaataccgca cagatgcgta aggagaaaat accgcatcag gcgctcttcc gcttcctcgc   2400
tcactgactc gctgcgctcg gtcgttcggc tgcggcgagc ggtatcagct cactcaaagg   2460
cggtaatacg gttatccaca gaatcagggg ataacgcagg aaagaacatg tgagcaaaag   2520
gccagcaaaa ggccaggaac cgtaaaaagg ccgcgttgct ggcgtttttc cataggctcc   2580
gcccccctga cgagcatcac aaaaatcgac gctcaagtca gaggtggcga aacccgacag   2640
gactataaag ataccaggcg tttccccctg gaagctccct cgtgcgctct cctgttccga   2700
ccctgccgct taccggatac ctgtccgcct ttctcccttc gggaagcgtg cgctttctc    2760
```

```
atagctcacg ctgtaggtat ctcagttcgg tgtaggtcgt tcgctccaag ctgggctgtg    2820
tgcacgaacc ccccgttcag cccgaccgct gcgccttatc cggtaactat cgtcttgagt    2880
ccaacccggt aagacacgac ttatcgccac tggcagcagc cactggtaac aggattagca    2940
gagcgaggta tgtaggcggt gctacagagt tcttgaagtg gtggcctaac tacggctaca    3000
ctagaaggac agtatttggt atctgcgctc tgctgaagcc agttaccttc ggaaaaagag    3060
ttggtagctc ttgatccggc aaacaaacca ccgctggtag cggtggtttt tttgtttgca    3120
agcagcagat tacgcgcaga aaaaaaggat ctcaagaaga tcctttgatc ttttctacgg    3180
ggtctgacgc tcagtggaac gaaaactcac gttaagggat tttggtcatg catgatatat    3240
ctcccaattt gtgtagggct tattatgcac gcttaaaaat aataaaagca gacttgacct    3300
gatagtttgg ctgtgagcaa ttatgtgctt agtgcatcta atcgcttgag ttaacgccgg    3360
cgaagcggcg tcggcttgaa cgaatttcta gctagacatt atttgccgac taccttggtg    3420
atctcgcctt tcacgtagtg gacaaattct tccaactgat ctgcgcgcga ggccaagcga    3480
tcttcttctt gtccaagata agcctgtcta gcttcaagta tgacgggctg atactgggcc    3540
ggcaggcgct ccattgccca gtcggcagcg acatccttcg gcgcgatttt gccggttact    3600
gcgctgtacc aaatgcggga caacgtaagc actacatttc gctcatcgcc agcccagtcg    3660 gcggcgagt ccatagcgt taaggtttca tttagcgcct caaatagatc ctgttcagga    3720
accggatcaa agagttcctc cgccgctgga cctaccaagg caacgctatg ttctcttgct    3780
tttgtcagca agatagccag atcaatgtcg atcgtggctg gctcgaagat acctgcaaga    3840
atgtcattgc gctgccattc tccaaattgc agttcgcgct tagctggata acgccacgga    3900
atgatgtcgt cgtgcacaac aatggtgact tctacagcgc ggagaatctc gctctctcca    3960
ggggaagccg aagtttccaa aaggtcgttg atcaaagctc gccgcgttgt tcatcaagc    4020 cttacggtca ccgtaaccag caaatcaata tcactgtgtg gcttcaggcc gccatccact    4080
gcggagccgt acaaatgtac ggccagcaac gtcggttcga gatggcgctc gatgacgcca    4140
actacctctg atagttgagt cgatacttcg gcgatcaccg cttcccccat gatgtttaac    4200
tttgttttag ggcgactgcc ctgctgcgta acatcgttgc tgctccataa catcaaacat    4260
cgacccacgg cgtaacgcgc ttgctgcttg gatgcccgag gcatagactg taccccaaaa    4320
aaacatgtca taacaagaag ccatgaaaac cgccactgcg ccgttaccac cgctgcgttc    4380
ggtcaaggtt ctggaccagt tgcgtgacgg cagttacgct acttgcatta cagcttacga    4440
accgaacgag gcttatgtcc actgggttcg tgcccgaatt gatcacaggc agcaacgctc    4500
tgtcatcgtt acaatcaaca tgctaccctc cgcgagatca tccgtgtttc aaacccggca    4560
gcttagttgc cgttcttccg aatagcatcg gtaacatgag caaagtctgc cgccttacaa    4620
cggctctccc gctgacgccg tcccggactg atgggctgcc tgtatcgagt ggtgattttg    4680
tgccgagctg ccgtcgggg agctgttggc tggctggtgg caggatatat tgtggtgtaa    4740
acaaattgac gcttagacaa cttaataaca cattgcggac gttttaatg tactgaatta    4800 acgccgaatt gaattcctcg agtacgtagg atccatttaa attctagagg cgcgccgata    4860
tcctctctta aggtagcgag ctcttaatta atagggataa cagggtaatg cggccgcaag    4920
ctaaaacgac ggccagtgaa ttatcaactt tgtatagaaa agttgctctg ccgacagtgg    4980
tcccaaagat ggaccccac ccacgaggag catcgtggaa aagaagacg ttccaaccac    5040 gtcttcaaag caagtggatt gatgtgataa catggtggag cacgacactc tcgtctactc    5100
caagaatatc aaagatacag tctcagaaga ccaaagggct attgagactt ttcaacaaag    5160
```

```
ggtaatatcg ggaaacctcc tcggattcca ttgcccagct atctgtcact tcatcaaaag   5220
gacagtagaa aaggaaggtg gcacctacaa atgccatcat tgcgataaag gaaaggctat   5280
cgttcaagat gcctctgccg acagtggtcc caaagatgga cccccaccca cgaggagcat   5340
cgtggaaaaa gaagacgttc caaccacgtc ttcaaagcaa gtggattgat gtgatatctc   5400
cactgacgta agggatgacg cacaatccca ctatccttcg caagacccct cctctatata   5460
aggaagttca tttcatttgg agaggacacg ctgcaagttt gtacaaaaaa gcaggctaga   5520 ccgggggggca atgagatatg aaaaagcctg aactcaccgc gacgtctgtc gagaagtttc   5580
tgatcgaaaa gttcgacagc gtctccgacc tgatgcagct ctcggagggc gaagaatctc   5640
gtgctttcag cttcgatgta ggagggcgtg gatatgtcct gcgggtaaat agctgcgccg   5700
atggtttcta caaagatcgt tatgtttatc ggcactttgc atcggccgcg ctcccgattc   5760
cggaagtgct tgacattggg gaattcagcg agagcctgac ctattgcatc tcccgccgtg   5820
cacagggtgt cacgttgcaa gacctgcctg aaaccgaact gcccgctgtt ctgcagccgg   5880
tcgcggaggc catggatgcg atcgctgcgg ccgatcttag ccagacgagc gggttcggcc   5940
cattcggacc gcaaggaatc ggtcaataca ctacatggcg tgatttcata tgcgcgattg   6000
ctgatcccca tgtgtatcac tggcaaactg tgatggacga caccgtcagt gcgtccgtcg   6060
cgcaggctct cgatgagctg atgctttggg ccgaggactg ccccgaagtc cggcacctcg   6120
tgcacgcgga tttcggctcc aacaatgtcc tgacggacaa tggccgcata acagcggtca   6180
ttgactggag cgaggcgatg ttcggggatt cccaatacga ggtcgccaac atcttcttct   6240
ggaggccgtg gttggcttgt atggagcagc agacgcgcta cttcgagcgg aggcatccgg   6300
agcttgcagg atcgccgcgg ctccgggcgt atatgctccg cattggtctt gaccaactct   6360
atcagagctt ggttgacggc aatttcgatg atgcagcttg ggcgcagggt cgatgcgacg   6420
caatcgtccg atccggagcc gggactgtcg ggcgtacaca atcgcccgc agaagcgcgg   6480 ccggccgtct ggaccgatgg ctgtgtagaa gtactcgccg atagtggaaa ccgacgcccc   6540
agcactcgtc cggacccagc tttcttgtac aaagtggagt ccgcaaaaat caccagtctc   6600
tctctacaaa tctatctctc tctatttttc tccagaataa tgtgtgagta gttcccagat   6660
aagggaatta gggttcttat agggtttcgc tcatgtgttg agcatataag aaacccttag   6720
tatgtatttg tatttgtaaa atacttctat caataaaatt tctaattcct aaaaccaaaa   6780
tccagtgacc tcaactttat tatacatagt tgataattca ctggccgtgc ttattccatg   6840
gctgcaggtc gacgaattca ccggttaggg ataacagggt aataactata acggtcctaa   6900
ggtagcgagc ggccgcaagc taaaacgacg gccagtgaat tatcaacttt gtatagaaaa   6960
gttggtttgt gtcttctaga ttaatcctcc aaacttttga ttaaccaaaa aaattatcaa   7020
actaacatgt tctccttttt tctttagaaa ttctaacgaa tttatcttta tactgatttg   7080
aatatactta atttggtcat ttggatgccc tttacaacct ccttaccaaa atattgatca   7140
cagtttctat tgctaaaatc accaacaaaa cgcatgtcgc cattcataat tatgggtttca  7200 cacctacaac taggctaata agtaaataag tagcaacta gactcaggtt tgaaaaaacc   7260
ataaaagcca tatagcgttt tctcattgaa actgcgaaca cgatcgtgtg aatgttgcag   7320
tttctagttt tgatacaaac aaacaaaaac acaatttaat cttagattaa aagaaaaaa   7380 gagaacggag cccactagcc actccttcaa acgtgtctta ccaactctct tctagaaaca   7440
aattaggctt caccttcctc ttccaacctc tctctctctc tctctctctt tttctcaaac   7500
catctctcca taaagcccta atttcttcat cacaagaatc agaagaagaa acaagtttgt   7560
```

```
acaaaaaagc aggcttactg caaaaaactt atggacctgc atctaatttt cggtccaact    7620
tgcacaggaa agacgacgac cgcgatagct cttgcccagc agacagggct tccagtcctt    7680
tcgcttgatc gggtccaatg ctgtcctcaa ctatcaaccg gaagcggacg accaacagtg    7740
gaagaactga aaggaacgac gcgtctctac cttgatgatc ggcctctggt ggagggtatc    7800
atcgcagcca agcaagctca tcataggctg atcgaggagg tgtataatca tgaggccaac    7860
ggcgggctta ttcttgaggg aggatccacc tcgttgctca actgcatggc gcgaaacagc    7920
tattggagtg cagattttcg ttggcatatt attcgccaca agttacccga ccaagagacc    7980
ttcatgaaag cggccaaggc cagagttaag cagatgttgc accccgctgc aggccattct    8040
attattcaag agttggttta tctttggaat gaacctcggc tgaggcccat tctgaaagag    8100
atcgatggat atcgatatgc catgttgttt gctagccaga accagatcac ggcagatatg    8160
ctattgcagc ttgacgcaaa tatgaaggt aagttgatta atgggatcgc tcaggagtat    8220
ttcatccatg cgcgccaaca ggaacagaaa ttcccccaag ttaacgcagc cgctttcgac    8280
ggattcgaag gtcatccgtt cggaatgtat taggtaccca gctttcttgt acaaagtggg    8340
atcgttcaaa catttggcaa taaagtttct taagattgaa tcctgttgcc ggtcttgcga    8400
tgattatcat ataatttctg ttgaattacg ttaagcatgt aataattaac atgtaatgca    8460
tgacgttatt tatgagatgg ttttttatga ttagagtccc gcaattatac atttaatacg    8520
cgatagaaaa caaatatag cgcgcaaact aggataaatt atcgcgcgcg tgtcatcta    8580 tgttactaga tccaacttta ttatacatag ttgataattc actggccgtc gcttattcca    8640
tggctgcagg tcgacgaatt caccggttaa ctataacggt cctaaggtag cgatggcaaa    8700
cagctattat gggtattatg ggtggttctt tatgcggaca ctgacggctt tatgcctgca    8760
ggtcgcgagc gatcgcggta ccgcccgggc gtcgacaggc ctaagcttag cttgagcttg    8820
gatcagattg tcgtttcccg ccttcagttt aaactatcag tgtttgacag gatatattgg    8880
cgggtaaacc taagagaaaa gagcgtttat tagaataacg gatatttaaa agggcgtgaa    8940
aaggtttatc cgttcgtcca tttgtatgtg catgccaacc acagggttcc cctcgggatc    9000
aaagtacttt gatccaaccc ctccgctgct atagtgcagt cggcttctga cgttcagtgc    9060
agccgtcttc tgaaaacgac atgtcgcaca agtcctaagt tacgcgacag gctgccgccc    9120 tgccctttc ctggcgtttt cttgtcgcgt gttttagtcg cataaagtag aatacttgcg    9180
actagaaccg gagacattac gccatgaaca agagcgccgc cgctggcctg ctgggctatg    9240
cccgcgtcag caccgacgac caggacttga ccaaccaacg ggccgaactg cacgcggccg    9300
gctgcaccaa gctgttttcc gagaagatca ccggcaccag gcgcgaccgc ccggagctgg    9360
ccaggatgct tgaccaccta cgccctggcg acgttgtgac agtgaccagg ctagaccgcc    9420
tggcccgcag cacccgcgac ctactggaca ttgccgagcg catccaggag gccggcgcgg    9480
gcctgcgtag cctggcagag ccgtgggccg acaccaccac gccggccggc cgcatggtgt    9540
tgaccgtgtt cgccggcatt gccgagttcg agcgttccct aatcatcgac cgcacccgga    9600
gcgggcgcga ggccgccaag gcccgaggcg tgaagtttgg ccccgccct accctcaccc    9660 cggcacagat cgcgcacgcc cgcgagctga tcgaccagga aggccgcacc gtgaaagagg    9720
cggctgcact gcttggcgtg catcgctcga ccctgtaccg cgcacttgag cgcagcgagg    9780
aagtgacgcc caccgaggcc aggcggcgcg gtgccttccg tgaggacgca ttgaccgagg    9840
ccgacgccct ggcggccgcc gagaatgaac gccaagagga caagcatga aaccgcacca    9900 ggacggccag gacgaaccgt ttttcattac cgaagagatc gaggcggaga tgatcgcggc    9960
```

```
cgggtacgtg ttcgagccgc ccgcgcacgt ctcaaccgtg cggctgcatg aaatcctggc   10020
cggtttgtct gatgccaagc tggcggcctg gccggccagc ttggccgctg aagaaaccga   10080
gcgccgccgt ctaaaaaggt gatgtgtatt tgagtaaaac agcttgcgtc atgcggtcgc   10140
tgcgtatatg atgcgatgag taaataaaca aatacgcaag gggaacgcat gaaggttatc   10200
gctgtactta accagaaagg cgggtcaggc aagacgacca tcgcaaccca tctagcccgc   10260
gccctgcaac tcgccggggc cgatgttctg ttagtcgatt ccgatcccca gggcagtgcc   10320
cgcgattggg cggccgtgcg ggaagatcaa ccgctaaccg ttgtcggcat cgaccgcccg   10380
acgattgacc gcgacgtgaa ggccatcggc cggcgcgact tcgtagtgat cgacggagcg   10440
ccccaggcgg cggacttggc tgtgtccgcg atcaaggcag ccgacttcgt gctgattccg   10500
gtgcagccaa gcccttacga catatgggcc accgccgacc tggtggagct ggttaagcag   10560
cgcattgagg tcacggatgg aaggctacaa gcggcctttg tcgtgtcgcg ggcgatcaaa   10620
ggcacgcgca tcggcggtga ggttgccgag gcgctggccg ggtacgagct gcccattctt   10680
ga                                                                 10682

<210> SEQ ID NO 15
<211> LENGTH: 7862
<212> TYPE: DNA
<213> ORGANISM: Artificial
<220> FEATURE:
<223> OTHER INFORMATION: Synthetic construct

<400> SEQUENCE: 15
ttatacatag ttgataattc actggccgtc gtggggatc cactagttct agagcggccg     60
ccaccgcggt ggagctccag cttttgttcc ctttagtgag ggttaatttc gagcttggcg    120
taatcatggt catagctgtt tcctgtgtga attgttatc cgctcacaat tccacacaac    180
atacgagccg gaagcataaa gtgtaaagcc tggggtgcct aatgagtgag ctaactcaca    240
ttaattgcgt tgcgctcact gcccgctttc cagtcgggaa acctgtcgtg ccagctgcat    300
taatgaatcg gccaacgcgc ggggagaggc ggtttgcgta ttgggcgctc ttccgcttcc    360
tcgctcactg actcgctgcg ctcggtcgtt cggctgcggc gagcggtatc agctcactca    420
aaggcggtaa tacggttatc cacagaatca ggggataacg caggaaagaa catgtgagca    480
aaaggccagc aaaaggccag gaaccgtaaa aaggccgcgt tgctggcgtt tttccatagg    540
ctccgccccc ctgacgagca tcacaaaaat cgacgctcaa gtcagaggtg gcgaaacccg    600
acaggactat aaagatacca ggcgtttccc cctggaagct ccctcgtgcg ctctcctgtt    660
ccgaccctgc cgcttaccgg atacctgtcc gcctttctcc cttcgggaag cgtggcgctt    720
tctcatagct cacgctgtag gtatctcagt tcggtgtagg tcgttcgctc caagctgggc    780
tgtgtgcacg aaccccccgt tcagcccgac cgctgcgcct tatccggtaa ctatcgtctt    840
gagtccaacc cggtaagaca cgacttatcg ccactggcag cagccactgg taacaggatt    900
agcagagcga ggtatgtagg cggtgctaca gagttcttga agtggtggcc taactacggc    960
tacactagaa ggacagtatt tggtatctgc gctctgctga gccagttac cttcggaaaa   1020 agagttggta gctcttgatc cggcaaacaa accaccgctg gtagcggtgg ttttttgtt   1080 tgcaagcagc agattacgcg cagaaaaaaa ggatctcaag aagatccttt gatcttttct   1140
acggggtctg acgctcagtg gaacgaaaac tcacgttaag ggattttggt catgagatta   1200
tcaaaaagga tcttcaccta gatcctttta aattaaaaat gaagttttaa atcaatctaa   1260
agtatatatg agtaaacttg gtctgacagt taccaatgct taatcagtga ggcacctatc   1320
```

```
tcagcgatct gtctatttcg ttcatccata gttgcctgac tccccgtcgt gtagataact   1380
acgatacggg agggcttacc atctggcccc agtgctgcaa tgataccgcg agacccacgc   1440
tcaccggctc cagatttatc agcaataaac cagccagccg aagggccga gcgcagaagt    1500 ggtcctgcaa ctttatccgc ctccatccag tctattaatt gttgccggga agctagagta   1560
agtagttcgc cagttaatag tttgcgcaac gttgttgcca ttgctacagg catcgtggtg   1620
tcacgctcgt cgtttggtat ggcttcattc agctccggtt cccaacgatc aaggcgagtt   1680
acatgatccc ccatgttgtg caaaaaagcg gttagctcct tcggtcctcc gatcgttgtc   1740
agaagtaagt tggccgcagt gttatcactc atggttatgg cagcactgca taattctctt   1800
actgtcatgc catccgtaag atgcttttct gtgactggtg agtactcaac caagtcattc   1860
tgagaatagt gtatgcggcg accgagttgc tcttgcccgg cgtcaatacg ggataatacc   1920
gcgccacata gcagaacttt aaaagtgctc atcattggaa aacgttcttc ggggcgaaaa   1980
ctctcaagga tcttaccgct gttgagatcc agttcgatgt aacccactcg tgcacccaac   2040
tgatcttcag catcttttac tttcaccagc gtttctgggt gagcaaaaac aggaaggcaa   2100
aatgccgcaa aaaagggaat aagggcgaca cggaaatgtt gaatactcat actcttcctt   2160
tttcaatatt attgaagcat ttatcagggt tattgtctca tgagcggata catatttgaa   2220
tgtatttaga aaaataaaca aataggggtt ccgcgcacat ttccccgaaa agtgccacct   2280
gacgcgccct gtagcggcgc attaagcgcg gcgggtgtgg tggttacgcg cagcgtgacc   2340
gctacacttg ccagcgccct agcgcccgct ccttcgctt tcttcccttc ctttctcgcc    2400
acgttcgccg gctttccccg tcaagctcta aatcggggc tcccttaggg gttccgattt    2460
agtgctttac ggcacctcga cccccaaaaaa cttgattagg gtgatggttc acgtagtggg   2520
ccatcgccct gatagacggt ttttcgccct ttgacgttgg agtccacgtt ctttaatagt   2580
ggactcttgt tccaaactgg aacaacactc aaccctatct cggtctattc ttttgattta   2640
taagggattt tgccgatttc ggcctattgg ttaaaaaatg agctgattta acaaaaattt   2700
aacgcgaatt ttaacaaaat attaacgctt acaatttcca ttcgccattc aggctgcgca   2760
actgttggga agggcgatcg gtgcgggcct cttcgctatt acgccagctg gcgaaagggg   2820
gatgtgctgc aaggcgatta agttgggtaa cgccagggtt ttcccagtca cgacgttgta   2880
aaacgacggc cagtgaattg taatacgact cactataggg cgaattgggt accgggcccc   2940
ccctcgaggt cgacggtatc gataagcttg atatcgaatt ctcatgtttg acagcttatc   3000
atcggatcta gtaacataga tgacaccgcg cgcgataatt tatcctagtt tgcgcgctat   3060
attttgtttt ctatcgcgta ttaaatgtat aattgcggga ctctaatcat aaaaacccat   3120
ctcataaata acgtcatgca ttacatgtta attattacat gcttaacgta attcaacaga   3180
aattatatga taatcatcgc aagaccggca acaggattca atcttaagaa actttattgc   3240
caaatgtttg aacgatctgc aggtcgacgg atcagatctc ggtgacgggc aggaccggac   3300
ggggcggtac cggcaggctg aagtccagct gccagaaacc cacgtcatgc cagttcccgt   3360
gcttgaagcc ggccgcccgc agcatgccgc gggggcata tccgagcgcc tcgtgcatgc    3420
gcacgctcgg tcgttgggc agcccgatga cagcgaccac gctcttgaag ccctgtgcct   3480
ccagggactt cagcaggtgg gtgtagagcg tggagcccag tcccgtccgc tggtggcggg   3540
gggagacgta cacggtcgac tcggccgtcc agtcgtaggc gttgcgtgcc ttccagggc    3600 ccgcgtaggc gatgccggcg acctcgccgt ccacctcggc gacgagccag ggatagcgct   3660
cccgcagacg gacgaggtcg tccgtccact cctgcggttc ctgcggctcg gtacggaagt   3720
```

```
tgaccgtgct tgtctcgatg tagtggttga cgatggtgca gaccgccggc atgtccgcct    3780
cggtggcacg gcggatgtcg gccgggcgtc gttctgggct catggttact tcctaatcga    3840
tggatcctct agagtcgacc tgcagaagta acaccaaaca acagggtgag catcgacaaa    3900
agaaacagta ccaagcaaat aaatagcgta tgaaggcagg gctaaaaaaa tccacatata    3960
gctgctgcat atgccatcat ccaagtatat caagatcaaa ataattataa aacatacttg    4020
tttattataa tagataggta ctcaaggtta gagcatatga atagatgctg catatgccat    4080
catgtatatg catcagtaaa acccacatca acatgtatac ctatcctaga tcgatatttc    4140
catccatctt aaactcgtaa ctatgaagat gtatgacaca cacatacagt tccaaaatta    4200
ataaatacac caggtagttt gaaacagtat tctactccga tctagaacga atgaacgacc    4260
gcccaaccac accacatcat cacaaccaag cgaacaaaaa gcatctctgt atatgcatca    4320
gtaaaacccg catcaacatg tatacctatc ctagatcgat atttccatcc atcattttca    4380
attcgtaact atgaatatgt atggcacaca catacagatc caaaattaat aaatccacca    4440
ggtagtttga aacagaattc tactccgatc tagaacgacc gcccaaccag accacatcat    4500
cacaaccaag acaaaaaaaa gcatgaaaag atgcccgac aaacaagtgc acggcatata    4560
ttgaaataaa ggaaaagggc aaaccaaacc ctatgcaacg aaacaaaaaa aatcatgaaa    4620
tcgatcccgt ctgcggaacg gctagagcca tcccaggatt ccccaaagag aaacactggc    4680
aagttagcaa tcagaacgtg tctgacgtac aggtcgcatc cgtgtacgaa cgctagcagc    4740
acggatctaa cacaaacacg gatctaacac aaacatgaac agaagtagaa ctaccgggcc    4800
ctaaccatgg accggaacgc cgatctagag aaggtagaga ggggggggggg gggaggacga    4860 gcggcgtacc ttgaagcgga ggtgccgacg ggtggatttg ggggagatct ggttgtgtgt    4920
gtgtgcgctc cgaacaacac gaggttgggg aaagagggtg tggagggggt gtctatttat    4980 tacgcgggc gaggaaggga aagcgaagga gcggtgggaa aggaatcccc cgtagctgcc    5040
ggtgccgtga gaggaggagg aggccgcctg ccgtgccggc tcacgtctgc cgctccgcca    5100
cgcaatttct ggatgccgac agcggagcaa gtccaacggt ggagcggaac tctcgagagg    5160
ggtccagagg cagcgacaga gatgccgtgc cgtctgcttc gcttggcccg acgcgacgct    5220
gctggttcgc tggttggtgt ccgttagact cgtcgacggc gtttaacagg ctggcattat    5280
ctactcgaaa caagaaaaat gtttccttag ttttttttaat ttcttaaagg gtatttgttt    5340 aattttagt cacttttattt tattctattt tatatctaaa ttattaaata aaaaaactaa    5400
aatagagttt tagttttctt aatttagagg ctaaaataga ataaaataga tgtactaaaa    5460
aaattagtct ataaaaacca ttaaccctaa accctaaatg gatgtactaa taaaatggat    5520
gaagtattat ataggtgaag ctatttgcaa aaaaaaagga gaacacatgc acactaaaaa    5580
gataaaactg tagagtcctg ttgtcaaaat actcaattgt cctttagacc atgtctaact    5640 gttcattat atgattctct aaaacactga tattattgta gtactataga ttatattatt    5700
cgtagagtaa agtttaaata tatgtataaa gatagataaa ctgcacttca acaagtgtg    5760 acaaaaaaa tatgtggtaa ttttttataa cttagacatg caatgctcat tatctctaga    5820
gaggggcacg accgggtcac gctgcactgc aggcatgcaa gcttgaattc ctgcagcccc    5880
gccaagctat caactttgta tagaaaagtt ggttgtgtc ttctagatta tcctccaaa    5940 cttttgatta accaaaaaaa ttatcaaact aacatgttct ccttttttct ttagaaattc    6000
taacgaattt atctttatac tgatttgaat atacttaatt tggtcatttg gatgcccttt    6060
acaacctcct taccaaactc actatggcaa atatatacta ttttccattg taacataaat    6120
```

-continued

```
gtccataatt tgaattaaat tcgttgcagt acgaaaccat ccaactttgt ccaaaaacaa    6180
aatccttata actatttact ttaatgtaaa tatatcctct acttttgttt ttacaaccct    6240
agctcaaaca aatttattat ttgcgataaa aaatcatatc gaacaaactc gatgattttt    6300
tttttcttac gttattaatg aaactaaaat atagaaaaaa acaagatgaa ccaaattttc    6360
acctatctaa ctacttaaat ataatatgat taaatttggt aaagtttgaa aagtttcttt    6420
agaaatgtga aatattgatc acagtttcta ttgctaaaat caccaacaaa acgcatgtcg    6480
ccattcataa ttatggtttc acacctacaa ctaggctaat aagtaaataa gtagacaact    6540
agactcaggt ttgaaaaaac cataaaagcc atatagcgtt ttctcattga aactgcgaac    6600
acgatcgtgt gaatgttgca gtttctagtt ttgatacaaa caaacaaaaa cacaatttaa    6660
tcttagatta aaaagaaaaa agagaacgga gcccactagc cactccttca aacgtgtctt    6720
accaactctc ttctagaaac aaattaggct tcaccttcct cttccaacct ctctctctct    6780
ctctctctct ttttctcaaa ccatctctcc ataaagccct aatttcttca tcacaagaat    6840
cagaagaaga aacaagtttg tacaaaaaag caggcttact gcaaaaaact tatggacctg    6900
catctaattt tcggtccaac ttgcacagga aagacgacga ccgcgatagc tcttgcccag    6960
cagacagggc ttccagtcct ttcgcttgat cgggtccaat gctgtcctca actatcaacc    7020
ggaagcggac gaccaacagt ggaagaactg aaaggaacga cgcgtctcta ccttgatgat    7080
cggcctctgg tggagggtat catcgcagcc aagcaagctc atcataggct gatcgaggag    7140
gtgtataatc atgaggccaa cggcgggctt attcttgagg gaggatccac ctcgttgctc    7200
aactgcatgg cgcgaaacag ctattggagt gcagattttc gttggcatat tattcgccac    7260
aagttacccg accaagagac cttcatgaaa gcggccaagg ccagagttaa gcagatgttg    7320 cacccgctg caggccattc tattattcaa gagttggttt atctttggaa tgaacctcgg    7380
ctgaggccca ttctgaaaga gatcgatgga tatcgatatg ccatgttgtt tgctagccag    7440
aaccagatca cggcagatat gctattgcag cttgacgcaa atatggaagg taagttgatt    7500
aatgggatcg ctcaggagta tttcatccat gcgcgccaac aggaacagaa attcccccaa    7560
gttaacgcag ccgctttcga cggattcgaa ggtcatccgt tcggaatgta ttaggtaccc    7620
agctttcttg tacaaagtgg agtccgcaaa aatcaccagt ctctctctac aaatctatct    7680
ctctctattt ttctccagaa taatgtgtga gtagttccca gataagggaa ttagggttct    7740
tatagggttt cgctcatgtg ttgagcatat aagaaaccct tagtatgtat ttgtatttgt    7800
aaaatacttc tatcaataaa atttctaatt cctaaaacca aaatccagtg acctcaactt    7860
ta                                                                   7862
```